(12) United States Patent
Butt et al.

(10) Patent No.: US 11,857,605 B2
(45) Date of Patent: *Jan. 2, 2024

(54) THIOSUCCINYL-CROSSLINKED HEMOGLOBIN CONJUGATES AND METHODS OF USE AND PREPARATION THEREOF

(71) Applicant: Billion King International Limited, Hong Kong (CN)

(72) Inventors: Kwok Chu Butt, Hong Kong (CN); Norman Fung-Man Wai, Vancouver (CA); Hiu Chi Chong, Hong Kong (CN); Wing Tat Choi, Hong Kong (CN); Colin Pak Fai Yeh, Hong Kong (CN); Benjamin Chi Yin Wai, Vancouver (CA)

(73) Assignee: Billion King International Limited, Hong Kong (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/652,700

(22) Filed: Feb. 28, 2022

(65) Prior Publication Data

US 2022/0280616 A1    Sep. 8, 2022

Related U.S. Application Data

(60) Provisional application No. 63/200,308, filed on Mar. 1, 2021.

(51) Int. Cl.
| | | |
|---|---|---|
| *A61K 38/42* | (2006.01) | |
| *A61K 47/60* | (2017.01) | |
| *A61K 47/54* | (2017.01) | |
| *A61P 9/10* | (2006.01) | |

(52) U.S. Cl.
CPC ............ *A61K 38/42* (2013.01); *A61K 47/542* (2017.08); *A61K 47/545* (2017.08); *A61K 47/60* (2017.08); *A61P 9/10* (2018.01)

(58) Field of Classification Search
None
See application file for complete search history.

(56) References Cited

U.S. PATENT DOCUMENTS

| | | | |
|---|---|---|---|
| 5,234,903 | A | 8/1993 | Nho et al. |
| 7,211,560 | B2 | 5/2007 | Looker et al. |
| 8,273,857 | B2 | 9/2012 | Hsia et al. |
| 8,697,645 | B2 | 4/2014 | Acharya et al. |
| 8,741,832 | B2 | 6/2014 | Acharya et al. |
| 9,493,616 | B2 | 11/2016 | Malavalli et al. |
| 10,029,001 | B2 | 7/2018 | Schindler |
| 10,772,937 | B2 | 9/2020 | Abuchowski et al. |
| 10,821,158 | B2 | 11/2020 | Malavalli et al. |
| 2021/0401949 | A1 | 12/2021 | Nho et al. |

FOREIGN PATENT DOCUMENTS

WO    2021/037109 A1    3/2021

OTHER PUBLICATIONS

Delgado, et al., The uses and properties of PEG-Linked proteins, Critical Reviews in Therapeutic Carrier Systems, 9(3,40:249-304 (1992) (Year: 1992).*

* cited by examiner

*Primary Examiner* — Thomas S Heard
(74) *Attorney, Agent, or Firm* — S&F/WEHRW

(57) ABSTRACT

Provided herein are thiosuccinyl-crosslinked hemoglobin conjugates useful as blood replacement agents and therapeutic proteins, pharmaceutical compositions comprising the same and the methods of use and preparation thereof.

34 Claims, 28 Drawing Sheets

| | n (average) | m |
|---|---|---|
| PEG-1K-HS | 22 | 5 |
| PEG-2K-HS | 45 | 5 |
| PEG-5K-HS | 113 | 5 |
| PEG-10K-HS | 227 | 5 |
| PEG-20K-HS | 455 | 5 |
| PEG-40K-HS | 909 | 5 |
| PEG-5K-AS | 113 | 1 |
| PEG-5K-PS | 113 | 2 |
| PEG-5K-DCS | 113 | 9 |

THIOSUCCINYL-CROSSLINKED HEMOGLOBIN CONJUGATES AND METHODS OF USE AND PREPARATION THEREOF

CROSS-REFERENCE TO RELATED APPLICATIONS

This application claims the benefit of priority of U.S. Provisional Application No. 63/200,308, filed on Mar. 1, 2021, the contents of which are hereby incorporated by reference in their entirety for all purposes.

TECHNICAL FIELD

The present disclosure generally relates to pegylated thiosuccinyl-crosslinked hemoglobin conjugates, pharmaceutical compositions comprising the same, methods for making such compositions and methods of use for repeated doses or prolonged exposure.

BACKGROUND

Polyethylene glycol (PEG) has been widely used for protein conjugation, because PEG is chemically inert, non-toxic, non-immunogenic as well as "Generally Regard As Safe" by Food and Drug Administration (FDA), which makes pegylation a gold standard to improve the pharmacological properties of therapeutic molecules.

Since PEG polymer is nonionic and hydrophilic in nature, it is highly hydrated by water molecules. When a protein is conjugated to 20 kDa PEG, the hydrodynamic volume of the resulting PEGylated protein increases by approximately 5 to 10-fold relative to the original protein size. The increase of size and hydrodynamic diameter of the protein can minimize the elimination through glomerular filtration by the kidneys. In addition, PEG moieties can adopt dynamic conformation in solution and create a shell-like structure in which PEG polymer could flip and wrap around the protein surface. This may explain why the conjugates are more resistant to proteolytic degradation, as the access to the susceptible residues is impaired. Similarly, the antigenic determinants are being shielded from exposure and thereby reduce the formation of neutralizing antibodies and the uptake by reticuloendothelial cells. Furthermore, in vitro protein stability could also be improved by pegylation, because hydrophobic patches that are involved in protein interaction and subsequent aggregation could also be minimized. Aggregated protein therapeutic could lead to immunological response when administrated to patients and rendering the drug ineffective. Therefore, pegylation of therapeutic proteins can impart several significant pharmacological advantages over the unpegylated form, such as 1) prolonging the residence time in the body as the size and hydrodynamic diameter of the protein increases with concomitant reduced clearance via glomerular filtration, 2) increasing the in vivo stability by reducing the proteolytic degradation during systemic circulation, 3) reducing or eliminating the protein immunogenicity through shielding the antigenic epitopes of the protein and reducing the protein aggregation formation, 4) improving the solubility of the pegylated molecules owning to the hydrophilic nature of PEG and 5) maintaining or even improving pharmacokinetic and pharmacodynamics characteristics of the protein drug.

The success of pegylation is governed by a thorough understanding of both the structure-function relationship of the target protein as well as the physiochemical properties of the PEG molecule. For the protein, reactive amino acid residues, such as histidine, aspartic acid, glutamic acid, serine, threonine, tyrosine, arginine, lysine, cysteine, N-terminals, C-terminals as well as the vicinal hydroxyl groups of glycoproteins are potential candidates for PEG conjugation. The N-terminal, lysine and cysteine are most commonly moieties exploited for PEG conjugation, in which the distribution and prevalence of these reactive amino acids will determine the site and the number of PEG attachment. For instance, lysine is one of the most abundant amino acid residues in a protein and it may contribute up to 10% of the total amino acids. Pegylation through lysine residues may result in heterogeneous mixtures of conjugates, these pegylated isomers vary in the number of PEG attached to the site of attachment. Therefore, pegylation reactions are preferably conducted in a controlled batch system and the formation of all products in equal conditions, in order to avoid the heterogeneity of pegylated conjugates and potential formation of undesirable products. Thus, FDA has imposed stringent requirement towards pegylated biopharmaceuticals, which requires evidence of reproducibility thereby minimizing the batch to batch variation.

While pegylation of therapeutic proteins often leads to improved physiochemical properties and pharmacokinetics profiles when compared to unpegylated ones, some drawbacks have been noted. It is also worthwhile to understand the limitations, such as hampered interaction and activity resulting from steric hindrance, potential reactivity towards the immune system and accumulation of PEG in the body under certain circumstances. For instance, pegylated therapeutics usually exhibit different physiochemical properties from the parent molecule. The highly hydrated and flexible PEG moiety creates steric hindrance, which may impede the enzyme-substrate or receptor-ligand binding thereby resulting in diminished in vitro biological activity. However, this can be compensated by prolonged plasma circulating time and thus increasing the overall systemic exposure. The resulting change in the pharmacological profile creates an overall improvement on therapeutic efficacy and therefore, the in vivo biological activity is also enhanced. Besides, PEG molecules are generally regarded as non-immunogenic, but a few reports suggested that chronic exposure and repeated administration of pegylated liposome and proteins could induce anti-PEG immune response, resulting in the formation of neutralizing antibodies against the PEG moiety. Lastly, high doses of pegylated proteins could also induce renal tubular vacuolization in some toxicology studies, yet this phenomenon disappears on cessation of treatment and no toxic consequences have been observed. Thus, the use of PEG derivatives is still generally regarded as immunologically safe and non-toxic under most circumstances.

Over the past decade, pegylated hemoglobin-based oxygen carriers (HBOCs) have received much attention for their oxygen delivery and plasma expanding ability in a wide variety of medical applications, such as ischemic stroke, autoimmune diseases and cancer treatments. Up to now, at least six pegylated HBOCs have been developed using mammalian hemoglobin as the original substrate. Apart from diaspirin crosslinked pegylated human hemoglobin developed by Schindler William (Schindler, W., 2018, U.S. Pat. No. 10,029,001), these pegylated HBOCs have PEG directly conjugated to the original substrate, without any intramolecular crosslinking between the globin chains of the hemoglobin molecule. The pegylation conjugation strategies used in these pegylated HBOCs are through random pegylation of lysine, thiolated lysine, cysteine or histidine residues of the hemoglobin surface or specific pegylation of cysteine residue at beta93 attached to polyalkylene. Most importantly, conventional pegylation processes alter the oxygen binding capability of the hemoglobin molecule and the pegylated HBOCs produced have higher affinity for oxygen, indicated by their low p50 ranges (<15 mmHg). Among them, two pegylated HBOCs, Euro-PEG-Hb and MP4 generated by maleimide chemistry based pegylation, using human adult hemoglobin (HbA) as the original substrate, have been approved for clinical trials.

There is thus a need in the art for a technique to create pegylated crosslinked hemoglobin with a relatively low oxygen affinity property for the designated indications and oxygen therapies. Ideally, the pegylation step used doesn't alter the oxygen affinity properties of the intramolecularly-crosslinked hemoglobin with improved pharmacokinetics and pharmacodynamics properties.

SUMMARY

The present disclosure generally relates to pegylated thiosuccinyl-crosslinked hemoglobin conjugates, pharmaceutical compositions comprising the same, and methods of preparation and use thereof.

The thiosuccinyl crosslinkers in the thiosuccinyl-crosslinked hemoglobin analogs described in Butt K. C. et al., U.S. Non-provisional patent application Ser. No. 16/947,993 (the content of which is hereby incorporated by reference) are useful for hemoglobin stabilization. The thiosuccinyl-crosslinked hemoglobin analogs have been shown to be more stable and have improved superior oxygen offloading capability, compared to the corresponding fumaryl-crosslinked hemoglobin. The pharmaceutical composition comprising the thiosuccinyl-crosslinked hemoglobin analogs can be used for improving the delivery of oxygen and treatment of global and regional ischemic/hypoxic conditions, including hemorrhagic shock, myocardial ischemia reperfusion injury, peripheral artery disease and traumatic brain injury. In addition, such composition can also be used for treating autoimmune diseases and cancer treatment.

Provided herein is a thiosuccinyl-crosslinked hemoglobin conjugate comprising at least one water-soluble polymer, such as PEG, which can be produced by conjugation of one or more water-soluble polymers to the thiosuccinyl-crosslinked hemoglobin (e.g., to the surface-exposed lysine residues). The average molecular weight and hydrodynamic diameter of the thiosuccinyl-crosslinked hemoglobin conjugate can increase when compared to the corresponding thiosuccinyl-crosslinked hemoglobin. Surprisingly, this conjugation of water-soluble polymers, such as PEG, to the thiosuccinyl-crosslinked hemoglobin does not alter the in vitro stability and the p50 value of the thiosuccinyl-crosslinked hemoglobin. As such, the therapeutic efficacy of the thiosuccinyl-crosslinked hemoglobin conjugates for different indications can be precisely designed and retained after conjugation with one or more water-soluble polymers.

In a first aspect, provided herein is a thiosuccinyl-crosslinked hemoglobin conjugate comprising a tetrameric hemoglobin; at least one water-soluble polymer covalently attached to the tetrameric hemoglobin via an optional linker; and at least one thiosuccinyl crosslinking moiety of Formula 1:

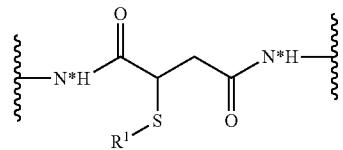

or a pharmaceutically acceptable salt or zwitterion thereof, wherein each $N^*$ independently represents a nitrogen selected from the group consisting of a nitrogen in a lysine residue side chain in the tetrameric hemoglobin and a nitrogen at a N-terminus in the tetrameric hemoglobin;

$R^1$ is alkyl, alkenyl, cycloalkyl, heterocycloalkyl, aryl, aralkyl, heteroaryl, or $-(CR_2)_nY$, wherein n is an integer number selected from 0-10;

R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S;

Y is selected from the group consisting of $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, $-(NR^4)S(O)_2OR^4$, and $-(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$;

$R^3$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; and $R^4$ for each instance is independently selected from the group consisting of hydrogen, alkyl, aralkyl, cycloalkyl, heterocycloalkyl, aryl, and heteroaryl; or $R^1$ is a moiety selected from the group consisting of:

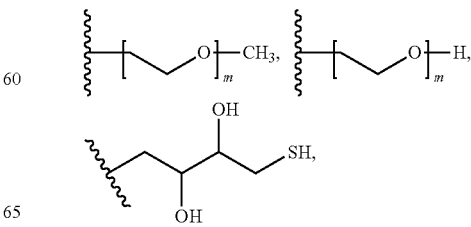

and $N^5$-(1-((carboxymethyl)amino)-1-oxo-3$\lambda^3$-propan-2-yl) glutamine or a pharmaceutically acceptable salt thereof, wherein m is a whole number selected from 1-1,000.

In certain embodiments, the at least one water-soluble polymer comprises a polyalkylene glycol.

In certain embodiments, the at least one water-soluble polymer and the linker have a formula selected from the group consisting of:

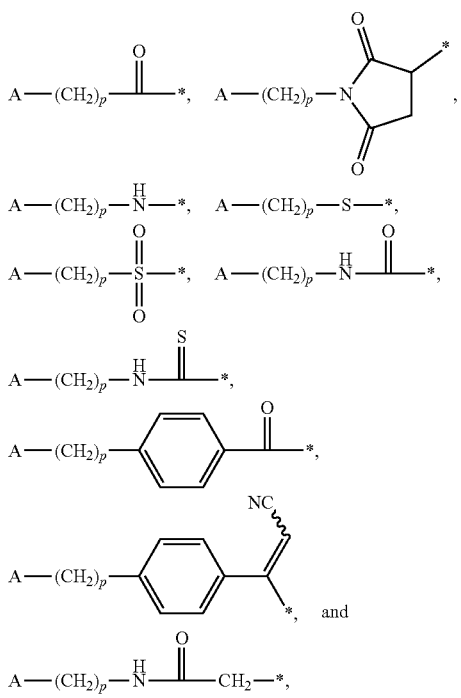

wherein A represents the water-soluble polymer; p is a whole number selected from 1-20; and * represents the tetrameric hemoglobin.

In certain embodiments, at least one water-soluble polymer and the linker have the formula:

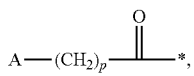

wherein A is a polyethylene glycol; p is a whole number selected from 1-20; and * represents the tetrameric hemoglobin.

In certain embodiments, the polyethylene glycol has an average molecular weight between 1,000 to 50,000 Daltons.

In certain embodiments, the thiosuccinyl-crosslinked hemoglobin conjugate comprises between 1-50 water-soluble polymers, wherein each water-soluble polymer is covalently attached to the tetrameric hemoglobin via a linker.

In certain embodiments, the thiosuccinyl-crosslinked hemoglobin conjugate comprises between 10-15 water-soluble polymers, wherein each water-soluble polymer is covalently attached to the tetrameric hemoglobin via a linker.

In certain embodiments, $R^1$ is a moiety of Formula 2:

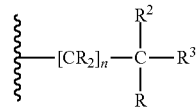

wherein n is a whole number selected from the group consisting of 0, 1, 2, 3, and 4;

R for each instance is independently selected from the group consisting of hydrogen, alkyl, aralkyl, cycloalkyl, heterocycloalkyl, aryl, and heteroaryl;

$R^2$ is hydrogen, alkyl, aralkyl, cycloalkyl, heterocycloalkyl, aryl, heteroaryl, —N($R^4$)$_2$, —NH(C=O)$R^4$, or —NH(C=O)N($R^4$)$_2$;

$R^3$ is hydrogen, alkyl, aralkyl, cycloalkyl, heterocycloalkyl, aryl, heteroaryl, —CO$_2$$R^4$, —(C=O)NH$R^4$, —O$R^4$, or —N($R^4$)$_2$; and $R^4$ for each instance is independently selected from the group consisting of hydrogen, alkyl, aralkyl, cycloalkyl, heterocycloalkyl, aryl, and heteroaryl;

or $R^1$ is a moiety selected from the group consisting of:

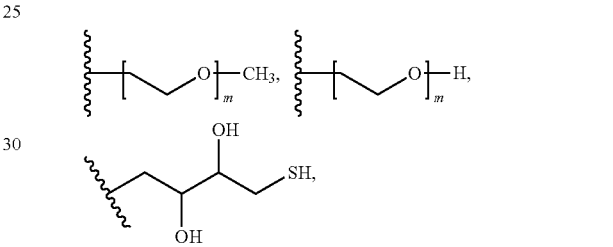

$N^5$-(1-((carboxymethyl)amino)-1-oxo-3$\lambda^3$-propan-2-yl) glutamine or a pharmaceutically acceptable salt thereof, wherein m is a whole number selected from 1-1,000.

In certain embodiments, n is 1 or 2; R is hydrogen; $R^2$ is —NH$R^4$, —NH(C=O)$R^4$, or —NH(C=O)$R^4$N($R^4$)$_2$; and $R^3$ is hydrogen, —O$R^4$, —CO$_2$$R_4$, or —(C=O)NH$R^4$, wherein $R^4$ for each instance is independently selected from the group consisting of hydrogen and alkyl.

In certain embodiments, $R^1$ is selected from the group consisting of:

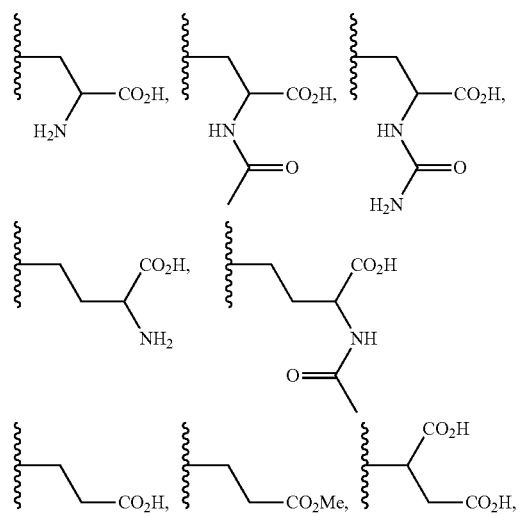

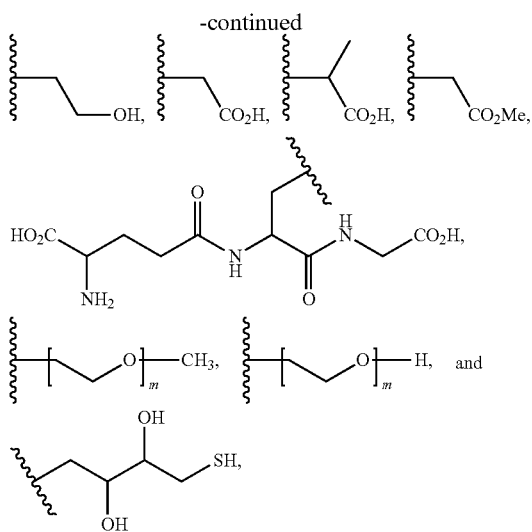

or a pharmaceutically acceptable salt or zwitterion thereof, wherein m is a whole number selected from 1-1,000.

In certain embodiments, the thiosuccinyl-crosslinked hemoglobin conjugate comprises 10-15 water-soluble polymers and linker having the formula:

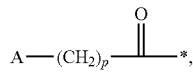

wherein A is a polyethylene glycol having an average molecular weight of 3,000-7,000 Daltons; p is a whole number selected from 1-20; and * represents the tetrameric hemoglobin.

In certain embodiments, each N* independently represents a nitrogen selected from the group consisting of a nitrogen in a lysine residue side chain in a beta globin chain of the tetrameric hemoglobin and a nitrogen at a N-terminus in a beta globin chain of the tetrameric hemoglobin.

In certain embodiments, the thiosuccinyl-crosslinked hemoglobin conjugate is substantially pure.

In certain embodiments, the thiosuccinyl-crosslinked hemoglobin conjugate comprises 1, 2, or 3 thiosuccinyl crosslinking moieties of Formula 1.

In certain embodiments, the at least one thiosuccinyl crosslinking moiety crosslinks two beta globin chains of the tetrameric hemoglobin.

In certain embodiments, the tetrameric hemoglobin is human hemoglobin, bovine hemoglobin, or porcine hemoglobin.

In certain embodiments, the thiosuccinyl-crosslinked hemoglobin conjugate is substantially stroma-free.

In a second aspect, provided herein is a pharmaceutical composition comprising at least one of the thiosuccinyl-crosslinked hemoglobin conjugate described herein and at least one pharmaceutically acceptable excipient.

In certain embodiments, the thiosuccinyl-crosslinked hemoglobin conjugate is present in the pharmaceutical composition at a weight percentage between 10-90%.

In certain embodiments, the pharmaceutical composition comprises thiosuccinyl-crosslinked hemoglobin conjugate comprising 1, 2, or 3 thiosuccinyl crosslinking moieties of Formula 1; or a combination thereof.

In a third aspect, provided herein is a method for preparing the thiosuccinyl-crosslinked hemoglobin conjugate described herein, the method comprising: contacting a tetrameric hemoglobin with a fumaryl crosslinking agent thereby forming a fumaryl-crosslinked hemoglobin; contacting the fumaryl-crosslinked hemoglobin with a thiol or a pharmaceutically acceptable salt or zwitterion thereof thereby forming a thiosuccinyl-crosslinked hemoglobin; and contacting the thiosuccinyl-crosslinked hemoglobin with a reactive water-soluble polymer reagent comprising a water-soluble polymer, a reactive functional group and optionally a linker, wherein the linker is covalently attached to the water-soluble polymer and the reactive functional group, thereby forming the thiosuccinyl-crosslinked hemoglobin conjugate.

In certain embodiments, the fumaryl crosslinking agent is selected from the group consisting of bis-3,5-dibromosalicyl fumarate (DBSF), fumaryl chloride and bis(salicyl) fumarate.

In certain embodiments, the thiol has the formula: $R^1SH$ or a pharmaceutically acceptable salt or zwitterion thereof, wherein $R^1$ is alkyl, alkenyl, cycloalkyl, heterocycloalkyl, aryl, aralkyl, heteroaryl, or $-(CR_2)_nY$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $R^1$ is alkyl, alkenyl, cycloalkyl, heterocycloalkyl, aryl, aralkyl, heteroaryl, or $-(CR_2)_nY$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, $-(NR^4)S(O)_2OR^4$, and $-(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; $R^3$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; and $R^4$ for each instance is independently selected from the group consisting of hydrogen, alkyl, aralkyl, cycloalkyl, heterocycloalkyl, aryl, and heteroaryl; or $R^1$ is a moiety selected from the group consisting of:

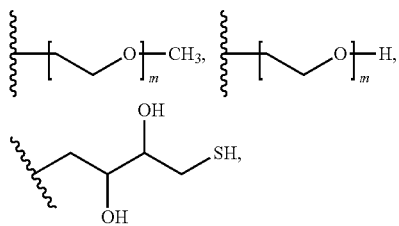

and

N⁵-(1-((carboxymethyl)amino)-1-oxo-3λ³-propan-2-yl) glutamine or a pharmaceutically acceptable salt thereof, wherein m is a whole number selected from 1-1000.

In certain embodiments, the thiol has the Formula 3:

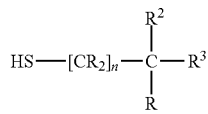

3 or a pharmaceutically acceptable salt or zwitterion thereof, wherein n is an integer selected from the group consisting of 0, 1, 2, 3, and 4;

R for each instance is independently selected from the group consisting of hydrogen, alkyl, aralkyl, cycloalkyl, heterocycloalkyl, aryl, and heteroaryl;

$R^2$ is hydrogen, alkyl, aralkyl, cycloalkyl, heterocycloalkyl, aryl, heteroaryl, —N(R⁴)₂, or —NH(C=O)R⁴;

$R^3$ is hydrogen, alkyl, aralkyl, cycloalkyl, heterocycloalkyl, aryl, heteroaryl, —CO₂R⁴, —(C=O)NHR⁴, —OR⁴, or —N(R⁴)₂; and $R^4$ for each instance is independently selected from the group consisting of hydrogen, alkyl, aralkyl, cycloalkyl, heterocycloalkyl, aryl, and heteroaryl; or the thiol is selected from the group consisting of dithiothreitol, HS(CH₂CH₂O)ₘCH₃, HS(CH₂CH₂O)ₘH, glutathione or a pharmaceutically acceptable salt thereof, wherein m is a whole number selected between 1-1000.

In certain embodiments, n is 1 or 2; R is hydrogen; $R^2$ is —NHR⁴, —NH(C=O)R⁴, or —NH(C=O)(NR⁴)₂; and $R^3$ is hydrogen, —OR⁴, —CO₂R⁴, or —(C=O)NHR⁴, wherein $R^4$ for each instance is independently selected from the group consisting of hydrogen and alkyl.

In certain embodiments, the thiol is selected from the group consisting of

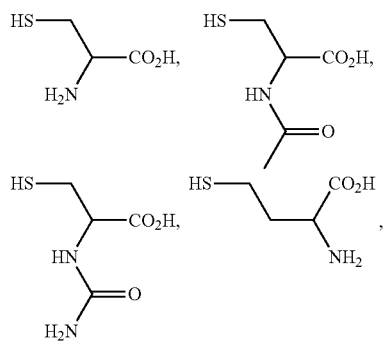

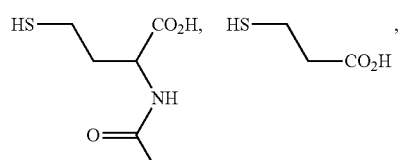

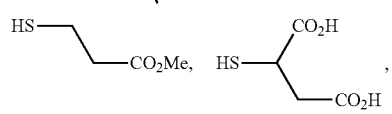

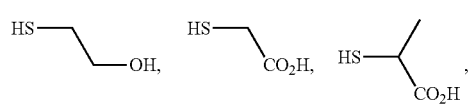

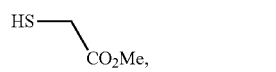

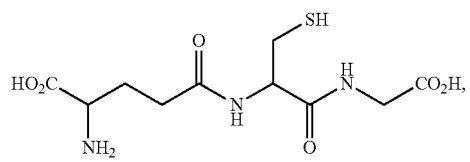

dithiothreitol, HS(CH₂CH₂O)ₘCH₃, and HS(CH₂CH₂O)ₘH or a pharmaceutically acceptable salt or zwitterion thereof, wherein m is a whole number selected between 1-1000.

In certain embodiments, the reactive water-soluble polymer reagent is selected from the group consisting of:

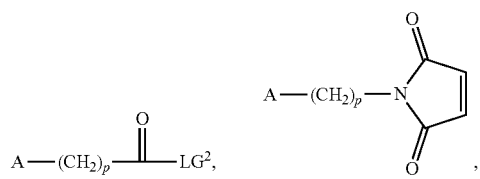

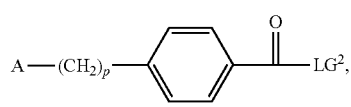

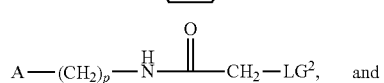

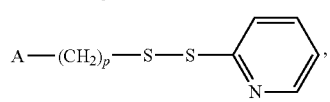

wherein A represents the water-soluble polymer; $LG^2$ is a leaving group; and p is a whole number between 1-20.

In certain embodiments, the reactive water-soluble polymer reagent is

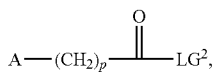

wherein A is PEG; LG² is

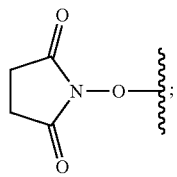 [SMILES: *ON1C(=O)CCC1=O]

and p is 1-20.

In certain embodiments, the step of contacting the thiosuccinyl-crosslinked hemoglobin with the reactive water-soluble polymer reagent, the reactive water-soluble polymer reagent and the thiosuccinyl-crosslinked hemoglobin are contacted in a molar ratio between 1:1-150:1, respectively.

In certain embodiments, the step of contacting the fumaryl-crosslinked hemoglobin with a thiol or a pharmaceutically acceptable salt or zwitterion thereof, the fumaryl-crosslinked hemoglobin and the thiol are present in a molar ratio of at least 1:1; 1:2; or 1:3.

In certain embodiments, the fumaryl-crosslinked hemoglobin and the thiol are present in a molar ratio of greater than 1:3.

In certain embodiments, the thiosuccinyl-crosslinked hemoglobin conjugate is prepared in substantially pure form.

In a fourth aspect, provided herein is a method for increasing the volume of the blood circulatory system in a subject in need thereof, wherein the method comprises transfusing into the system of the subject a therapeutically effective amount of the thiosuccinyl-crosslinked hemoglobin conjugate described herein.

In a fifth aspect, provided herein is a method for the treatment of hemorrhagic shock in a subject in need thereof, wherein the method comprises transfusing into the system of the subject a therapeutically effective amount of the thiosuccinyl-crosslinked hemoglobin conjugate described herein.

In a sixth aspect, provided herein is a method of supplying oxygen to the tissues and organs in a subject in need thereof, wherein the method comprises transfusing into the system of the subject a therapeutically effective amount of the thiosuccinyl-crosslinked hemoglobin conjugate described herein.

In a seventh aspect, provided herein is a method of treating cancer in a subject in need thereof, wherein the method comprises transfusing into the system of the subject a therapeutically effective amount of the thiosuccinyl-crosslinked hemoglobin conjugate described herein, wherein the cancer is triple-negative breast cancer or colorectal cancer.

In certain embodiments, the thiosuccinyl-crosslinked hemoglobin conjugate is substantially pure.

The thiosuccinyl-crosslinked hemoglobin conjugates described herein can have outstanding pharmacokinetics and pharmacodynamics properties, and extended in vivo circulation stability and specific organ/tissue bioavailability for different therapeutic indications. Importantly, the thiosuccinyl-crosslinked hemoglobin conjugates do not trigger a substantial immunogenic response upon repeated dosing, and do not cause any significant adverse effects, such as renal toxicity. As such, it may be more antigenically safe to administer, especially for repeated dosing and prolonged exposure.

The present disclosure also provides a method of preparing the thiosuccinyl-crosslinked hemoglobin conjugate. In certain embodiments, the method comprises the steps of 1) removing the dissolved oxygen level of the solution containing the stabilized thiosuccinyl-crosslinked hemoglobin and PEG equipped with hexanoate N-hydroxysuccinimide (NHS) ester (PEG-5K-HS) down to 0.1 mg/L, respectively; 2) mixing the stabilized thiosuccinyl-crosslinked hemoglobin solution with PEG-5K-HS under low oxygen conditions to form a pegylated thiosuccinyl-crosslinked hemoglobin under a condition in which at least 95% of the thiosuccinyl-crosslinked hemoglobin reacts with the PEG; 3) quenching the pegylation reaction and reducing the methemoglobin (MetHb) down to 5% by cysteine and 4) removing any residual PEG-5K-HS and cysteine to less than 0.2 mg/mL and 0.03% (w/w), respectively. N-acetyl cysteine (NAC) can be added at a concentration of approximately 0.05-0.2% (w/v) to further reduce the MetHb produced from the production process and also to prevent its formation during storage. The present disclosure further provides a method to prepare the thiosuccinyl-crosslinked hemoglobin conjugate in high yield and purity by, e.g., adjusting the equivalence of the PEG reagent in the conjugation reaction and the PEG spacer length.

The method of the present disclosure can be used to prepare thiosuccinyl-crosslinked hemoglobin conjugates having a p50 ranging from about 5-70 mmHg as measured at 37° C. and pH 7.4. Different levels of oxygen affinity are desirable, depending upon the intended medical application.

In the examples below, a solution containing pegylated cysteinyl-succinyl crosslinked bovine hemoglobin is produced by conjugating on average about 12-14 PEG to the cysteinyl-succinyl crosslinked bovine hemoglobin. In the conjugation step, 17 equivalents of PEG-5K-HS in 0.1 M phosphate buffer saline (PBS) at pH 7.7 is incubated with the cysteinyl-succinyl crosslinked hemoglobin (total Hemoglobin, tHb=9 g/dL) for 2 hours at room temperature under deoxygenated conditions (e.g., dissolved oxygen (DO) levels maintained below 0.1 mg/L). After the conjugation step, 77.5 mM cysteine is immediately added to the hemoglobin mixture and incubated for 16-18 hours, to quench the conjugation reaction and reduce any MetHb to 5% or less. The residual PEG and cysteine/cystine in the reaction mixture is removed by a filtration step using a 30 or 50 kDa nominal molecular weight cut off (NMWCO) membrane with acetate buffer (99 mM sodium chloride (NaCl), 46 mM sodium acetate (NaCH₃COO)) to bring the PEG and cysteine/cystine levels below 0.2 mg/mL and 0.03% (w/w), respectively.

In certain embodiments, the pharmaceutical composition comprising pegylated cysteinyl-succinyl crosslinked bovine hemoglobin produced is kept under nitrogen with the presence of 0.2% (w/v) NAC with the following product characteristics: tHb=4.5-5.5 g/dL, pH 7.4-8.4, MetHb ≤8%, endotoxin ≤0.25 EU/mL and pegylated cysteinyl-succinyl crosslinked hemoglobin in range of 95-100% purity.

BRIEF DESCRIPTION OF THE DRAWINGS

The above and other objects and features of the present disclosure will become apparent from the following description of the disclosure, when taken in conjunction with the accompanying drawings.

DETAILED DESCRIPTION

Definitions

Figure 1:
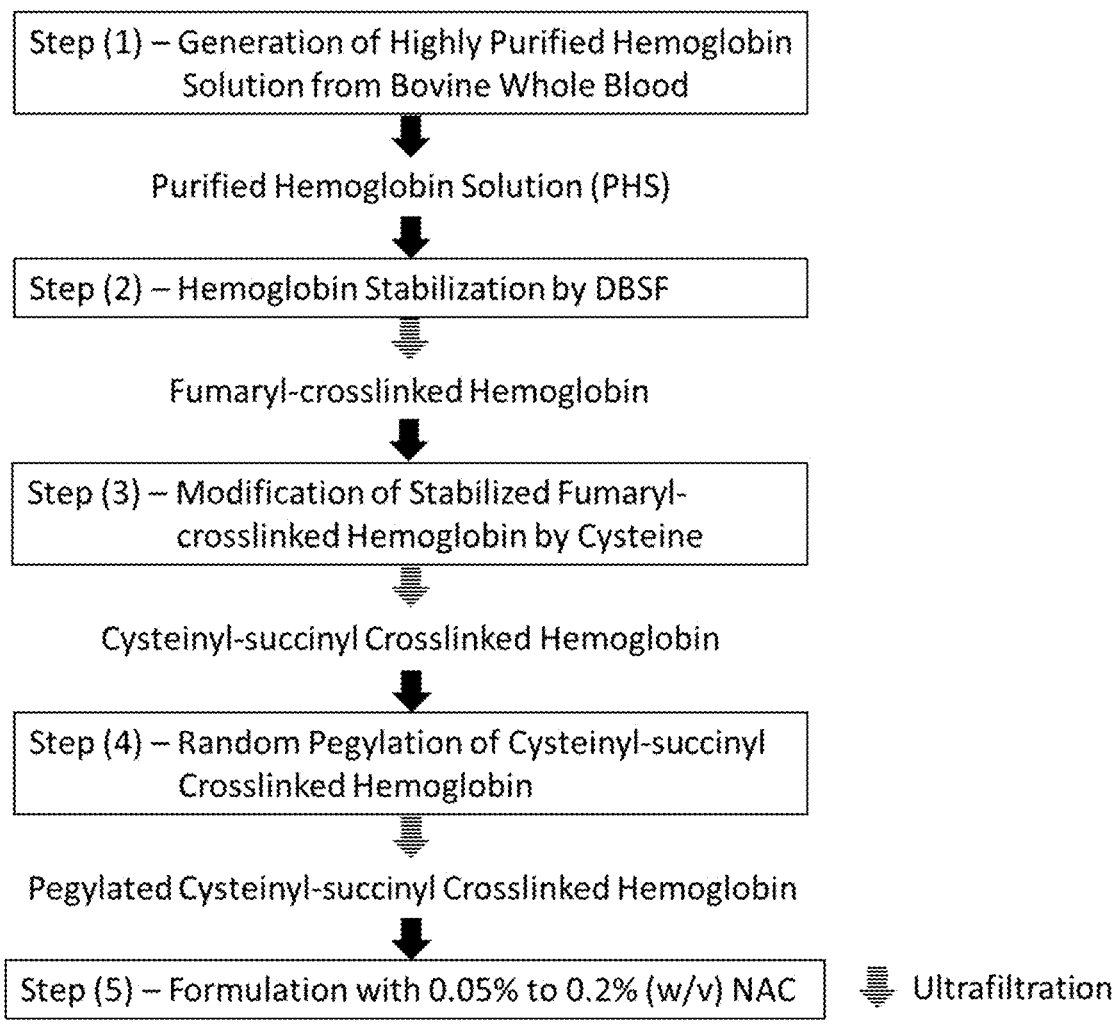
FIG. 1 is a flow-chart depicting the method of formation of pegylated cysteinyl-succinyl crosslinked hemoglobin.

The following terms shall be used to describe the present invention. In the absence of a specific definition set forth herein, the terms used to describe the present invention shall be given their common meaning as understood by those of ordinary skill in the art.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

As used herein, the terms "treat", "treating", "treatment", and the like refer to reducing or ameliorating a disorder/disease and/or symptoms associated therewith. It will be appreciated, although not precluded, treating a disorder or condition does not require that the disorder, condition, or symptoms associated therewith be completely eliminated. In certain embodiments, treatment includes prevention of a disorder or condition, and/or symptoms associated therewith. The term "prevention" or "prevent" as used herein refers to any action that inhibits or at least delays the development of a disorder, condition, or symptoms associated therewith. Prevention can include primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "subject" as used herein, refers to an animal, typically a mammal or a human, that will be or has been the object of treatment, observation, and/or experiment. When the term is used in conjunction with administration of a compound described herein, then the subject has been the object of treatment, observation, and/or administration of the compound described herein.

The term "therapeutically effective amount" as used herein, means that amount of the compound or pharmaceutical agent that elicits a biological and/or medicinal response in a cell culture, tissue system, subject, animal, or human that is being sought by a researcher, veterinarian, clinician, or physician, which includes alleviation of the symptoms of the disease, condition, or disorder being treated.

The term "composition" is intended to encompass a product comprising the specified ingredients in the specified amounts, as well as any product that results, directly or indirectly, from combinations of the specified ingredients in the specified amounts.

The term "pharmaceutically acceptable carrier" refers to a medium that is used to prepare a desired dosage form of a compound. A pharmaceutically acceptable carrier can include one or more solvents, diluents, or other liquid vehicles; dispersion or suspension aids; surface active agents; isotonic agents; thickening or emulsifying agents; preservatives; solid binders; lubricants; and the like. Remington's Pharmaceutical Sciences, Fifteenth Edition, E. W. Martin (Mack Publishing Co., Easton, Pa., 1975) and Handbook of Pharmaceutical Excipients, Third Edition, A. H. Kibbe ed. (American Pharmaceutical Assoc. 2000), disclose various carriers used in formulating pharmaceutical compositions and known techniques for the preparation thereof.

As used herein, unless otherwise indicated, the term "halo" or "halide" includes fluoro, chloro, bromo or iodo.

As used herein, "alkyl" refers to a straight-chain or branched saturated hydrocarbon group. Examples of alkyl groups include methyl-, ethyl-, propyl (e.g., n-propyl and isopropyl), butyl (e.g., n-butyl, iso-butyl, sec-butyl, tert-butyl), pentyl groups (e.g., 1-methylbutyl, 2-methylbutyl, iso-pentyl, tert-pentyl, 1,2-dimethylpropyl, neopentyl, and 1-ethylpropyl), hexyl groups, and the like. In various embodiments, an alkyl group can have 1 to 40 carbon atoms (i.e., C1-40 alkyl group), for example, 1-30 carbon atoms (i.e., C1-30 alkyl group). In certain embodiments, an alkyl group can have 1 to 6 carbon atoms, and can be referred to as a "lower alkyl group." Examples of lower alkyl groups include methyl, ethyl, propyl (e.g., n-propyl and isopropyl), and butyl groups (e.g., n-butyl, isobutyl, sec-butyl, tert-butyl). In certain embodiments, alkyl groups can be optionally substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., C2-40 alkenyl group), for example, 2 to 20 carbon atoms (i.e., C2-20 alkenyl group). In certain embodiments, alkenyl groups can be substituted as described herein. An alkenyl group is generally not substituted with another alkenyl group, an alkyl group, or an alkynyl group.

As used herein, "cycloalkyl" by itself or as part of another substituent means, unless otherwise stated, a monocyclic hydrocarbon having between 3-12 carbon atoms in the ring system and includes hydrogen, straight chain, branched chain, and/or cyclic substituents. Exemplary cycloalkyls include cyclopropyl, cyclobutyl, cyclopentyl, cyclohexyl, cycloheptyl, and the like.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly p-conjugated and optionally substituted as described herein.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In certain embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In certain embodiments, aryl groups can be optionally substituted. In certain embodiments, an aryl group can have one or more halogen substituents, and can be referred to as a "haloaryl" group. Perhaloaryl groups, i.e., aryl groups where all of the hydrogen atoms are replaced with halogen atoms (e.g., $-C_6F_5$), are included within the definition of "haloaryl." In certain embodiments, an aryl group is substituted with another aryl group and can be referred to as a biaryl group. Each of the aryl groups in the biaryl group can be optionally substituted.

The term "aralkyl" refers to an alkyl group substituted with an aryl group.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, IH-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In certain embodiments, heteroaryl groups can be substituted as described herein. In certain embodiments, heteroaryl groups can be optionally substituted.

The term "optionally substituted" refers to a chemical group, such as alkyl, cycloalkyl aryl, and the like, wherein one or more hydrogen may be replaced with a substituent as described herein, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, sulfonyl, sulfonamido, ketone, aldehyde, ester, heterocyclyl, aromatic or heteroaromatic moieties, $-CF_3$, $-CN$, or the like.

The term "carbocycle" is art-recognized and refers to an aromatic or non-aromatic ring in which each atom of the ring is carbon.

The term "nitro" is art-recognized and refers to $-NO_2$; the term "halogen" is art-recognized and refers to $-F$, $-Cl$, $-Br$ or $-I$; the term "sulfhydryl" is art-recognized and refers to $-SH$; the term "hydroxyl" means $-OH$; and the term "sulfonyl" and "sulfone" is art-recognized and refers to $-SO_2-$. "Halide" designates the corresponding anion of the halogens.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in J. Pharmaceutical Sciences (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In certain embodiments, organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, non-toxic ammonium, quaternary ammonium, and amine cations formed using counterions, such as halide, hydroxide, carboxylate, sulfate, phosphate, nitrate, lower alkyl sulfonate, and aryl sulfonate. Organic bases from which salts can be derived include, for example, primary, secondary, and tertiary amines, substituted amines including naturally occurring substituted amines, cyclic amines, basic ion exchange resins, and the like, such as isopropylamine, trimethylamine, diethylamine, triethylamine, tripropylamine, and ethanolamine. In certain embodiments, the pharmaceutically acceptable base addition salt is chosen from ammonium, potassium, sodium, calcium, and magnesium salts.

As used herein, the term "isolated" in connection with a compound described herein means the compound is not in a cell or organism and the compound is separated from some or all of the components that typically accompany it in a cell or organism.

As used herein, the term "substantially pure" in connection with a sample of a compound described herein means the sample contains at least 60% by weight of the compound. In certain embodiments, the sample contains at least 70% by weight of the compound; at least 75% by weight of the compound; at least 80% by weight of the compound; at least 85% by weight of the compound; at least 90% by weight of the compound; at least 95% by weight of the compound; or at least 98% by weight of the compound.

As used herein, the term "substantially stroma-free" used in connection with a sample of a compound described herein means the sample contains less than 5% by weight stroma. In certain embodiments, the samples contains less than 4% by weight stroma; less than 3% by weight stroma; less than 2% by weight stroma; less than 1% by weight stroma; less than 0.5% by weight stroma; less than 0.1% by weight stroma; less than 0.05% by weight stroma; or less than 0.01% by weight stroma.

As used herein, the term water-soluble polymer includes those water-soluble polymers that are substantially biocompatible and substantially nonimmunogenic and specifically excludes any water-soluble polymers that are not biocompatible and substantially nonimmunogenic. With respect to biocompatibility, a substance is considered substantially biocompatible if the beneficial effects associated with use of the substance alone or with another substance in connection with living tissues (e.g., administration to a patient) outweighs any deleterious effects as evaluated by a clinician, e.g., a physician. With respect to substantially nonimmunogenic, a substance is considered substantially nonimmunogenic if the intended use of the substance in vivo does not produce an undesired immune response (e.g., the formation of antibodies) or, if an immune response is produced, that such a response is not deemed clinically significant or important as evaluated by a clinician. In certain embodiments, that the water-soluble polymer described herein as well as thiosuccinyl-crosslinked hemoglobin conjugates comprising the same are substantially biocompatible and substantially nonimmunogenic.

The present disclosure provides a thiosuccinyl-crosslinked hemoglobin conjugate comprising a tetrameric hemoglobin; at least one water-soluble polymer covalently attached to the tetrameric hemoglobin via an optional linker; and at least one thiosuccinyl crosslinking moiety of Formula 1:

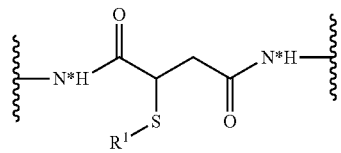

1 or a pharmaceutically acceptable salt or zwitterion thereof, wherein each N* independently represents a nitrogen selected from the group consisting of a nitrogen in a lysine residue side chain in the tetrameric hemoglobin and a nitrogen at a N-terminus in the tetrameric hemoglobin; and $R^1$ is alkyl, alkenyl, cycloalkyl, heterocycloalkyl, aryl, aralkyl, heteroaryl, or $-(CR_2)_nY$, wherein n is an integer number selected from 0-10;

R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S;

Y is selected from the group consisting of $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, $-(NR^4)S(O)_2OR^4$, and $-(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; $R^3$ is hydrogen, alkyl, aralkyl, cycloalkyl, heterocycloalkyl, aryl, heteroaryl, $OR^4$, $SR^4$, $N(R^4)_2$, $-(C=O)R^4$, $-(C=O)OR^4$, $-O(C=O)R^4$, $-O(C=O)OR^4$, $-(C=O)N(R^4)_2$, $-(NR^4)(C=O)R^4$, $-(NR^4)(C=O)OR^4$, $-O(C=O)N(R^4)_2$, $-O(C=NR^4)N(R^4)_2$, $-(NR^4)(C=O)N(R^4)_2$, $-(C=NR^4)N(R^4)_2$, $-(NR^4)(C=NR^4)N(R^4)_2$, $-(S=O)R^4$, $-S(O)_2R^4$, $-S(O)_2OR^4$, $-S(O)_2N(R^4)_2$, $-OS(O)_2R^4$, $-(NR^4)S(O)_2R^4$, $-OS(O)_2OR^4$, $-OS(O)_2N(R^4)_2$, $-(NR^4)S(O)_2N(R^4)_2$, or $-(NR^4)S(O)_2OR^4$; and $R^4$ for each instance is independently selected from the group consisting of hydrogen, alkyl, aralkyl, cycloalkyl, heterocycloalkyl, aryl, and heteroaryl; or $R^1$ is a moiety selected from the group consisting of:

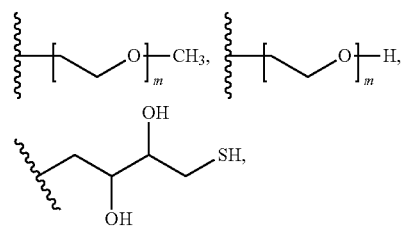

and $N^5$-(1-((carboxymethyl)amino)-1-oxo-$3\lambda^3$-propan-2-yl) glutamine or a pharmaceutically acceptable salt thereof, wherein m is a whole number selected from 1-1,000.

The water-soluble polymer may be a saccharide (e.g., a dextran, an amylose, a hyaluronic acid, a poly(sialic acid), a heparan, a heparin, etc.); a poly(amino acid), e.g., a polyaspartic acid and a polyglutamic acid; a synthetic polymer (e.g., a polyacrylic acid, a polyether, e.g., polyethylene glycol); and copolymers and combinations thereof.

The water-soluble polymer can be a linear polymer or a branched polymer. Branched polymer backbones are generally known in the art. The branched polymer can have a central branch core moiety and a group of linear polymer chains linked to the central branch core. In certain embodiments, the central branch core is a polyol, such as glycerol, pentaerythritol, or sorbitol and one or more poly(alkylene glycol) moieties are covalently bonded to the central branch core.

In certain embodiments, the water-soluble polymer is a poly(alkylene glycol), such as a PEG, a polypropylene glycol (PPG), a copolymer of ethylene glycol and propylene glycol, and the like. The PEG can be a multi-armed PEG, a forked PEG, or a branched PEG, The PEG can be an alkoxy terminated PEG (such as methoxy-PEG) or a hydroxyl terminated PEG (hydroxy-PEG).

The water-soluble polymer can have an average molecular weight between 1,000-50,000 Daltons, 1,000-40,000 Daltons, 1,000-30,000 Daltons, 1,000-20,000 Daltons, 2,000-20,000 Daltons, 1,000-10,000 Daltons, 2,000-10,000 Daltons, 3,000-10,000 Daltons, 3,000-8,000 Daltons, 4,000-8,000 Daltons, or 4,000-6,000 Daltons. In exemplary embodiments, the water-soluble polymer has an average molecular weight of 1,000, 2,000, 5,000, 10,000, 20,000, or 40,000 Daltons.

The thiosuccinyl-crosslinked hemoglobin conjugate may comprise between 1-50, 10-50, 1-40, 10-40, 1-30, 10-30, 1-25, 10-25, 1-20, 2-20, 3-20, 4-20, 5-20 6-20, 7-20, 8-20, 9-20, 10-20, 10-19, 10-18, 10-17, 10-16, 10-15, 10-14, 10-13, 11-13, 1-15, 2-15, 3-15, 4-15, 5-15, 6-15, 7-15, 8-15, 9-15, 10-15, 11-15, 12-15, 12-14, or 12-13 water-soluble polymers. The water-soluble polymer can be the same or a mixture of different water-soluble polymers.

The water-soluble polymer can be directly attached to the tetrameric hemoglobin or attached via an optional linker. Any linker known in the art can be used to attach the water-soluble polymer to the tetrameric hemoglobin. In certain embodiments, the linker is represented by the formula: $A(CH_2)_p(C=O)^*$, $A(CH_2)_p$N-succinimide*, $A(CH_2)_p$NH*, $A(CH_2)_p$S*, $A(CH_2)_p(SO_2)^*$, $A(CH_2)_p$NH(C=O)*, $A(CH_2)_p$NH(C=S)*, $A(CH_2)_p$Ph(C=O)*, $A(CH_2)_p$Ph(*C=C(H)(CN))$, or $A(CH_2)_p$NH(C=O)CH_2^*$ as shown below:

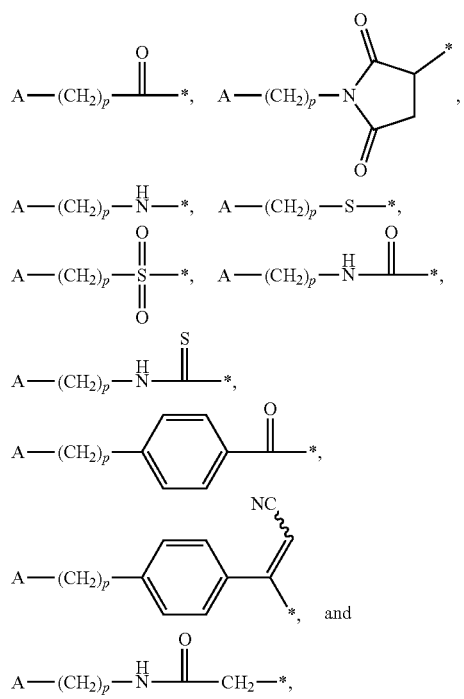

wherein A represents the water-soluble polymer, p is a whole number between 1-20, and * represents the tetrameric hemoglobin. In certain embodiments, p is a whole number between 1-18, 1-16, 1-14, 1-12, 1-10, 1-9, 2-10, 3-10, 2-9, 4-10, 5-9, 2-8, 2-6, 4-8, or 4-6. In exemplary embodiments, the linker is represented by the formula: $A(CH_2)_p(C=O)^*$, wherein p is 1-10, 1-9, 2-10, 3-10, 2-9, 4-10, 5-9, 2-8, 2-6, 4-8, or 4-6.

The water-soluble polymer can be covalently attached to the tetrameric hemoglobin via an optional linker to a nitrogen selected from the group consisting of a nitrogen in a lysine residue side chain in the tetrameric hemoglobin and a nitrogen at a N-terminus in the tetrameric hemoglobin; or the water-soluble polymer can be covalently attached to the tetrameric hemoglobin via an optional linker to a sulfur in a cysteine reside side chain in the tetrameric hemoglobin.

While the examples below are generally directed to thiosuccinyl-crosslinked hemoglobin conjugate comprising a $\alpha_2\beta_2$ tetrameric hemoglobin, other forms of hemoglobin are also contemplated by the present disclosure, such as other tetrameric hemoglobin, e.g., $\alpha_2\gamma_2$; trimeric hemoglobin, e.g., $\alpha\beta_2$, $\alpha\beta_3$, $\alpha\gamma_2$, and $\alpha_2\gamma$; dimeric hemoglobin, e.g., $\alpha\beta$ and $\alpha\gamma$; and the like; as well as polymeric forms of hemoglobin comprising one or more monomeric forms of hemoglobin; and hemoglobin derivatives that have been subjected to other methods of chemical modification including, but not limited to, methods for conjugation to polyalkylene oxide, reaction with pyridoxal phosphate, reaction with a dialdehyde, reaction with bis-diaspirin ester, reaction with iodoacetamide or other thiol-blocking reagents, or reaction in the presence of reagents such as 2,3-diphosphoglycerate (2,3-DPG) or chemically similar compounds, or genetically crosslinked hemoglobin derivatives, such as $2\alpha\beta_2$ (dialpha beta hemoglobin), wherein the dialpha moiety comprises two alpha chains that are genetically crosslinked with, e.g., a glycine linker covalently linking the N-terminus and the C-terminus of each alpha chain.

The tetrameric hemoglobin can comprise naturally occurring and/or non-naturally occurring $\alpha$, $\beta$, and $\gamma$ globin chain polypeptide sequences.

The tetrameric hemoglobin can be human hemoglobin, bovine hemoglobin, porcine hemoglobin, ovine hemoglobin, equine hemoglobin, or blood from other invertebrates and recombinant and/or transgenically produced hemoglobin.

In instances in which the tetrameric hemoglobin is human hemoglobin [e.g., comprising two $\alpha$ globin chain (UniProt Accession Number: P69905); and two $\beta$ globin chains (UniProt Accession Number: P68871)], each N* may independently represent a nitrogen present in any one or more of amino acid residues at position 1, 8, 12, 17, 41, 57, 61, 62, 91, 100, 128, and 140 of the $\alpha$ globin chains; or at position 1, 9, 18, 60, 62, 66, 67, 83, 96, 121, 133, and 145 of the $\beta$ globin chains. In certain embodiments, each N* independently represents a nitrogen present in the amino acid residues at position 100 of the $\alpha$ globin chains.

In instances in which the tetrameric hemoglobin is bovine hemoglobin [e.g., comprising two $\alpha$ globin chain (UniProt Accession Number: P01966); and two $\beta$ globin chains (UniProt Accession Number: P02070)], each N* may independently represent a nitrogen present in any one or more of amino acid residues at position 1, 8, 12, 17, 41, 57, 62, 69, 91, 100, 128, and 140 of the $\alpha$ globin chains; or at position 1, 7, 16, 18, 58, 60, 64, 65, 75, 81, 94, 103, 119, and 131 of the $\beta$ globin chains. In certain embodiments, each N* independently represents a nitrogen present in any one or more of amino acid residues and 1 and 81 of the β globin chains.

In instances in which the tetrameric hemoglobin is porcine hemoglobin [e.g., comprising two α globin chain (UniProt Accession Number: P01965); and two β globin chains (UniProt Accession Number: P02067)], each N* may independently represent a nitrogen present in any one or more of amino acid residues at position 1, 7, 11, 16, 40, 56, 61, 68, 90, 99, 127, and 139 of the α globin chains; or at position 1, 9, 18, 60, 62, 66, 67, 77, 83, 88, 133 and 145 of the β globin chains.

In certain embodiments, $R^1$ is alkyl or —$(CR_2)_nY$; or $R^1$ is a moiety selected from the group consisting of:

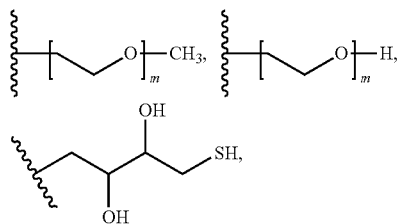

and $N^5$-(1-((carboxymethyl)amino)-1-oxo-3λ$^3$-propan-2-yl) glutamine or a pharmaceutically acceptable salt thereof, wherein m is a whole number selected from 1-1,000.

In instances in which $R^1$ is:

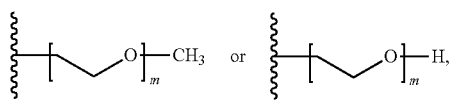

m can be 1-1,000, 1-900, 1-800, 1-700, 1-600, 1-500, 1-400, 1-300, 1-200, 1-100, 1-50, 1-25, 1-20, 1-15, 1-10, or 1-5.

In instances in which $R^1$ is —$(CR_2)_nY$, n can be 0-10, 0-9, 0-8, 0-7, 0-6, 0-5, 0-4, 0-3, 0-2, 0-1, 1-10, 1-9, 1-8, 1-7, 1-6, 1-5, 1-4, 1-3, or 1-2. In certain embodiments, each R is independently hydrogen or alkyl. In certain embodiments, $R^1$ is —$(CH_2)_nY$.

In certain embodiments, Y is —$(CRR^2R^3)$, wherein R for each instance is independently selected from the group consisting of hydrogen, alkyl, aralkyl, cycloalkyl, heterocycloalkyl, aryl, and heteroaryl; $R^2$ is hydrogen, alkyl, aralkyl, cycloalkyl, heterocycloalkyl, aryl, heteroaryl, —$N(R^4)_2$, or —$NH(C=O)R^4$; $R^3$ is hydrogen, alkyl, aralkyl, cycloalkyl, heterocycloalkyl, aryl, heteroaryl, —$CO_2R^4$, —$(C=O)NHR^4$, —$OR^4$, or —$N(R^4)_2$; and $R^4$ for each instance is independently selected from the group consisting of hydrogen, alkyl, aralkyl, cycloalkyl, heterocycloalkyl, aryl, and heteroaryl. In certain embodiments, R is hydrogen. In certain embodiments, $R^2$ is —$N(R^4)_2$ or —$NH(C=O)R^4$; and $R^3$ is —$CO_2R^4$, —$(C=O)NHR^4$, —$OR^4$, or —$N(R^4)_2$.

In certain embodiments, Y is —$(CRR^2R^3)$, wherein, R is hydrogen; $R^2$ is hydrogen, —$N(R^4)_2$, —$NH(C=O)R^4$, or —$NH(C=O)N(R^4)_2$; and $R^3$ is —$CO_2R_4$, —$(C=O)NHR^4$, —$OR^4$, or —$N(R^4)_2$.

In certain embodiments, $R^1$ is —$(CH_2)_n(CHR^2R^3)$, wherein n is 1, 2, 3, or 4; $R^2$ is —$N(R^4)_2$ or —$NH(C=O)R^4$; $R^3$ is —$CO_2R^4$ or —$(C=O)NHR^4$; and each $R^4$ is independently selected from the group consisting of hydrogen, alkyl, cycloalkyl, aryl, and heteroaryl.

In certain embodiments, $R^1$ is —$(CH_2)_n(CHR^2R^3)$, wherein n is 1, 2, 3, or 4; $R^2$ is —$N(R^4)_2$ or —$NH(C=O)R^4$; $R^3$ is —$CO_2H$; and each $R^4$ is independently selected from the group consisting of hydrogen or alkyl.

In certain embodiments, $R^1$ is selected from the group consisting of:

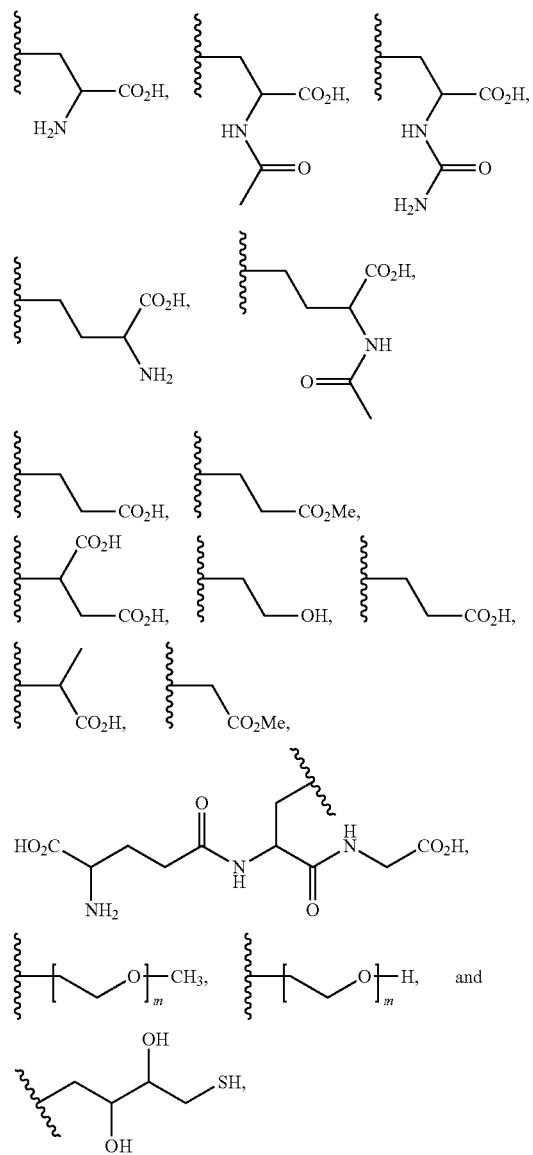

or a pharmaceutically acceptable salt of zwitterion thereof, wherein m is a whole number selected from 1-1,000.

In certain embodiments, the thiosuccinyl-crosslinked hemoglobin conjugate comprises a $α_2β_2$ tetrameric bovine hemoglobin comprising two α globin chains (UniProt Accession Number: P01966) and two β globin chains (UniProt Accession Number: P02070), wherein the β globin chains are crosslinked with at least one thiosuccinyl cross-linking moiety of Formula 1, wherein $R^1$ is selected from the group consisting of:

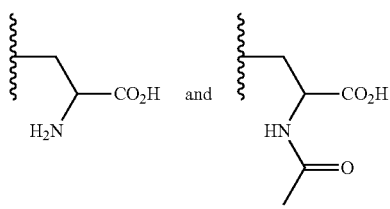

or a pharmaceutically acceptable salt or zwitterion thereof, wherein at least one N* represents the nitrogen at the N-terminus of a β globin chain and at least one N* represents the nitrogen in the lysine side chain at position 81 of a β globin chain.

In certain embodiments, the thiosuccinyl-crosslinked hemoglobin conjugate is isolated and/or substantially pure. In certain embodiments, the thiosuccinyl-crosslinked hemoglobin conjugate is substantially stroma-free.

In alternative embodiments, the present disclosure also provides analogs in which the sulfur depicted in Formula 1 is replaced with a moiety selected from the group consisting of selenium, disulfide, and diselenide, wherein $R^1$ and each N* are as defined in any one or more embodiments described herein.

The thiosuccinyl-crosslinked hemoglobin conjugate described herein and their pharmaceutically acceptable salts can be administered to a subject either alone or in combination with pharmaceutically acceptable carriers or diluents in a pharmaceutical composition according to standard pharmaceutical practice. The thiosuccinyl-crosslinked hemoglobin conjugate can be administered parenterally. Parenteral administration includes intravenous, intramuscular, intraperitoneal, subcutaneous and topical, the preferred method being intravenous administration.

Accordingly, the present disclosure provides pharmaceutically acceptable compositions, which comprise a therapeutically-effective amount of the thiosuccinyl-crosslinked hemoglobin conjugate described herein, formulated together with one or more pharmaceutically acceptable carriers (additives) and/or diluents. The pharmaceutical compositions of the present disclosure may be specially formulated for administration in liquid form, including those adapted for the following: (1) parenteral administration, for example, by intravenous as, for example, a sterile solution or suspension.

As set out herein, certain embodiments of the thiosuccinyl-crosslinked hemoglobin conjugate described herein may contain a basic functional group, such as amino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of thiosuccinyl-crosslinked hemoglobin conjugate of the present disclosure. These salts can be prepared in situ in the administration vehicle or the dosage form manufacturing process, or by separately reacting a purified thiosuccinyl-crosslinked hemoglobin conjugate of the invention in its free base form with a suitable organic or inorganic acid, and isolating the salt thus formed during subsequent purification. Representative salts include the bromide, chloride, sulfate, bisulfate, carbonate, bicarbonate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like.

The pharmaceutically acceptable salts of the compounds of the present disclosure include the conventional nontoxic salts or quaternary ammonium salts of the compounds, e.g., from nontoxic organic or inorganic acids. For example, such conventional nontoxic salts include those derived from inorganic acids such as hydrochloride, hydrobromic, sulfuric, sulfamic, phosphoric, nitric, and the like, and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the thiosuccinyl-crosslinked hemoglobin conjugate described herein may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of the thiosuccinyl-crosslinked hemoglobin conjugate of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like.

Wetting agents, emulsifiers and lubricants, such as sodium lauryl sulfate and magnesium stearate, as well as coloring agents, release agents, coating agents, sweetening, flavoring and perfuming agents, preservatives, solubilizing agents, buffers and antioxidants can also be present in the compositions.

Methods of preparing the pharmaceutical comprising the thiosuccinyl-crosslinked hemoglobin conjugate include the step of bringing into association a thiosuccinyl-crosslinked hemoglobin conjugate described herein with the carrier and, optionally, one or more accessory ingredients. In general, the formulations are prepared by uniformly and intimately bringing into association a compound described herein with liquid carriers (liquid formulation), liquid carriers followed by lyophilization (powder formulation for reconstitution with sterile water or the like), or finely divided solid carriers, or both, and then, if necessary, shaping or packaging the product.

Pharmaceutical compositions of the present disclosure suitable for parenteral administration comprise one or more thiosuccinyl-crosslinked hemoglobin conjugate described herein in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain sugars (such as sucrose), alcohols, non-ionic surfactants (such as Tween 20), antioxidants, buffers, bacteriostats, chelating agents, solutes which render the formulation isotonic with the blood of the intended recipient or suspending or thickening agents.

Examples of suitable aqueous and non-aqueous carriers which may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants, such as preservatives, wetting agents, emulsifying agents and dispersing agents. Prevention of the action of microorganisms upon the compounds of the present disclosure may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

The pharmaceutical composition may comprise between 1-10 g/dL of the thiosuccinyl-crosslinked hemoglobin conjugates. In certain embodiments, the pharmaceutical composition comprises between 1-10 g/dL; 1-9 g/dL; or 1-8 g/dL; 1-7 g/dL; 1-6 g/dL; 2-6 g/dL; 3-6 g/dL; 4-6 g/dL or 4.5-5.5 g/dL of the thiosuccinyl-crosslinked hemoglobin conjugates. In certain embodiments, the pharmaceutical composition comprises an isolated and/or substantially pure thiosuccinyl-crosslinked hemoglobin conjugate.

The concentration of the thiosuccinyl-crosslinked hemoglobin conjugates in samples described herein (in g/dL) is based solely on the mass of the thiosuccinyl-crosslinked hemoglobin content in the pharmaceutical composition and does not account for the mass of the water soluble polymers conjugated to the thiosuccinyl-crosslinked hemoglobin conjugates. The molecular weight difference arising from the weight of various numbers and types of water-soluble polymer conjugated to the thiosuccinyl-crosslinked hemoglobin conjugates does not substantially contribute to the overall mass of the thiosuccinyl-crosslinked hemoglobin. Consequently, there is a negligible difference in the thus approximated hemoglobin concentration.

In certain embodiments, the pharmaceutical composition comprises one or more thiosuccinyl-crosslinked hemoglobin conjugates selected from the group consisting of thiosuccinyl-crosslinked hemoglobin conjugates comprising one, two, and three thiosuccinyl crosslinking moieties of Formula 1. The number of different thiosuccinyl-crosslinking moieties present in the hemoglobin conjugate and their relative amounts can be readily controlled by modifying the reaction conditions of the crosslinking reaction and/or by separating undesired fumaryl-crosslinked hemoglobin crosslinking and/or thiosuccinyl-crosslinked hemoglobin thiol addition products by purification. In certain embodiments, the pharmaceutical composition comprises a thiosuccinyl-crosslinked hemoglobin conjugate having one thiosuccinyl crosslinking moiety of Formula 1; a thiosuccinyl-crosslinked hemoglobin conjugate having two thiosuccinyl crosslinking moieties of Formula 1; and a thiosuccinyl-crosslinked hemoglobin conjugate having three thiosuccinyl crosslinking moieties of Formula 1. In certain embodiments, the pharmaceutical composition comprises a thiosuccinyl-crosslinked hemoglobin conjugate having one thiosuccinyl crosslinking moiety of Formula 1; a thiosuccinyl-crosslinked hemoglobin conjugate having two thiosuccinyl crosslinking moieties of Formula 1; and a thiosuccinyl-crosslinked hemoglobin conjugate having three thiosuccinyl crosslinking moieties of Formula 1 in a mass ratio of 2.5-3.5:5.5-6.5: 0.5-1.5, respectively.

In certain embodiments, the pharmaceutical composition comprises a thiosuccinyl-crosslinked hemoglobin conjugate having one thiosuccinyl crosslinking moiety of Formula 1 at 0.1-99%; 0.1-95%; 0.1-90%; 0.1-80%; 0.1-70%; 0.1-60%; 0.1-50%; 10-50%; 20-50%; 20-40%; 25-45%; or 25-35% w/w with respect to the total weight of all of the thiosuccinyl-crosslinked hemoglobin conjugate present in the pharmaceutical composition (e.g., relative to the total weight of the thiosuccinyl-crosslinked hemoglobin conjugate having one thiosuccinyl crosslinking moiety of Formula 1; the thiosuccinyl-crosslinked hemoglobin conjugate having two thiosuccinyl crosslinking moieties of Formula 1; and the thiosuccinyl-crosslinked hemoglobin conjugate having three thiosuccinyl crosslinking moieties of Formula 1 present in the pharmaceutical composition).

In certain embodiments, the pharmaceutical composition comprises a thiosuccinyl-crosslinked hemoglobin conjugate having two thiosuccinyl crosslinking moiety of Formula 1 at 0.1-99%; 0.1-95%; 0.1-90%; 10-90%; 20-90%; 20-80%; 20-70%; 30-70%; 40-70%; 50-70%; 50-60%; or 55-65% w/w with respect to the total weight of all of the thiosuccinyl-crosslinked hemoglobin conjugates present in the pharmaceutical composition.

In certain embodiments, the pharmaceutical composition comprises a thiosuccinyl-crosslinked hemoglobin conjugate having three thiosuccinyl crosslinking moiety of Formula 1 at 0.1-99%; 0.1-95%; 0.1-90%; 0.1-80%; 0.1-70%; 0.1-60%; 0.1-50%; 0.1-40%; 0.1-30%; 0.1-20%; 5-20%; or 5-15% w/w with respect to the total weight of all of the thiosuccinyl-crosslinked hemoglobin conjugates present in the pharmaceutical composition.

The pharmaceutical composition can comprise the fumaryl crosslinked hemoglobin conjugate in less than 10%, less than 9%, less 8%, less than 7%, less than 6%, less than 5%, less than 4%, less than 3%, less than 2%, less than 1% by weight, less than 0.5%, or less than 0.1% by weight; or substantially no fumaryl crosslinked hemoglobin conjugate.

The thiosuccinyl-crosslinked hemoglobin conjugate and the fumaryl crosslinked hemoglobin conjugate may be present in the pharmaceutical composition in a mass ratio of 90:10 to 99.99:0.01. In certain embodiments, the thiosuccinyl-crosslinked hemoglobin conjugate and the fumaryl crosslinked hemoglobin conjugate may be present in the pharmaceutical composition in a mass ratio of 90:10 to 99:1; 90:10 to 98:2; 90:10 to 97:3; 90:10 to 96:4; 90:10 to 95:5; 91:9 to 95:5; 92:8 to 95:5; 93:7 to 95:5; 94:6 to 95:5; 93:7 to 97:3; 94:6 to 96:4; 91:9 to 99.99:0.01; 92:8 to 99.99:0.01; 93:7 to 99.99:0.01; 94:6 to 99.99:0.01; 95:5 to 99.99:0.01; 96:4 to 99.99:0.01; 97:3 to 99.99:0.01; 98:2 to 99.99:0.01; 99:1 to 99.99:0.01; 99.5:0.5 to 99.99:0.01; or 99.9:0.1 to 99.99:0.01, respectively. In certain embodiments, the pharmaceutical composition comprises substantially no fumaryl crosslinked hemoglobin conjugate.

In certain embodiments, the pharmaceutical composition further comprises an antioxidant. Exemplary antioxidants include, but are not limited to, cysteine, N-acetyl cysteine, γ-glutamyl-cysteine, glutathione, 2,3-dimercapto-I-propanol, 1,4-butanedithiol, sodium dithionite, other biologically compatible thiols and ascorbate. The antioxidant can inhibit or reverse the formation of methemoglobin.

In certain embodiments, the pharmaceutical composition comprises 5% (w/w) or less of the antioxidant. In certain embodiments, the pharmaceutical composition comprises 4.5% (w/w) or less; 4.0% (w/w) or less; 3.5% (w/w) or less; 3.0% (w/w) or less; 2.5% (w/w) or less; 2.0% (w/w) or less; 1.5% (w/w) or less; 1.0% (w/w) or less; 0.9% (w/w) or less; 0.8% (w/w) or less; 0.7% (w/w) or less; 0.6% (w/w) or less;

0.5% (w/w) or less; 0.4% (w/w) or less; 0.3% (w/w) or less; 0.2% (w/w) or less; or 0.1% (w/w) or less of the antioxidant. In certain embodiments, the pharmaceutical composition comprises between 0.001 to 1% (w/w); 0.01 to 1% (w/w); 0.01 to 1% (w/w); 0.01 to 0.9% (w/w); 0.01 to 0.8% (w/w); 0.01 to 0.7% (w/w); 0.01 to 0.6% (w/w); 0.01 to 0.5% (w/w); 0.01 to 0.4% (w/w); 0.01 to 0.3% (w/w); 0.05 to 0.3% (w/w); 0.1 to 0.3% (w/w); or 0.15 to 0.25% (w/w) antioxidant.

In certain embodiments, the pharmaceutical composition includes less than about 10%, 9%, 8%, 7%, 6%, 5%, 4%, 3%, 2%, 1%, 0.5%, or 0.1% by weight methemoglobin.

In certain embodiments, provided herein is a solid pharmaceutical composition comprising a thiosuccinyl-crosslinked hemoglobin conjugate as described herein, NAC, sucrose, and Tween 20.

In certain embodiments, provided herein is a pharmaceutical composition comprising a thiosuccinyl-crosslinked hemoglobin conjugate as described herein, NAC, NaCl, and NaCH$_3$COO. In certain embodiments, the pharmaceutical composition comprising a thiosuccinyl-crosslinked hemoglobin conjugate as described herein, NAC, NaCl, NaCH$_3$COO, sucrose, and Tween 20.

The present disclosure also provides methods of preparing the thiosuccinyl-crosslinked hemoglobin conjugate described herein. The thiosuccinyl-crosslinked hemoglobin can readily be prepared by any number of well-known methods known to those of ordinary skill in the art.

In certain embodiments, the method for preparing the thiosuccinyl-crosslinked hemoglobin conjugate comprises: contacting a tetrameric hemoglobin with a fumaryl cross-linking agent thereby forming a fumaryl-crosslinked hemoglobin; contacting the fumaryl-crosslinked hemoglobin with a thiol or a pharmaceutically acceptable salt or zwitterion thereof thereby forming a thiosuccinyl-crosslinked hemoglobin; and contacting the thiosuccinyl-crosslinked hemoglobin with a reactive water-soluble polymer reagent comprising a water-soluble polymer, a reactive functional group and optionally a linker, wherein the linker is covalently attached to the water-soluble polymer and the reactive functional group, thereby forming the thiosuccinyl-crosslinked hemoglobin conjugate.

Any fumaryl crosslinking agent that is capable of intramolecularly crosslinking hemoglobin known in the art can be used in the methods described herein. In certain embodiments, the fumaryl crosslinking agent can be represented by a compound of Formula 4:

4

LG$^1$—C(=O)—CH=CH—C(=O)—LG$^1$ wherein each LG$^1$ can independently be any leaving group in the art. Exemplary leaving groups include, but are not limited to, Cl, Br, I, 3,5-dibromosalicylate, salicylate, or the like.

In certain embodiments, LG$^1$ is selected from the group consisting of:

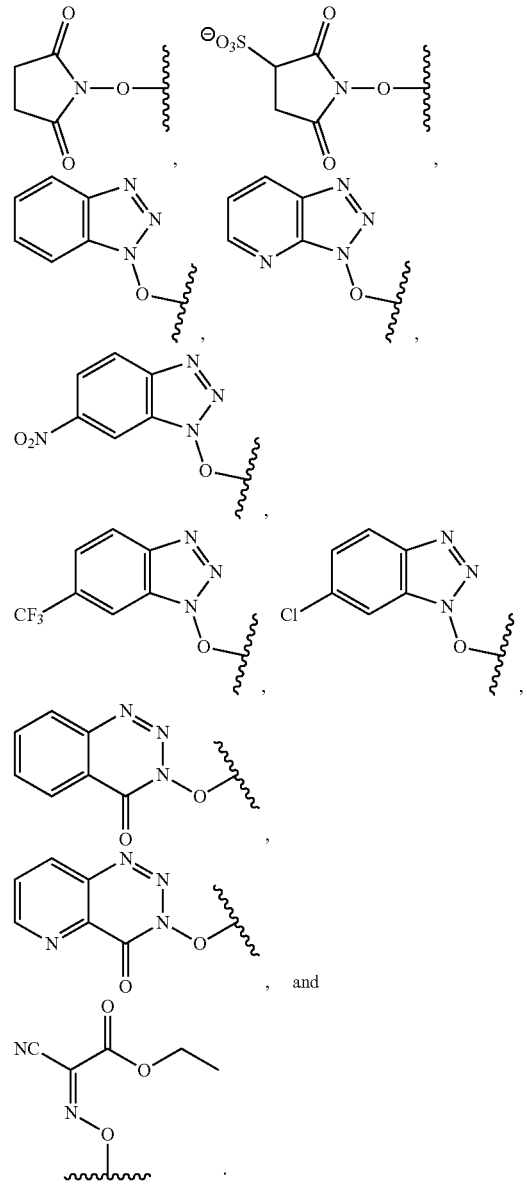

, and

The compound of Formula 4 can be performed or formed in situ, e.g., by reaction of fumaric acid with a carbonyl activating agent and optionally a coupling additive.

Exemplary carbonyl activating agents include, but are not limited to, carbodiimide, such as DCC, DIC, EDC, CIC, BMC, CPC, BDDC, PIC, PEC, and BEM, a uronium/aminium salt, such as HATU, HBTU, TATU, TBTU, HAPyU, TAPipU, HAPipU, HBPipU, HAMBU, HBMDU, HAMTU, 5,6-B(HATU), 4,5-B(HATU), HCTU, TCTU, and ACTU, phosphonium salts, such as AOP, BOP, PyAOP, PyBOP, PyOxm, PyNOP, PyFOP, NOP, and PyClock, immonium salts, such as BOMI, BDMP, BMMP, BPMP, and AOMP.

Exemplary coupling additives include, but are not limited to, HOBt. 6-NO$_2$—HOBt, 6-Cl—HOBt, 6-CF$_3$—HOBt, HOAt, HODhbt, HODhat, HOSu, and Oxyma.

In certain embodiments, the crosslinking agent is a salicyl fumarate analog, wherein the aryl ring of each of the salicyl groups is independently optionally substituted.

In certain embodiments, the crosslinking agent is selected from the group consisting of bis-3,5-dibromosalicyl fumarate (DBSF), fumaryl chloride and bis(salicyl) fumarate.

In the step of contacting the crosslinking agent and the tetrameric hemoglobin, the molar ratio of the crosslinking agent and the tetrameric hemoglobin can be between 0.8:1 to 20:1, respectively. In certain embodiments, the crosslinking agent and the tetrameric hemoglobin are present in a molar ratio between 0.8:1 to 19:1; 0.8:1 to 18:1; 0.8:1 to 17:1; 0.8:1 to 16:1; 0.8:1 to 15:1; 0.8:1 to 14:1; 0.8:1 to 13:1; 0.8:1 to 12:1; 0.8:1 to 11:1; 0.8:1 to 10:1; 0.8:1 to 9:1; 0.8:1 to 8:1; 0.8:1 to 7:1; 0.8:1 to 6:1; 0.8:1 to 5:1; 0.8:1 to 4:1; 0.8:1 to 3.5:1; 0.8:1 to 3:1; 0.8:1 to 2.5:1; 0.8:1 to 2:1; 0.8:1 to 1.5:1; 1:1 to 3:1; 1.1:1 to 3:1; 1.5:1 to 3:1; 2:1 to 3:1; or 2.25:1 to 2.75:1, respectively.

In the step of contacting the crosslinking agent and the tetrameric hemoglobin, the concentration of the tetrameric hemoglobin can be between 5-25 g/dL. In certain embodiments, the concentration of the tetrameric hemoglobin in the step of contacting the crosslinking agent and the tetrameric hemoglobin can be between 5-20 g/dL; 10-20 g/dL; 10-18 g/dL; 10-16 g/dL; 10-15 g/dL; 11-15 g/dL; 12-15 g/dL; or 13-15 g/dL.

The tetrameric hemoglobin can be reacted with the crosslinking agent in a polar protic solvent, such as in an aqueous solution. In certain embodiments, the crosslinking reaction takes place in water.

In order to facilitate the crosslinking reaction, the pH of the reaction solvent can be maintained at a pH greater than 7. In certain embodiments, the pH of the crosslinking reaction solvent has a pH between 7-10; 8-10; 8.5 to 9.5; 8.7 to 9.3; or 8.9 to 9.1.

The thus formed fumaryl-crosslinked hemoglobin can optionally purified using any method known to those skilled in the art, such as by filtration, heat-induced precipitation, centrifugation, chromatography, and the like.

The presence of oxygen in the crosslinking reaction is also known to affect the p50 value of the resulting crosslinked hemoglobin. Depending on the oxygen content in the fumaryl crosslinking reaction, the p50 value of the resulting fumaryl-crosslinked hemoglobin can have a value ranging from 5-70 mmHg.

In certain embodiments, the hemoglobin is crosslinked under oxygenated conditions, to give a fumaryl-crosslinked hemoglobin with a p50 value of 5-20 mmHg or 10-20 mmHg. In certain embodiments, the hemoglobin is crosslinked under deoxygenated conditions to give a fumaryl-crosslinked hemoglobin with a p50 value of 20-70 mmHg; 30-70 mmHg; 40-70 mmHg; 40-60 mmHg; 38-50 mmHg; 45-65 mmHg; or 55-65 mmHg.

In instances in which the hemoglobin is first thio-blocked by reaction of the hemoglobin with iodoacetamide thereby forming a thio-blocked hemoglobin; crosslinking the thus formed thio-blocked hemoglobin with a fumaryl crosslinking agent thereby forming a fumaryl-crosslinked thio-blocked hemoglobin; and contacting the fumaryl-crosslinked thio-blocked hemoglobin with a thiol or a pharmaceutically acceptable salt or zwitterion thereof thereby forming a thiosuccinyl-crosslinked thio-blocked hemoglobin, the p50 value of the resulting thiosuccinyl-crosslinked thio-blocked hemoglobin crosslinked under deoxygenated conditions can range from 15-70 mmHg; 25-50 mmHg; or 35-50 mmHg, while the p50 value of the resulting thiosuccinyl-crosslinked thio-blocked hemoglobin and thiosuccinyl-crosslinked thio-blocked hemoglobin conjugate crosslinked under oxygenated conditions can range from 5-25 mmHg; 5-15 mmHg, 5-10 mmHg or 10-15 mmHg.

The fumaryl-crosslinked hemoglobin can then reacted with the thiol thereby forming the thiosuccinyl-crosslinked hemoglobin.

The thiol can be represented by the formula $R^1SH$ as defined in any embodiment described herein.

The fumaryl-crosslinked hemoglobin can be present in the reaction with the thiol at a concentration between 5-20 g/dL. In certain embodiments, the fumaryl-crosslinked hemoglobin is present in the reaction with the thiol at a concentration between 5-18 g/dL; 5-16 g/dL; 5-14 g/dL; 5-12 g/dL; 7-12 g/dL; 8-12 g/dL; or 9-11 g/dL.

The thiol can be present in the reaction with the fumaryl-crosslinked hemoglobin at a concentration between 1-500 mM. In certain embodiments, the thiol can be present in the reaction with the fumaryl-crosslinked hemoglobin at a concentration between 1-450 mM; 1-400 mM; 1-350 mM; 1-300 mM; 1-250 mM; 1-200 mM; 1-180 mM; 1-160 mM; 1-140 mM; 1-120 mM; 1-100 mM; 10-100 mM; 20-100 mM; 30-100 mM; 30-90 mM; 40-80 mM; 77.5-310 mM, 174-310 mM, 9.7-77.5 mM; 19.4-77.5 mM; or 38.8-77.5 mM.

The reaction of the thiol and the fumaryl-crosslinked hemoglobin can be conducted at a pH between 7-11. In certain embodiments, the reaction of the thiol and the fumaryl-crosslinked hemoglobin is conducted at a pH between 7-11; 7-10; 7.4 to 10; 7.4 to 9, 7.4 to 8.2, or 8.2 to 9. The pH of the thiol addition reaction solvent can be maintained at the desired pH by use of pH buffer within the desired range or the addition of a Brønsted base to the reaction mixture, as needed. The selection of the appropriate Brønsted base or pH buffer is well within the skill of a person of ordinary skill in the art. Useful Brønsted bases include, but are not limited to Group I and Group II hydroxides, carbonates, and bicarbonates; organic amines, and the like.

The fumaryl-crosslinked hemoglobin can be reacted with the thiol in a polar protic solvent, such as in an aqueous solution. In certain embodiments, the thiol addition reaction takes place in water.

The reaction of the thiol with the fumaryl-crosslinked hemoglobin can generally conducted until all of the fumaryl-crosslinked hemoglobin starting material is converted to the desired thiosuccinyl-crosslinked hemoglobin, the fumaryl-crosslinked hemoglobin no longer is being converted to the desired thiosuccinyl-crosslinked hemoglobin, and/or the concentration of impurities and/or side products increases beyond a desired amount. Depending on the reaction conditions, the reaction of the thiol with the fumaryl-crosslinked hemoglobin can take between 1-72 hr; 6-72 hr, 12-72 hr, 24-72 hr, 36-72 hr, 48-72 hr, 60-72 hr, 12-48 hr, or 24-48 hr. In cases in which the rate of reaction of the thiol with the fumaryl-crosslinked hemoglobin is very slow (e.g., such as in the case of certain high molecular weight PEGylated thiols), the reaction of the thiol with the fumaryl-crosslinked hemoglobin can take up to one month.

The thus formed thiosuccinyl-crosslinked hemoglobin can optionally purified using any method known to those skilled in the art, such as by filtration, heat-induced precipitation, centrifugation, chromatography, and the like.

The reactive water-soluble polymer reagent can comprise any reactive functional group that is capable of covalently conjugating the water-soluble polymer and optionally the linker to hemoglobin. The reactive functional group can be any reactive functional group used for bioconjugation, such as succinimidyl ester, maleimide, 2-thiopyrridine, iodoacetamide, an arylpropionlonitrile, isocyanate, blocked isocyanate isothiocyanate, benzoyl fluoride, and the like. In certain embodiments, the reactive water-soluble polymer reagent is selected from the group consisting of:

$$A-(CH_2)_p-\overset{O}{\underset{}{C}}-LG^2, \quad A-(CH_2)_p-N\text{(maleimide)},$$

$$A-(CH_2)_p-NH_2, \quad A-(CH_2)_p-\overset{O}{\underset{O}{S}}-LG^2,$$

$$A-(CH_2)_p-NCO, \quad A-(CH_2)_p-NCS,$$

$$A-(CH_2)_p-\text{(phenyl)}-\overset{O}{C}-LG^2,$$

$$A-(CH_2)_p-\text{(phenyl)}-C\equiv C-CN,$$

$$A-(CH_2)_p-\overset{H}{N}-\overset{O}{C}-CH_2-LG^2, \text{ and}$$

$$A-(CH_2)_p-S-S-\text{(2-pyridyl)},$$

wherein A represents the water-soluble polymer; $LG^2$ is a leaving group; and p is a whole number between 1-20. In certain embodiments, p is a whole number between 1-18, 1-16, 1-14, 1-12, 1-10, 1-9, 2-10, 3-10, 2-9, 4-10, 5-9, 2-8, 2-6, 4-8, or 4-6. In exemplary embodiments, the linker is represented by the formula: $A(CH_2)_p(C=O)LG^2$, wherein p is 1-10, 1-9, 2-10, 3-10, 2-9, 4-10, 5-9, 2-8, 2-6, 4-8, or 4-6.

In certain embodiments, $LG^2$ is a leaving group selected from the group consisting of F, Cl, Br, I,

[structures: N-hydroxysuccinimide ester, sulfo-NHS ester, benzotriazole (HOBt), 7-aza-HOBt, 6-nitro-HOBt],

[structures: 6-CF3-HOBt, 6-Cl-HOBt, 3,4-dihydro-3-hydroxy-4-oxo-1,2,3-benzotriazine (HODhbt), pyrido-HODhbt, and ethyl 2-cyano-2-(hydroxyimino)acetate (Oxyma)], In certain embodiments, the reactive water-soluble polymer reagent is $$A-(CH_2)_p-\overset{O}{\underset{}{C}}-LG^2,$$

wherein A is PEG; $LG^2$ is

[N-hydroxysuccinimide structure];

and p is 1-20, 1-18, 1-16, 1-14, 1-12, 1-10, 1-9, 2-10, 3-10, 2-9, 4-10, 5-9, 2-8, 2-6, 4-8, or 4-6.

In the step of contacting the thiosuccinyl-crosslinked hemoglobin and the reactive water-soluble polymer reagent, the molar ratio of the reactive water-soluble polymer reagent and the thiosuccinyl-crosslinked hemoglobin are contacted in a molar ratio between 1:1-150:1, 1:1-100:1, 1:1-50:1, 1:1-40:1, 1:1-30:1, 5:1-30:1, 8:1-30:1, 5:1-25:1, 5:1-20:1, 10:1-20:1, 15:1-20:1, 16:1-20:1, 16:1-19:1, 16:1-18:1, respectively.

The step of contacting the reactive water-soluble polymer reagent with the thiosuccinyl-crosslinked hemoglobin can comprise combining a solution comprising the reactive water-soluble polymer reagent with the thiosuccinyl-crosslinked hemoglobin or combining the neat reactive water-soluble polymer reagent with the thiosuccinyl-crosslinked hemoglobin.

The step of contacting the reactive water-soluble polymer reagent with the thiosuccinyl-crosslinked hemoglobin can comprise combining one, two, three, four, or more portions of the reactive water-soluble polymer reagent with the thiosuccinyl-crosslinked hemoglobin.

The step of contacting the reactive water-soluble polymer reagent with the thiosuccinyl-crosslinked hemoglobin can comprise adding the reactive water-soluble polymer reagent to a solution comprising the thiosuccinyl-crosslinked hemoglobin or adding the thiosuccinyl-crosslinked hemoglobin to a solution comprising the reactive water-soluble polymer reagent.

In instances in which a solution comprising the reactive water-soluble polymer reagent is combined with the thiosuccinyl-crosslinked hemoglobin, any solvent in which the reactive water-soluble polymer reagent is at least partially soluble can be used. The selection of the appropriate solution is well within the skill of a person of ordinary skill in the art. In certain embodiments, the solution is a phosphate buffered saline aqueous solution or a saline solution.

The thiosuccinyl-crosslinked hemoglobin can be reacted with the reactive water-soluble polymer reagent in a polar protic solvent, such as in an aqueous solution. In certain embodiments, the reaction between the reactive water-soluble polymer reagent and the thiosuccinyl-crosslinked hemoglobin takes place in phosphate buffer saline aqueous solution.

The thus formed thiosuccinyl-crosslinked hemoglobin conjugate can optionally purified using any method known to those skilled in the art, such as by filtration, heat-induced precipitation, centrifugation, chromatography, and the like.

Advantageously, the p50 value of the thiosuccinyl-crosslinked hemoglobin conjugates described herein can be controlled by the reaction conditions under which the reactive water-soluble polymer reagent conjugation takes place. Depending on the oxygen content in the reactive water-soluble polymer reagent conjugation, the p50 value of the resulting thiosuccinyl-crosslinked hemoglobin conjugate can have a value ranging from 5-70 mmHg. In certain embodiments, the p50 value of the thiosuccinyl-crosslinked hemoglobin conjugate is 5-20 mmHg; 10-20 mmHg; 15-25 mmHg; 10-30 mmHg; 10-40 mmHg; 20-40 mmHg; 20-50 mmHg; 10-70 mmHg; 20-70 mmHg; 30-70 mmHg; 40-70 mmHg; 40-60 mmHg; 50-60 mmHg; 35-55 mmHg; 38-50 mmHg; 45-65 mmHg; 45-60 mmHg; or 55-65 mmHg.

Surprisingly, if the reactive water-soluble polymer reagent conjugation of the thiosuccinyl-crosslinked hemoglobin occurs under deoxygenated conditions, the p50 value of the resulting thiosuccinyl-crosslinked hemoglobin conjugate can be substantially unchanged relative to the p50 value of the unconjugated thiosuccinyl-crosslinked hemoglobin starting material. In certain embodiments, when the reactive water-soluble polymer reagent conjugation of the thiosuccinyl-crosslinked hemoglobin occurs under deoxygenated conditions, the p50 value of the resulting thiosuccinyl-crosslinked hemoglobin conjugate can be within about ±10% or less, about ±9% or less, about ±8% or less, about ±7% or less, about ±6% or less, about ±5% or less, about ±4% or less, about ±3% or less, about ±2% or less, or about ±1% or less of the p50 value of the unconjugated thiosuccinyl-crosslinked hemoglobin starting material. In certain embodiments, the p50 value of the resulting thiosuccinyl-crosslinked hemoglobin conjugate can be substantially the same as the p50 value of the thiosuccinyl-crosslinked hemoglobin. In certain embodiments, the p50 value of the thiosuccinyl-crosslinked hemoglobin conjugate can be 5-70 mmHg; 10-70 mmHg; 20-70 mmHg; 30-70 mmHg; 40-70 mmHg; 40-60 mmHg; 35-55 mmHg; 38-50 mmHg; 45-65 mmHg; 45-60 mmHg; or 55-65 mmHg.

If the reactive water-soluble polymer reagent conjugation of the thiosuccinyl-crosslinked hemoglobin occurs under oxygenated conditions, the resulting thiosuccinyl-crosslinked hemoglobin conjugate can have a p50 value about 10-20% less, about 15-20% less, about 12-18% less, or about 15% less than the p50 value of the thiosuccinyl-crosslinked hemoglobin. In certain embodiments, the p50 value of the thiosuccinyl-crosslinked hemoglobin conjugate can is 5-70 mmHg, 5-60 mmHg, 5-50 mmHg, 5-40 mmHg, 5-35 mmHg, be 5-30 mmHg, 10-70 mmHg, 10-60 mmHg, 10-50 mmHg, 10-40 mmHg, 10-35 mmHg, 5-30 mmHg, 5-20 mmHg, 15-25 mmHg, or 10-20 mmHg.

The present disclosure also provides therapeutic methods of using the thiosuccinyl-crosslinked hemoglobin conjugate described herein. The thiosuccinyl-crosslinked hemoglobin conjugate can be used in any therapeutic methods that hemoglobin based oxygen carriers can be used.

The present disclosure provides a method for increasing the volume of the blood circulatory system in a subject in need thereof, wherein the method comprises transfusing into the system of the subject a therapeutically effective amount of the thiosuccinyl-crosslinked hemoglobin conjugate according to any embodiment or combination of embodiments described herein. In certain embodiments, the subject suffers from hemorrhagic shock.

The present disclosure provides a method of supplying oxygen to the tissues and organs in a subject in need thereof, wherein the method comprises transfusing into the system of the subject a therapeutically effective amount of the thiosuccinyl-crosslinked hemoglobin conjugate according to any embodiment or combination of embodiments described herein. In certain embodiments, the subject suffers from ischemia, including for example myocardial ischemia-reperfusion injury. The ischemia can be global or regional.

The present disclosure provides a method of treating cancer in a subject in need thereof, wherein the method comprises transfusing into the system of the subject a therapeutically effective amount of the thiosuccinyl-crosslinked hemoglobin conjugate according to any embodiment or combination of embodiments described herein. The thiosuccinyl-crosslinked hemoglobin conjugate can be administered alone or in combination with one or more cancer therapeutics and/or radiotherapy to treat cancer.

In certain embodiments, the cancer is selected from the group consisting of leukemia, head and neck cancer, colorectal cancer, lung cancer, breast cancer, liver cancer, nasopharyngeal cancer, esophageal cancer and brain cancer. In certain embodiments, the cancer is triple-negative breast cancer or colorectal cancer.

The cancer therapeutic can be bortezomib, 5-fluorouracil, doxorubicin, or cisplatin.

The present disclosure also provides a method of treating systemic lupus erythematosus in a subject in need thereof, wherein the method comprises transfusing into the system of the subject a therapeutically effective amount of the thiosuccinyl-crosslinked hemoglobin conjugate according to any embodiment or combination of embodiments described herein.

The present disclosure also provides a method of treating peripheral artery disease in a subject in need thereof, wherein the method comprises transfusing into the system of the subject a therapeutically effective amount of the thiosuccinyl-crosslinked hemoglobin conjugate according to any embodiment or combination of embodiments described herein.

The present disclosure also provides a method of treating traumatic brain injury in a subject in need thereof, wherein the method comprises transfusing into the system of the subject a therapeutically effective amount of the thiosuccinyl-crosslinked hemoglobin conjugate according to any embodiment or combination of embodiments described herein.

EXAMPLES

Example 1: Preparation of Pegylated Cysteinyl-succinyl Crosslinked Hemoglobin Conjugate An exemplary schematic flow diagram of the process of making pegylated cysteinyl-crosslinked hemoglobin is illustrated in FIG. 1. The preparation steps included (1) generation of highly purified hemoglobin solution from bovine whole blood, (2) hemoglobin stabilization by crosslinking solution with bis(3,5-dibromosalicyl) fumarate (DBSF), (3) modification of fumaryl moieties in stabilized fumaryl-crosslinked hemoglobin by thiols, (4) pegylation of thiosuccinyl crosslinked hemoglobin with 5000 Molecular Weight (MW) PEG and (5) formulation of pegylated thiosuccinyl crosslinked hemoglobin with 0.05%-0.2% (w/v) NAC. In an exemplary embodiment, cysteine was used to modify the fumaryl moieties in stabilized fumaryl-crosslinked hemoglobin and pegylated cysteinyl-succinyl crosslinked hemoglobin was obtained after PEG conjugation.

In brief, bovine whole blood collected from a slaughter house was processed, lysed and purified by ultrafiltration and column chromatography steps to produce highly purified hemoglobin solution. To prevent the dissociation of the hemoglobin into heterodimers, the tetrameric hemoglobin was stabilized by crosslinking reaction with DBSF. The residual DBSF and hydrolyzed derivatives, such as 3,5-dibromosalicylic acid (DBSA) were then removed by ultrafiltration. The stabilized hemoglobin crosslinked by fumaryl bridges (fumaryl-crosslinked hemoglobin) was then modified by cysteine through 1,4-addition reaction of thiol to the fumaryl moieties present in the fumaryl-crosslinked hemoglobin to give cysteinyl-succinyl crosslinked hemoglobin. Ultrafiltration purification step was then carried out to bring the cysteine and cystine levels to below 0.03% (w/w). In the pegylation step, surface-exposed lysine residues of the cysteinyl-succinyl crosslinked hemoglobin were conjugated with PEG chains through its reaction with PEG-NHS ester (MW 5000, named as PEG-5K-HS) in PBS for 2 hours. Subsequent quenching reaction and MetHb reduction step with cysteine for 16 hours provided pegylated cysteinyl-succinyl crosslinked hemoglobin with <5% MetHb. The solution containing the above-mentioned pegylated cysteinyl-succinyl crosslinked hemoglobin was further purified by ultrafiltration to achieve PEG and cysteine levels in the purified product below 0.2 mg/mL and 0.03% (w/w), respectively. The solution containing the purified pegylated cysteinyl-succinyl crosslinked hemoglobin was formulated with NAC at a concentration of 0.05% to 0.2% (w/v), to maintain low MetHb levels (<5%) throughout long-term storage.

Example 2: Preparation of Highly Purified Bovine Hemoglobin Solution

Blood cells were separated from whole bovine blood through centrifugation and the collected blood cells were subjected to a cell washing step (Lima, M. C., 2007, Artif Cells Blood Substit Immobil Biotechnol, 35(4):431-47). Methods for the isolation and purification of hemoglobin from blood cells described in the literature can be used to prepare the hemoglobin used in the current method (Houtchens, R. A. & Rausch, C. W., 2000, U.S. Pat. No. 6,150,507; Wong, B. L. & Kwok, S. Y, 2011, U.S. Pat. No. 7,989,593 B1). The residual amount of plasma was further removed from the collected blood cells by hollow fiber filtration step. A hypotonic solution was mixed with the washed blood cells to release the intracellular hemoglobin through a tightly controlled process. The cell debris were removed from cell lysate via a 0.2 μm filtration step and followed by additional ultrafiltration steps to partially remove the impurities to form a partially purified hemoglobin solution (PHS). To further purify the PHS, the PHS was buffer exchanged to contain minimal salt concentration prior to the negative mode anion column chromatography step. The flow through fraction containing highly purified PHS was collected for which the pH, tHb and salt concentration were adjusted, sterile filtered and stored at 2-8° C. prior to the downstream process. The highly purified hemoglobin solution is *mycoplasma* free and contains very low levels of contaminants such as bovine plasma proteins (≤1 ppm), phospholipids (≤9.2 nM), residual bovine DNA (≤0.025 pg/μL) and endotoxin (≤0.1 EU/mL).

Example 3: Preparation of Cysteinyl-Succinyl Crosslinked Hemoglobin

Example 3A: Preparation of Fumaryl-Crosslinked Tetrameric Hemoglobin

The highly purified hemoglobin solution was deoxygenated to less than 0.1 mg/L dissolved oxygen level in 0.9% (w/v) aqueous NaCl solution prior to the crosslink reaction. The crosslinking reaction was carried out by incubating the deoxygenated highly purified PHS (tHb=13-15 g/dL) with 2.5 molar equivalents of DBSF at pH 9.0 for a period of 4 hours at 10-30° C. under an inert atmosphere of nitrogen (dissolved oxygen level maintained at less than 0.1 mg/L). The deoxygenated environment maintains the hemoglobin molecules in tensed state for reaction and prevents oxidation of the hemoglobin, which results in the formation of MetHb. MetHb is physiologically inactive and doesn't carry oxygen. During the crosslinking reaction, the reaction pH was maintained by the addition of deoxygenated 0.1-0.5 M NaOH aqueous solution. The reaction mixture was then purified using tangential flow filtration (TFF) system with 30 kDa NMWCO membrane. The purification was completed after undergoing 10-16 diafiltration volume (DV). The concentration of the hemoglobin solution was maintained at 9.5-10.5 g/dL through a continuous feeding of acetate buffer (99 mM NaCl, 46 mM NaCH$_3$COO, pH 8.2-8.4) into the reaction tank throughout the purification process.

Example 3B: Preparation of Cysteinyl-Succinyl Crosslinked Hemoglobin

The fumaryl moieties of the crosslinker bridges of the stabilized hemoglobin were modified by cysteine through 1,4-thiol-ene addition reaction. The reaction was carried out by the addition of 40-80 mM cysteine at pH 8.0-8.3 to fumaryl-crosslinked hemoglobin (tHb=7-10 g/dL) in acetate buffer (99 mM NaCl, 46 mM NaCH$_3$COO, pH 8.2-8.4) for a period of 15-30 hours at 10-30° C. under deoxygenated conditions for which the dissolved oxygen levels maintained below 0.1 mg/L. After the reaction, the residual cysteine/cystine in the reaction mixture was removed by a filtration step using a 30 kDa NMWCO membrane. The concentration of the hemoglobin solution was maintained at 9.5-10.5 g/dL through a continuous feeding of acetate buffer (99 mM NaCl, 46 mM NaCH$_3$COO, pH 8.2-8.4) into the reaction tank. After going through 10-16 diafiltration volume (DV), the cysteine/cystine levels in the cysteinyl-succinyl crosslinked hemoglobin solution were found below 0.03% (w/w). After cysteine modification, up to 95% of the fumaryl-crosslinked hemoglobin was modified to give cysteinyl-succinyl crosslinked hemoglobin with relatively low oxygen-carrying properties.

Example 4: Preparation of Pegylated Cysteinyl-Succinyl Crosslinked Hemoglobin

Example 4A: Optimization of Pegylation Conditions

A 5 kDa PEG chain equipped with NHS ester group (including hexanoate NHS ester (PEG-5K-HS; CH$_3$O(CH$_2$CH$_2$O)$_n$(CH$_2$)$_5$COONHS) or acetate NHS ester (PEG-5K-AS; CH$_3$O(CH$_2$CH$_2$O)$_n$(CH$_2$)COONHS) were used as model pegylation reagents to study the effect of various reaction parameters, including reactant equivalents, reaction time, spacer length, reaction medium and reaction atmosphere, on the pegylation efficiency of cysteinyl-succinyl crosslinked hemoglobin.

i) Effects of PEG Equivalent and Reaction Time

Figure 2:
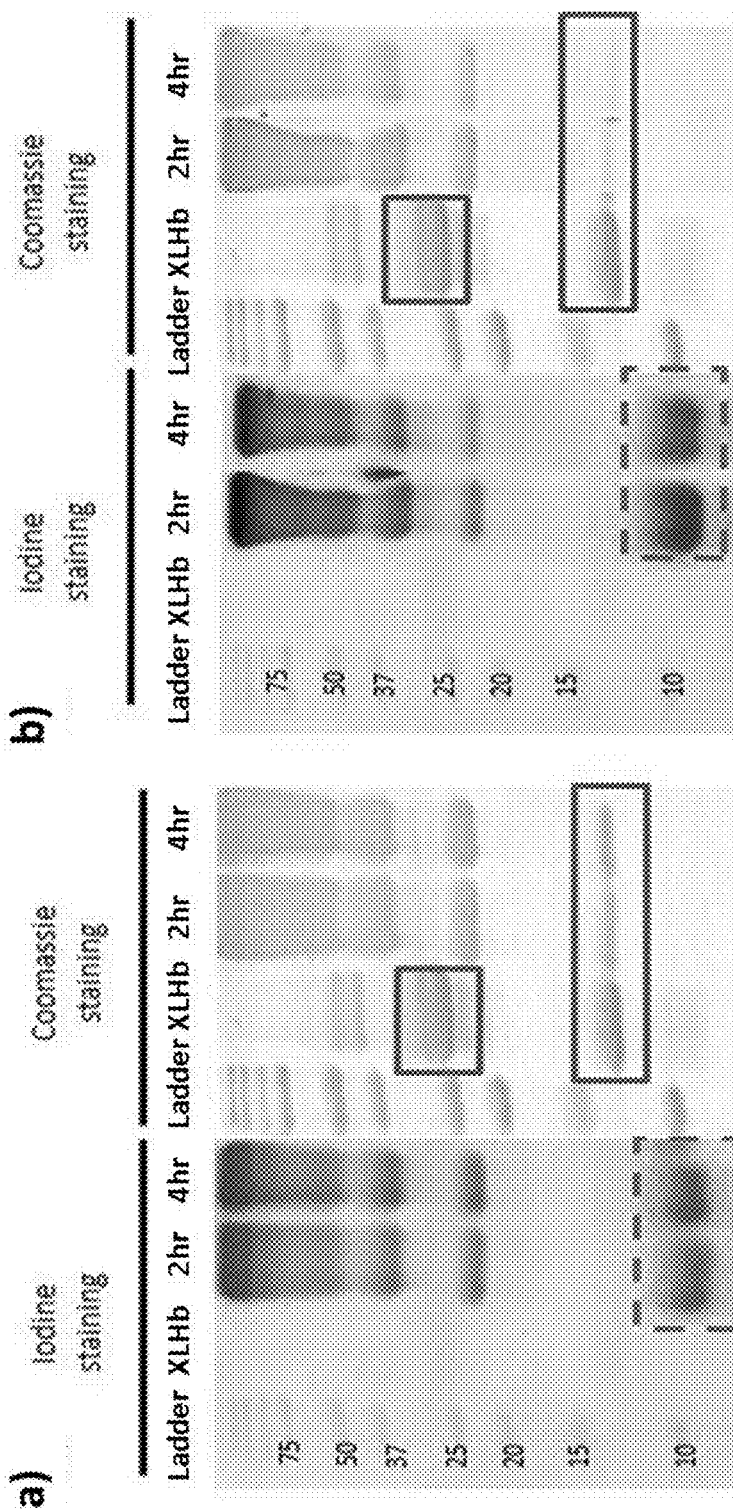
FIG. 2 shows the SDS-PAGE results for cysteinyl-succinyl crosslinked hemoglobin reacted with (a) 9 equivalents and (b) 17 equivalents of PEG-5K-HS in 0.1 M PBS (0.9 w/v % NaCl, pH=7.7) under deoxygenated environment. Residual PEG and pegylated hemoglobin were visualized by iodine staining while hemoglobin proteins were detected by Coomassie staining. Dashed line square: residual PEG; Solid line square: unpegylated hemoglobin.

The effects of reactant equivalents and reaction time were investigated using PEG-5K-HS. After the conjugation reaction of PEG-5K-HS (9 and 17 equivalents) with cysteinyl-succinyl crosslinked hemoglobin in phosphate buffer saline (PBS; 0.9 w/v % NaCl, 0.1 M sodium phosphate, pH=7.7) under deoxygenated condition for 2 hours, additional protein bands with increased molecular weight were visualized on the sodium dodecyl sulfate polyacrylamide gel electrophoresis (SDS-PAGE) gel by both iodine and Coomassie stain, as shown in FIG. 2. This suggests the successful conjugation of PEG side chains onto the cysteinyl-succinyl crosslinked hemoglobin.

Upon increasing the reaction time from 2 to 4 hours, there was no substantial change of the protein band intensity. A noticeable amount of unpegylated hemoglobin was found in the reaction mixture with the 9 equivalents reaction, as shown from the protein band at ca. 15 kDa in FIG. 2a. In contrast, the increase of PEG equivalent from 9 to 17 prominently enhanced the conjugation efficiency as indicated by the absence of unpegylated hemoglobin band (ca. 15 kDa) and concomitant increase in band intensity at higher molecular weight, as shown in FIG. 2b. These results were in agreement with the dynamic light scattering results showing that the increase of PEG equivalent from 9 to 17 increased the average hydrodynamic diameter of the pegylated hemoglobin from 12.36 to 14.27 nm. Under both conditions, the average hydrodynamic diameter of the resulting pegylated hemoglobin was almost doubled when compared to unpegylated cysteinyl-succinyl crosslinked hemoglobin (6.35 nm).

ii) Effects of PEG Spacer Length and Reaction Medium

Figure 3:
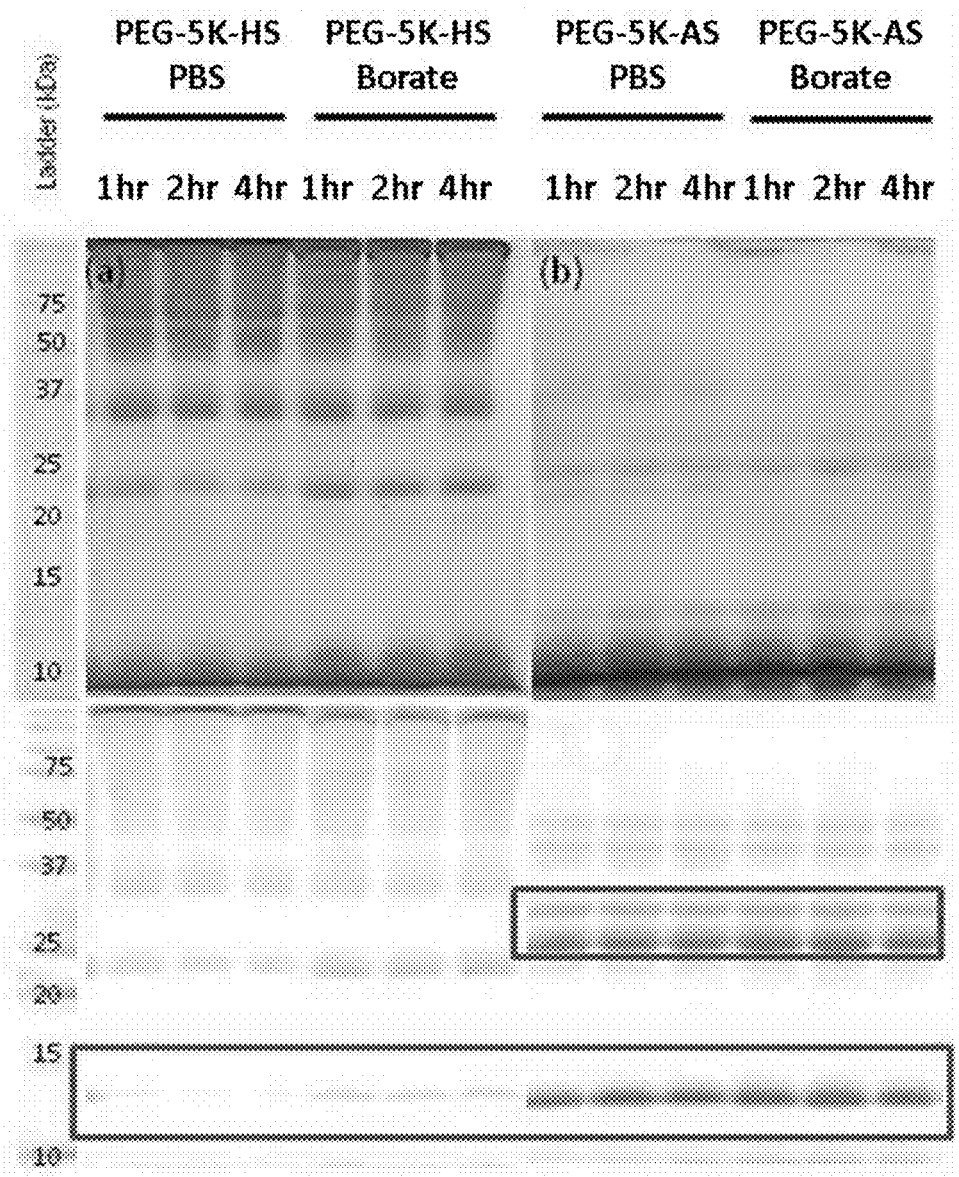
FIG. 3 shows the SDS-PAGE results for cysteinyl-succinyl crosslinked hemoglobin reacted with 17 equivalents of (a) PEG-5K-HS and (b) PEG-5K-AS under different reaction media (PBS and borate buffer) and duration (Upper: iodine staining; Lower: Coomassie staining). Solid line square: unpegylated hemoglobin.

The effect of PEG spacer length on the pegylation efficiency was investigated using PEG-5K-HS and PEG-5K-AS. The SDS-PAGE analysis of the pegylation of cysteinyl-succinyl crosslinked hemoglobin with PEG-5K-HS and PEG-5K-AS is shown in FIG. 3, respectively. Similar to the study with PEG equivalents and reaction time, PEG-5K-HS effectively attached to the cysteinyl-succinyl crosslinked hemoglobin with full consumption of monomeric hemoglobin chains, as shown in FIG. 3a. Under similar reaction conditions, limited pegylation was observed for the reaction with PEG-5K-AS and most of the crosslinked hemoglobin remained in the unpegylated form, as shown in FIG. 3b. Without wishing to be bound by thereof, it is believed that the difference can be ascribed to the increased hydrolysis rate of the NHS ester with a shorter spacer unit, leading to the deactivation of NHS under aqueous conditions, hence the loss of its conjugation ability toward the primary amine of lysine residue for conjugation.

In addition, the effect of reaction medium on the conjugation efficiency was also investigated by changing the buffer component from phosphate to borate. The pegylation efficiency of cysteinyl-succinyl crosslinked hemoglobin by PEG-5K-HS in borate buffer was found to be reduced, as indicated by the increased band intensity of unpegylated hemoglobin in SDS-PAGE, as shown in FIG. 3a. Nevertheless, compared to spacer length and reactant equivalents, the effect of reaction medium towards the pegylation efficiency was relatively minimal.

iii) Effect of Reaction Atmosphere

Hemoglobin has strong binding affinity toward oxygen and the binding of oxygen results in the conformation of relaxed state (R-state, oxygenated conditions), which may expose different subset of surface amino acids when compared to the tense state (T-state, deoxygenated conditions) in the absence of oxygen. As NHS ester mainly reacts with primary amine on the protein surface, different degree and sites of pegylation may be expected from the reactions carrying out under R- and T-state of hemoglobin, respectively. In order to examine the effect of hemoglobin state on the pegylation efficiency, the reaction shown in Example 4A (i) was repeated under oxygenated conditions.

Figure 4:
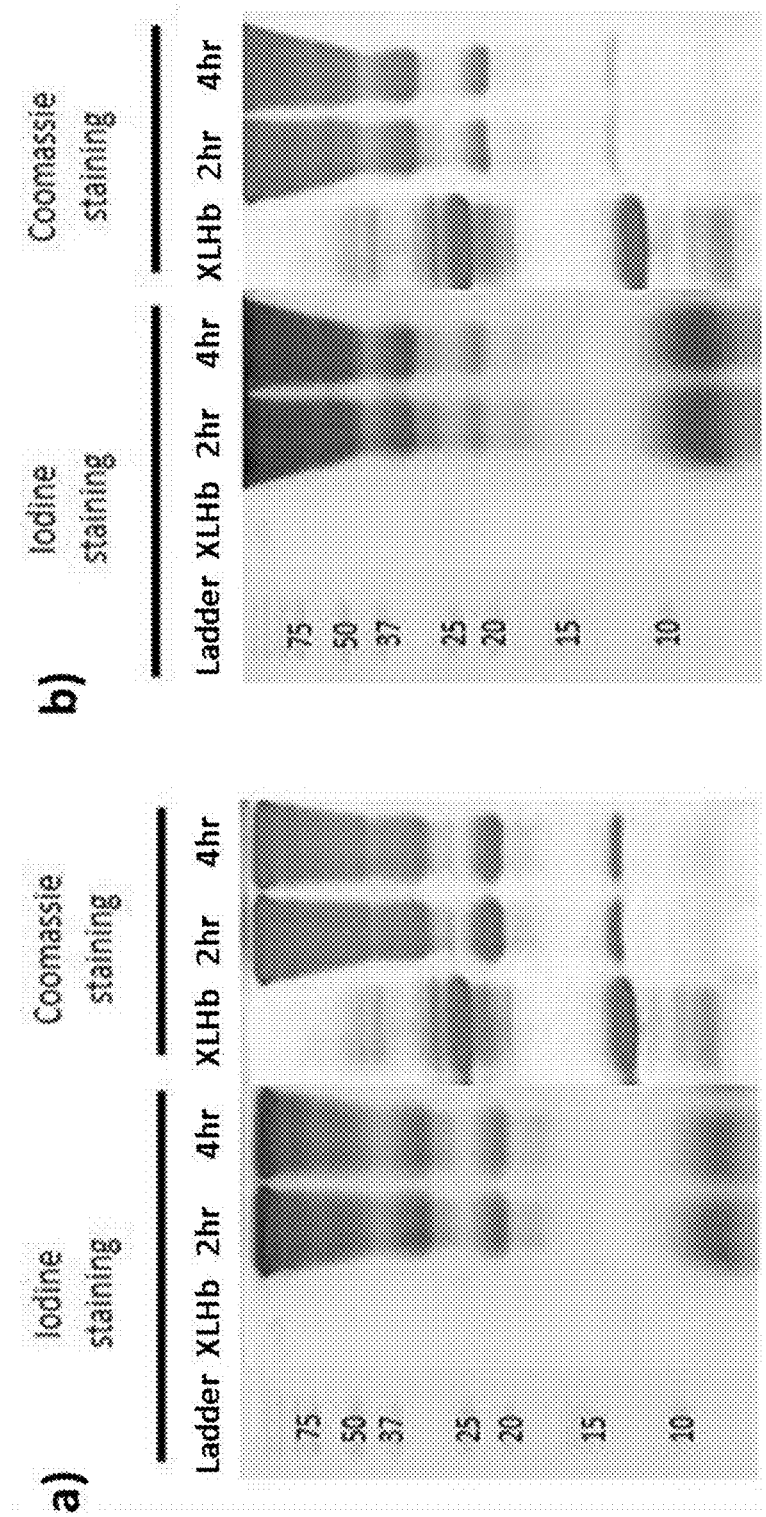
FIG. 4 shows the SDS-PAGE results for cysteinyl-succinyl crosslinked hemoglobin (XLHb) reacted with (a) 9 equivalents and (b) 17 equivalents of PEG-5K-HS under oxygenated conditions.

As shown in FIG. 4, similar SDS-PAGE patterns were obtained in the pegylation reaction of cysteinyl-succinyl crosslinked hemoglobin under oxygenated conditions, compared with those carried out under deoxygenated conditions, as shown in FIG. 2.

In general, the degree of pegylation followed a PEG-concentration dependent manner that conjugates with higher molecular weight were formed in the reaction with higher PEG equivalents, either from the reaction carried out under R- or T-state of hemoglobin. Although the efficiency of pegylation reaction under oxygenated conditions was comparable to that under deoxygenated conditions, the pegylation reaction under deoxygenated environment yielded better results. This can be attributed to the increase in MetHb levels in the reaction product, which increased from 9.1% to 22.5% after conjugation reaction with 17 equivalents of PEG-5K-HS under oxygenated conditions for 2 hours while that under deoxygenated conditions was only 15.9%, as shown in Table 1.

TABLE 1

The Change of MetHb levels in Different Reaction Steps (HS9 and HS17 = Reactions with 9 and 17 Equivalent of PEG-5K-HS, respectively).

| Conditions | PEG Equivalent | Reaction Step | MetHb [%] | O$_2$Hb [%] |
|---|---|---|---|---|
| | | Cysteinyl-succinyl Crosslinked Hemoglobin | 9.1 | 0.7 |
| Deoxygenated | HS9 | Pegylation, 2 hours | 12.3 | 0.4 |
| | | Cysteine Reduction, 16 hours | 7.0 | 1.1 |
| | HS17 | Pegylation, 2 hours | 15.9 | 0.0 |
| | | Cysteine Reduction, 16 hours | 5.8 | 0.9 |

TABLE 1-continued

The Change of MetHb levels in Different Reaction Steps (HS9 and HS17 = Reactions with 9 and 17 Equivalent of PEG-5K-HS, respectively).

| Conditions | PEG Equivalent | Reaction Step | MetHb [%] | $O_2Hb$ [%] |
|---|---|---|---|---|
| Oxygenated | HS9 | Pegylation, 2 hours | 17.8 | 74.2 |
|  |  | Cysteine Reduction, 16 hours | 12.0 | 1.5 |
|  | HS17 | Pegylation, 2 hours | 22.5 | 69.5 |
|  |  | Cysteine Reduction, 16 hours | 12.8 | 2.0 |

Nevertheless, subsequent introduction of cysteine for reaction quenching reduced the MetHb in the pegylated crosslinked hemoglobin solution to a lower level (oxygenated conditions: 12.8% and deoxygenated conditions: 5.8%, Table 1). Consequently, deoxygenated conditions were maintained throughout the production process to eliminate the repetitive oxygenation and deoxygenation steps in the production process for cost reduction and minimize MetHb impurities for quality enhancement.

Example 4B: Pegylation of Cysteinyl-Succinyl Crosslinked Hemoglobin

Figure 5:
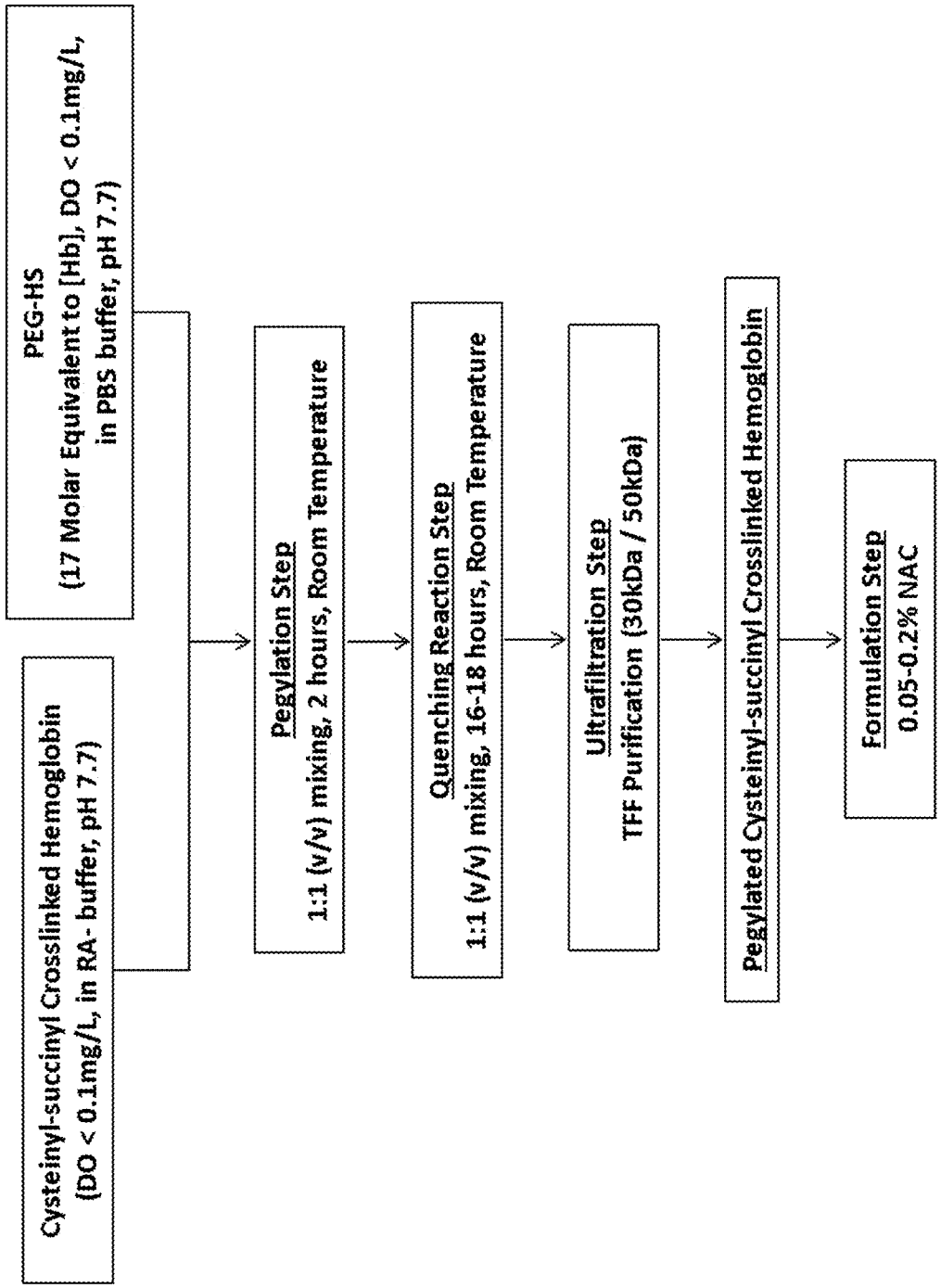
FIG. 5 is a flow-chart depicting the process of the preparation of pegylated cysteinyl-succinyl crosslinked hemoglobin.

The conditions used in the pegylation of cysteinyl-succinyl crosslinked hemoglobin prepared in Example 3 are shown in FIG. 5. Once the purified pegylated cysteinyl-succinyl crosslinked hemoglobin was prepared, the composition containing 4.5-5.5 g/dL pegylated cysteinyl-succinyl crosslinked hemoglobin was formulated with NAC with a final concentration of 0.05% to 0.2% (w/v) NAC.

In pegylation reaction, PEG-5K-HS (17 equivalents with respect to molar amount of hemoglobin) was dissolved in deoxygenated 0.1 M PBS at pH 7.7 and immediately added into an equal volume of a solution containing cysteinyl-succinyl crosslinked hemoglobin (hemoglobin content=9.0 g/dL, RA-buffer at pH 7.7) for conjugation. After reaction for 2 hours, a reducing reagent (77.5 mM cysteine) was immediately added to the hemoglobin mixture and incubated for 16-18 hours.

Apart from its reducing properties, cysteine also acts as a reaction quencher to stop the pegylation reaction by reacting with residual PEG-5K-HS. Therefore, cysteine functions not only as a reducing agent to convert the non-functional MetHb to functional hemoglobin, but also as a reaction quencher to tightly control the pegylation process for enhancing the product and process consistency.

Figure 6:
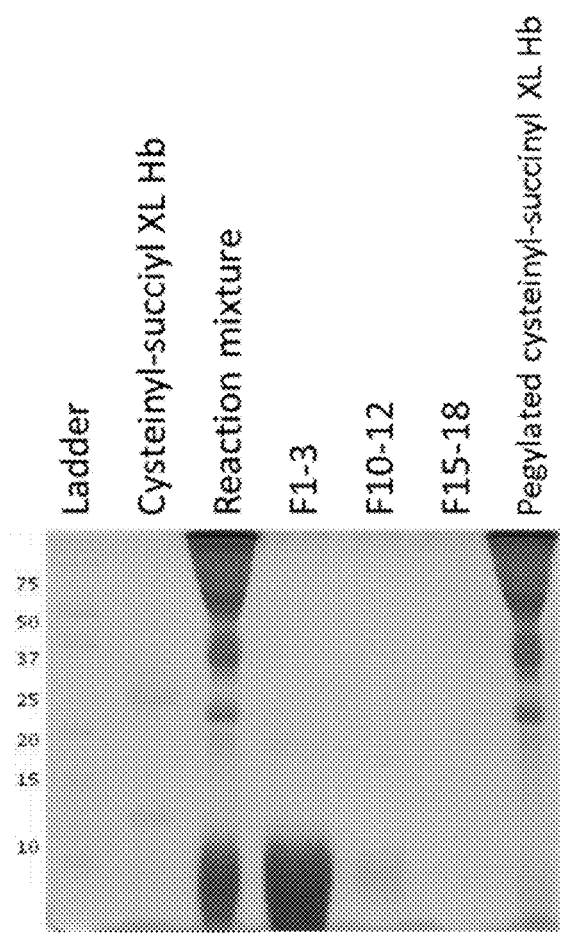
FIG. 6 shows a purification profile of the pegylated cysteinyl-succinyl crosslinked hemoglobin reaction mixture using TFF system equipped with 30 kDa NMWCO membrane (Left: iodine staining. Right: Coomassie staining; F1-F3, F10-12 and F15-18 corresponding to the combined filtrate collected from first to third diafiltration volume (DV), tenth to twelve DV and fifteen to eighteen DV, respectively).
Figure 6:
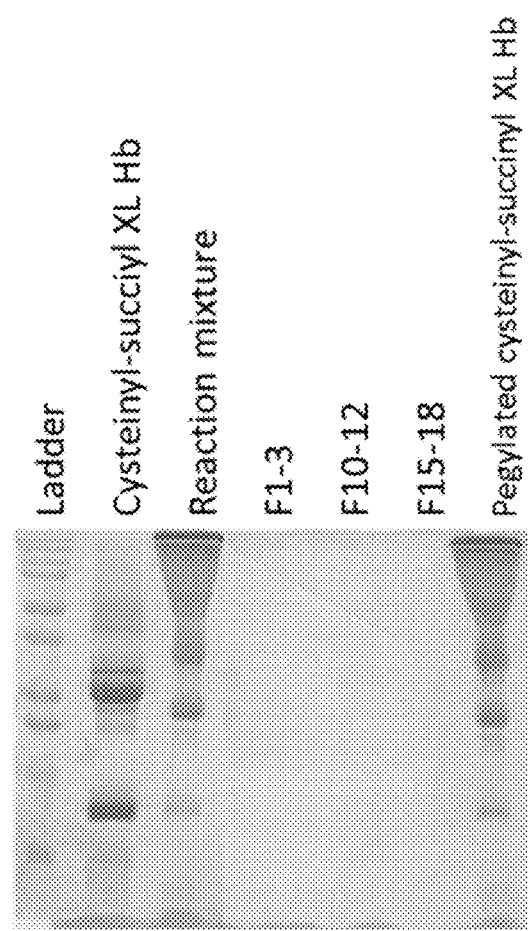

Example 4C: Purification of Pegylated Cysteinyl-Succinyl Crosslinked Hemoglobin After reaction with cysteine, the pegylated cysteinyl-succinyl crosslinked hemoglobin was purified through TFF using 30 kDa NMWCO membrane. Residual PEG was found to flow through the membrane and removed from the pegylated cysteinyl-succinyl crosslinked hemoglobin reaction mixture as undetectable level of residual PEG was revealed by SDS-PAGE, as shown in FIG. 6. After 12 DV, purified pegylated cysteinyl-succinyl crosslinked hemoglobin with free PEG and cysteine level of the mixture below 0.2 mg/mL and 0.03% (w/w), respectively, was obtained. To maintain the low MetHb level (<5%) throughout storage, NAC at a concentration of 0.05% to 0.2% (w/v) was added to the solution containing the above-mentioned purified pegylated cysteinyl-succinyl crosslinked hemoglobin.

Example 5: Purity of Pegylated Cysteinyl-Succinyl Crosslinked Hemoglobin Composition

Figure 7:
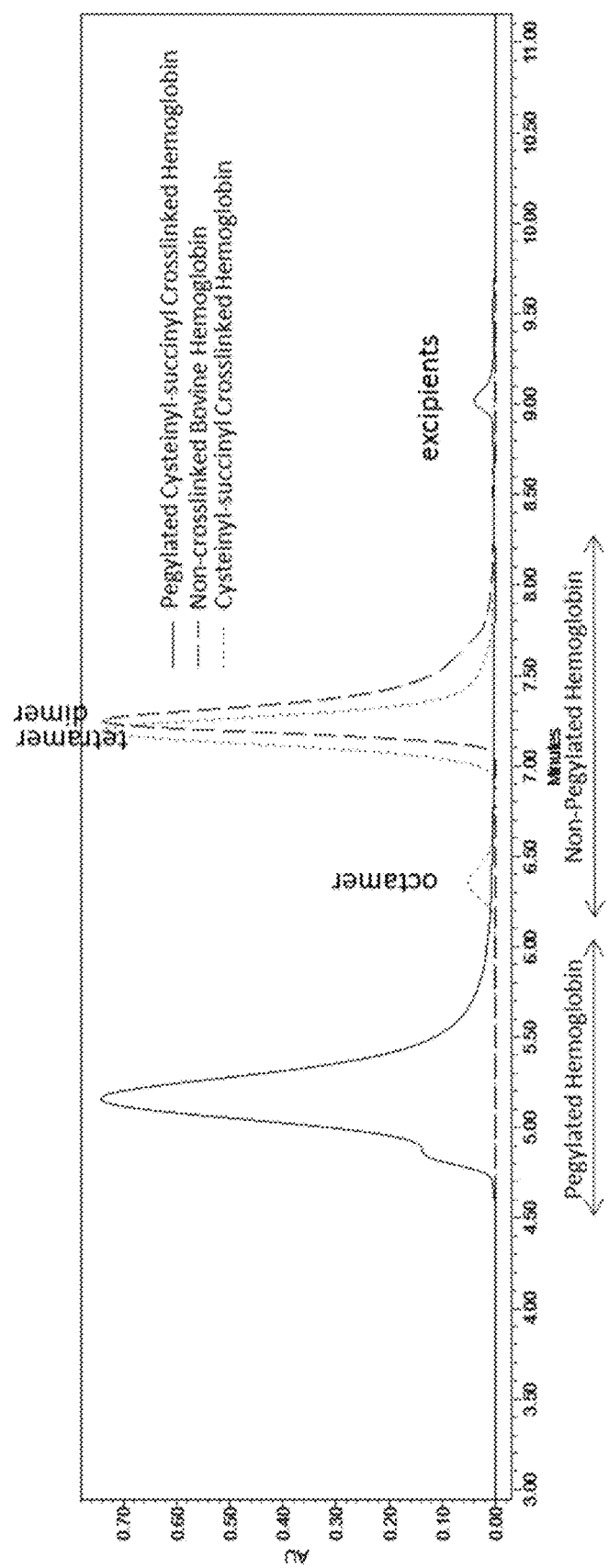
FIG. 7 is a size-exclusion chromatogram of cysteinyl-succinyl crosslinked hemoglobin (Dotted line), non-crosslinked bovine hemoglobin (Dashed line), and pegylated cysteinyl-succinyl crosslinked hemoglobin (Solid line), demonstrating confirmation of non-crosslinked hemoglobin, cysteinyl-succinyl crosslinked hemoglobin and pegylation of cysteinyl-succinyl crosslinked hemoglobin.

Example 5A: Quantification of Free Hemoglobin in Pegylated Cysteinyl-Succinyl Crosslinked Hemoglobin The amount of free hemoglobin in the pegylated cysteinyl-succinyl crosslinked hemoglobin was quantified using size-exclusion chromatography (Yarra™ 3 µm SEC-2000, LC Column 300×7.8 mm) with phosphate buffer (20 mM sodium phosphate, 0.9% NaCl, pH 6.8) as mobile phase. The proteins eluting from the column were monitored by the UV-absorption signal at 220 nm. As shown in FIG. 7, cysteinyl-succinyl crosslinked hemoglobin displayed two elution peaks corresponding to a majority of stabilized tetrameric hemoglobin (retention time: 7.20 min) with small amount of stabilized octameric hemoglobin (retention time: 6.35 min). After pegylation, the peak retention time shifted to 5.17 min with concomitant disappearance of the peaks eluted at 6.35 and 7.20 min for the cysteinyl-succinyl crosslinked hemoglobin. This suggests that the size of the crosslinked hemoglobin molecules is increased by the conjugation of PEG on the hemoglobin and at least 95% of hemoglobin was found to be covalently attached with PEG chains after conjugation process.

Example 5B: Determination of Residual PEG in the Composition of Pegylated Cysteinyl-Succinyl Crosslinked Hemoglobin After pegylation, the pegylated cysteinyl-succinyl crosslinked hemoglobin solution containing excess free PEG was further purified by TFF equipped with 30 kDa NMWCO membrane. To evaluate the residual amount of PEG, which is considered a process-related impurity, the same methodology for the estimation of the average PEG side chain per cysteinyl-succinyl crosslinked hemoglobin molecule was deployed. It was found that the pegylated cysteinyl-succinyl crosslinked hemoglobin solution contained 0.088±0.051 mg/mL residual PEG.

Example 6: Characterization of Pegylated Cysteinyl-Succinyl Crosslinked Hemoglobin The properties of pegylated cysteinyl-succinyl crosslinked hemoglobin were analyzed by different biochemical methods, as shown below.

Example 6A: Size-Exclusion Chromatography of Pegylated Cysteinyl-Succinyl Crosslinked Hemoglobin Versus Cysteinyl-Succinyl Crosslinked Hemoglobin The average PEG side chain per cysteinyl-succinyl crosslinked hemoglobin molecule and the molecular weight of pegylated cysteinyl-succinyl crosslinked hemoglobin were measured by running a reverse phase column on an Ultra Performance Liquid Chromatography (UPLC) coupled with Evaporative Light Scattering Detector (ELSD). Briefly, an Acquity™ UPLC Peptide BEH C18 column (2.1 mm×150 mm) was used to quantify the amount of free PEG in the sample. The average PEG side chain per cysteinyl-succinyl crosslinked hemoglobin molecule was calculated by subtracting the remaining amount of free PEG after 2 hours reaction from the initial PEG addition. Subsequently, the estimated molecular weight of pegylated cysteinyl-succinyl crosslinked hemoglobin was calculated by multiplying the average number of PEG side chains to the molecular weight of PEG-5K-HS (5000 Da). After the pegylation process, the average PEG side chain per cysteinyl-succinyl crosslinked hemoglobin molecule was found to be 13.22±0.72, giving an estimated molecular weight for the pegylated cysteinyl-succinyl crosslinked hemoglobin as 131±3 kDa (compared to 65 kDa for cysteinyl-succinyl crosslinked hemoglobin). The result clearly indicates that the pegylation process increased the molecular weight of the cysteinyl-succinyl crosslinked hemoglobin.

Figure 8:
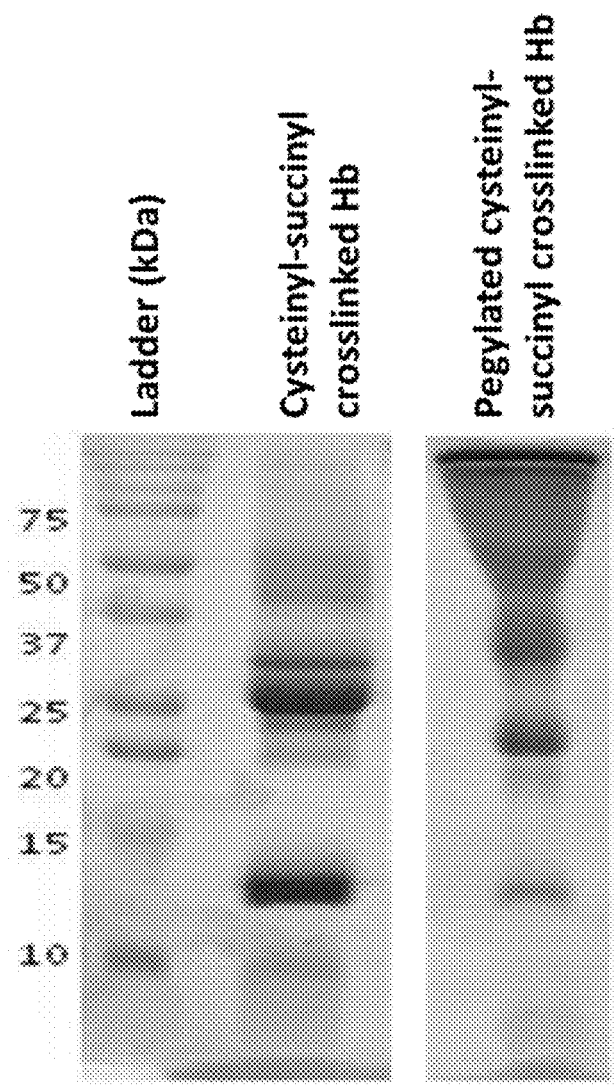
FIG. 8 shows the SDS-PAGE results for cysteinyl-succinyl crosslinked hemoglobin and pegylated cysteinyl-succinyl crosslinked hemoglobin.

Example 6B: Light Scattering and SDS-PAGE Analysis of Pegylated Cysteinyl-Succinyl Crosslinked Hemoglobin Versus Cysteinyl-Succinyl Crosslinked Hemoglobin The size of pegylated cysteinyl-succinyl crosslinked hemoglobin was also studied by measuring the hydrodynamic diameter using light scattering. Briefly, the non-invasive back scattering at 1730 was measured for the sample at 25° C. The hydrodynamic diameter increased from 6.52±0.18 nm for cysteinyl-succinyl crosslinked hemoglobin to 13.98±0.21 nm for the pegylated cysteinyl-succinyl crosslinked hemoglobin. In addition, SDS-PAGE analysis was also performed under reducing condition, as shown in FIG. 8. It is seen that the band intensity at higher molecular weight was increased when comparing pegylated cysteinyl-succinyl crosslinked hemoglobin to the unpegylated cysteinyl-succinyl crosslinked hemoglobin, which is in agreement and further supports the above findings.

Example 6C: In-Vitro Stability of Pegylated Cysteinyl-Succinyl Crosslinked Hemoglobin The stability, in terms of auto-oxidation rate (MetHb formation), for the pegylated cysteinyl-succinyl crosslinked hemoglobin, was evaluated. The initial linear formation rate of MetHb was calculated for both pegylated cysteinyl-succinyl crosslinked hemoglobin and cysteinyl-succinyl crosslinked hemoglobin, respectively. Briefly, the absorbance at 560, 576 and 630 nm were recorded every 15 minutes for 3 hours at 30° C. using a spectrometer. The following equation was used for calculating the amount of MetHb:

$$[MetHb]=(2.6828A_{630}-0.174A_{576}-0.3414A_{560})*10^{-4} \text{ Mol}$$

The amount of MetHb was plotted against time, and the slope on a linear curve fit for the first 3 hours of MetHb change was calculated. The results show that the auto-oxidation rate of pegylated cysteinyl-succinyl crosslinked hemoglobin (4.69±0.43 Met %/hr) is slightly higher than that of unpegylated cysteinyl-succinyl crosslinked hemoglobin (3.44±0.56 Met %/hr).

Figure 9:
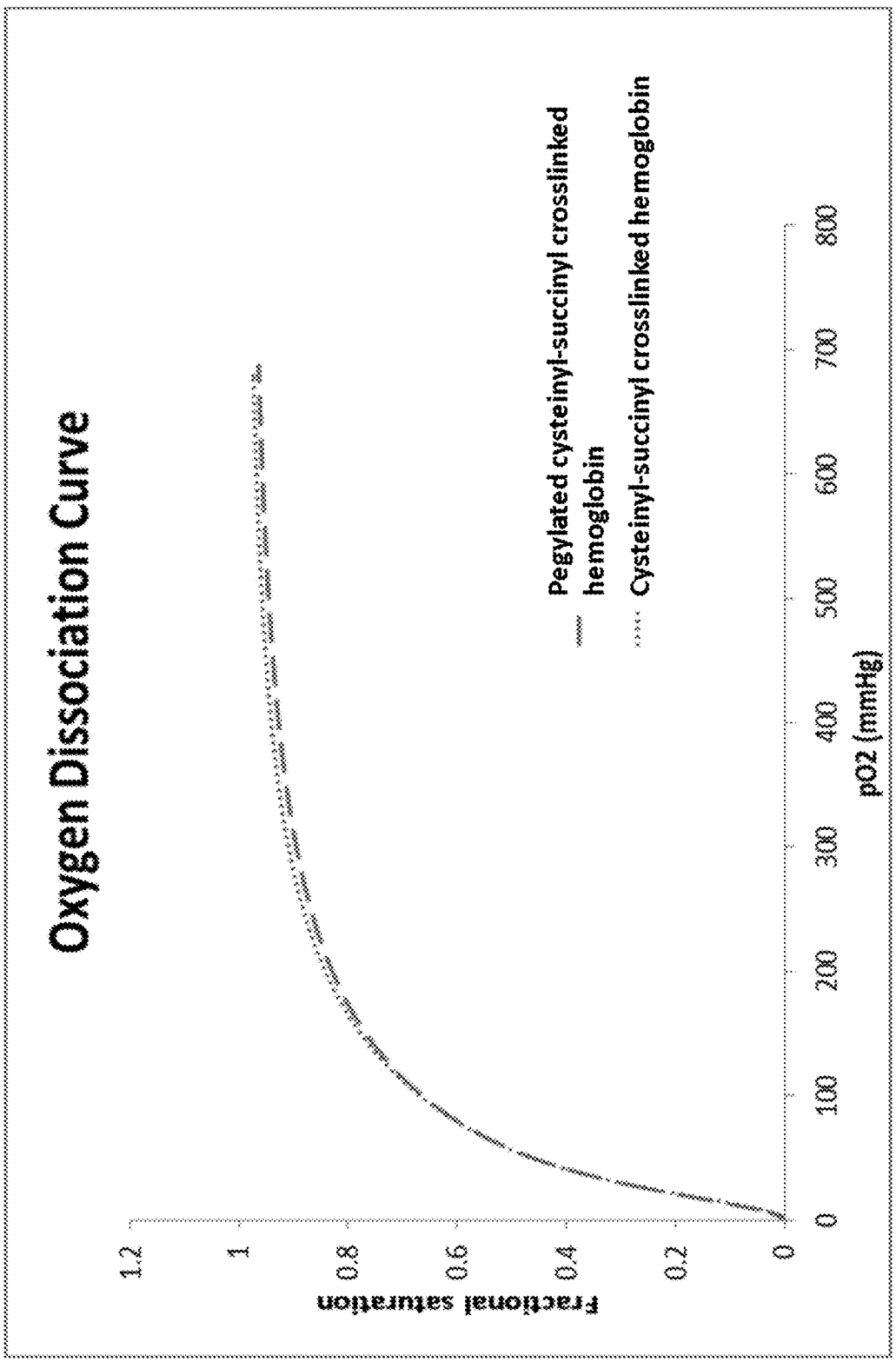
FIG. 9 shows the oxygen dissociation curves of cysteinyl-succinyl crosslinked hemoglobin and pegylated cysteinyl-succinyl crosslinked hemoglobin.

Example 6D: Oxygen Affinity Properties of Pegylated Cysteinyl-Succinyl Crosslinked Hemoglobin The oxygen affinity properties of hemoglobin can be described by its p50 value, where the fraction of hemoglobin saturated with oxygen ($O_2$) is plotted against a range of partial pressure $O_2$ ($pO_2$). p50 is defined as the $O_2$ partial pressure where 50% of the hemoglobin is saturated with $O_2$, and is often used as a descriptor of oxygen affinity. The oxygen dissociation curve for the cysteinyl-succinyl crosslinked hemoglobin and pegylated cysteinyl-succinyl crosslinked hemoglobin solution were obtained using a Hemox analyzer (TCS Scientific, New Hope, Pa.), as shown in FIG. 9. Oxygen tension was measured with a Clark oxygen electrode, and the hemoglobin saturation was measured using a built-in dual wavelength spectrophotometer. The measurement was carried out in Hemox solution (135 mM NaCl, 5 mM KCl and 30 mM TES, pH 7.4) with a final hemoglobin concentration of 0.05 g/dL and the temperature maintained at 37° C. throughout the measurement. A computer-based analysis of oxygen dissociation curve was performed yielding p50 for oxygen binding. Oxygen dissociation parameters were further derived by fitting the Adair equations to each oxygen dissociation curve by nonlinear least-squares procedure included in the Hemox analyzer software (TCS Hemox DAQ System, Version 2.0). The Adair p50 for cysteinyl-succinyl crosslinked hemoglobin and pegylated cysteinyl-succinyl-crosslinked hemoglobin is 56.40±8.12 mmHg and 53.50±8.91 mmHg, respectively. This indicates that the conditions used in the pegylation process surprisingly do not alter the oxygen affinity of the cysteinyl-succinyl crosslinked hemoglobin molecule.

It is worth mentioning that the pegylation of hemoglobin normally results in a change of oxygen binding affinity compared with its unmodified counterpart. For example, the p50 value of a PEGylated hemoglobin product Sanguinate™ is reported to be 9-14 mmHg (Abuchowski, A. et. al., 2017, US Patent 20170072023 A1), which is significantly lower than that of its parent bovine hemoglobin (24-26 mmHg). Since the use of pegylated hemoglobin as an oxygen-carrying therapeutic is undoubtedly related to its oxygen-offloading ability, the pegylation strategy described herein on the one hand can provide improved physiochemical and pharmacokinetics profiles properties to pegylated cysteinyl-succinyl crosslinked hemoglobin. On the other hand, the oxygen-binding affinity of the cysteinyl-succinyl crosslinked hemoglobin was found comparable even after pegylation and thus its therapeutic efficacy for different indications can be retained after pegylation. In this way, the p50 value of the pegylated cysteinyl-succinyl crosslinked hemoglobin can be controlled by the p50 value of the cysteinyl-succinyl crosslinked hemoglobin. To date, there are limited/no examples of pegylated hemoglobin molecules with high p50 values, particularly in the range of 30-65 mmHg. The high oxygen-offloading ability of the pegylated cysteinyl-succinyl crosslinked hemoglobin renders it as an efficient oxygen delivery agent in vivo and critical to certain clinical applications which require rapid and efficient tissue oxygen supply.

Figure 10:
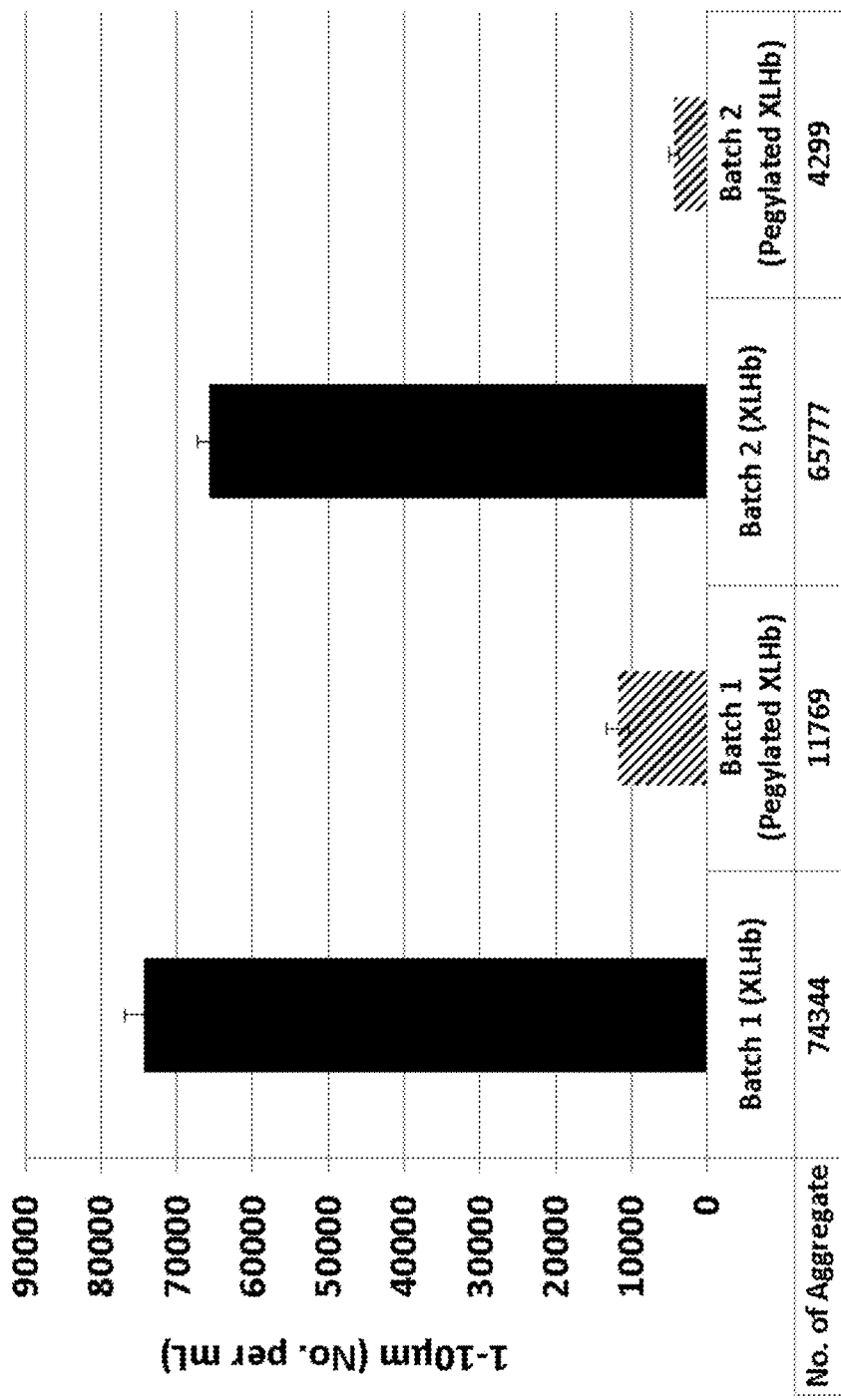
FIG. 10 shows the levels of total aggregates (1-10 μm) in cysteinyl-succinyl crosslinked hemoglobin and pegylated cysteinyl-succinyl crosslinked hemoglobin.

Example 6E: Aggregation Properties of Pegylated Cysteinyl-Succinyl Crosslinked Hemoglobin To understand the role of pegylation on aggregation properties of cysteinyl-succinyl crosslinked hemoglobin, the levels of aggregates ranging from 1-10 μm in size were measured in pegylated and unpegylated crosslinked hemoglobin by Multisizer 4e, respectively. In brief, the hemoglobin samples were taken out from the container and diluted with Isoton II Diluent at 1:1 ratio (10 mL: 10 mL) with gentle mixing. Two separate samples were prepared form each hemoglobin sample for triplicate measurement using 50 μm aperture tube, according to the instruction manual. The levels of aggregates, in term of particulate counts of 1-1.66 μm, 1.66-5 μm and 5-10 μm were added up, for comparison. The level of aggregates in the hemoglobin samples from 2 separate batches were measured, as shown in FIG. 10. The results revealed that there was a 6 to 15-fold decrease in aggregation level in cysteinyl-succinyl crosslinked hemoglobin after pegylation, implying that the aggregation quality is significantly enhanced in the pegylated cysteinyl-succinyl crosslinked hemoglobin, compared to the unpegylated ones.

Example 7: Impact of Different Polyethylene Glycol (PEG) Chain Lengths, Spacer-Arm Lengths and Pegylation Reaction Conditions on the Physiological Properties of Pegylated Cysteinyl-Succinyl Crosslinked Hemoglobin As shown from Example 6A and 6B, the pegylation of cysteinyl-succinyl crosslinked hemoglobin using PEG-5K-HS under the presented reaction conditions resulted in a significant increase of molecular weight and hydrodynamic diameter, while the oxygen affinity of the hemoglobin remained unchanged. The following study was conducted to examine the impact on pegylation efficiency, molecular weight, hydrodynamic diameter, colloid osmotic pressure (COP) and oxygen-binding affinity (p50 values), imposed by using various chain lengths, spacer-arm lengths and molar equivalents of the PEG-NHS esters in the production of pegylated cysteinyl-succinyl crosslinked hemoglobin.

Compared to the Example 4A, the focus of this study is to investigate the structural effects of PEG reagents on the properties of the resulting pegylated cysteinyl-succinyl crosslinked hemoglobin. With increased understanding about the effects of various reagents on the physiochemical properties of the pegylated cysteinyl-succinyl crosslinked hemoglobin, the developed pegylation process can potentially function as a mean to customize the properties of a pegylated hemoglobin product to fit specific pharmaceutical needs.

Figure 11:
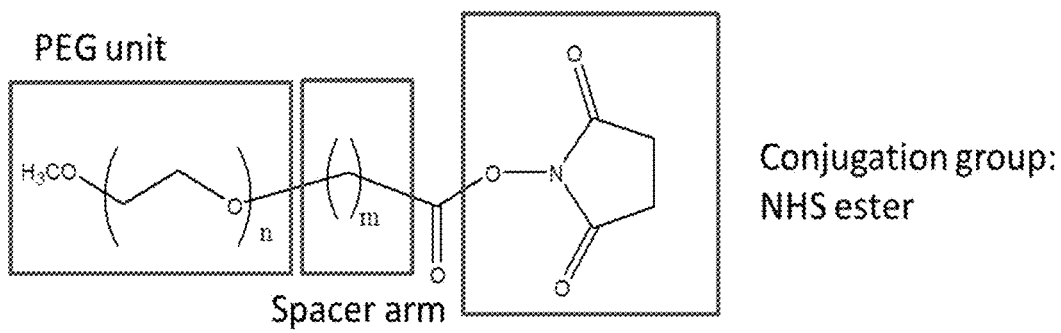
FIG. 11 depicts the structure of PEG-NHS esters used in pegylation studies.

An illustration of the PEG-NHS esters examined in this study was shown in FIG. 11.

Example 7A: Varying PEG-Chain Length to Control the Hydrodynamic Diameter

The workflow of this study is similar to that shown in FIG. 5. In general, PEG chains equipped with a hexanoate NHS ester (PEG-HS) with chain lengths of 1, 2, 5 and 10 kDa were dissolved in PBS (0.9 w/v % NaCl, 0.1 M sodium phosphate, pH=7.7, [PEG]=23.7 mM) and added to a freshly prepared cysteinyl-succinyl crosslinked hemoglobin (tHb=9.0 g/dL; 1.4 mM) under nitrogen atmosphere. Upon mixing of the two, the reaction mixture consisted of 4.5 g/dL of the hemoglobin with 17 molar equivalents of PEG-NHS ester and the reaction was allowed to proceed for 2 hours before quenching with 77.5 mM cysteine. Pegylation efficiency of the reaction was examined using reverse-phase UPLC-ELSD method, after which the reaction mixture was purified by ultrafiltration (MWCO=30 kDa) and subsequently formulated with 0.2% (w/v) NAC. The pegylated crosslinked hemoglobin was stored at 4° C. prior to characterization.

As reflected from UPLC-ELSD analysis, comparable pegylation efficiency was found across all the PEG chain lengths examined (1-10 kDa) as reflected from the similar PEG conjugation numbers (PEG:Hb=13.0-13.6) and conjugation yield (76-80%) in their reaction with cysteinyl-succinyl crosslinked hemoglobin, as shown in Table 2. In contrast, the molecular weight and hydrodynamic diameter of the pegylated crosslinked hemoglobin increased by approximately one-fold as chain length increased from 1 to 10 kDa (77 and 197 kDa; and 9.56 and 17.30 nm, respectively) and the data recorded from samples with 2 and 5 kDa chains aligned with the trends. Notably, the variation of PEG chain length imposed negligible effect toward the oxygen binding affinity of the resulting pegylated crosslinked hemoglobin, in term of Adair's p50. All these results fell within expectations as the pegylation process modified the surface exposed lysine residues or specifically primary amine from the hemoglobin. Increasing the polymer chain length would concomitantly increase the molecular weight and hydrodynamic diameter of the crosslinked hemoglobin, but the oxygen binding sites, which are present at the core of protein structures, remained unaltered.

TABLE 2

A Summary of Physical Properties and p50 Values of Cysteinyl-succinyl Crosslinked Hemoglobin Pegylated with PEG-NHS with Different Chain Lengths (1K, 2K, 5K and 10K).

|  | PEG/Hb | Pegylation Yield [%] | MW [kDa] | Hydrodynamic Diameter [nm] | Adair p50 [mmHg] |
| --- | --- | --- | --- | --- | --- |
| XLHb<sup>a</sup> | NA | NA | 64 | 6.52 ± 0.18 | 55.9 |
| PEG-1K-HS | 13.0 | 76 | 77 | 9.56 ± 0.07 | 55.1 |
| PEG-2K-HS | 13.6 | 80 | 92 | 9.95 ± 0.06 | 55.6 |
| PEG-5K-HS | 13.4 | 79 | 131 | 13.57 ± 0.08 | 52.6 |
| PEG-10K-HS | 13.3 | 78 | 197 | 17.30 ± 0.08 | 52.1 |

<sup>a</sup>cysteinyl-succinyl crosslinked hemoglobin; NA—Not Applicable

A similar study was carried out upon further expanding the PEG chain length from 10 to 40 kDa. The reactions were carried out by mixing equal volume of PEG-NHS ester ([PEG-HS]=118.6 mg/mL) and cysteinyl-succinyl crosslinked hemoglobin ([Hb]=9.0 g/dL). After reaction for 2 hours, the mixture was purified with Q-column using 50 mM Tris buffer (pH 9) with increasing NaCl content (0-0.3 M) as the elution buffer. The fractions contained pegylated cysteinyl-succinyl crosslinked hemoglobin were eluted and characterized. As shown in Table 3, although PEG-40K-HS can effectively attach to the hemoglobin with slightly lower yield, no significant difference was found for the hydrodynamic diameter of the resulting pegylated crosslinked hemoglobin. Nevertheless, these results clearly demonstrated that PEG-NHS ester with different chain lengths (from 1 kDa-40 kDa) can be effectively attached to the hemoglobin under the conditions examined. By the use of PEG-NHS ester with different PEG chain lengths, the hydrodynamic diameter of the pegylated hemoglobin can be selectively controlled and customized.

TABLE 3

A Summary of Physical Properties and p50 Values of Cysteinyl-
succinyl Crosslinked Hemoglobin Pegylated with PEG-NHS
with Different Chain Lengths (10K, 20K and 40K).

| | PEG Equivalent | PEG/Hb | Pegylation Yield [%] | MW [kDa] | Hydrodynamic Diameter [nm] | Adair p50 [mmHg] |
|---|---|---|---|---|---|---|
| XLHb[a] | NA | NA | NA | 64 | 6.52 ± 0.18 | 55.9 |
| PEG-10K-HS | 8.5 | 6.4 | 76 | 129 | 14.74 ± 0.01 | 53.5 |
| PEG-20K-HS | 4.3 | 2.8 | 66 | 121 | 14.83 ± 0.03 | 53.2 |
| PEG-40K-HS | 2.1 | 1.3 | 63 | 118 | 13.0 ± 0.02 | 56.0 |

[a]cysteinyl-succinyl crosslinked hemoglobin;
NA—Not Applicable

Example 7B: Varying Reaction Conditions to Control the COP Values

This study aims to establish a possible correlation between reaction equivalents of PEG and the COP values of the resulting pegylated crosslinked hemoglobin. In this study, pegylation reaction was conducted in a similar fashion to that shown in FIG. 5 and the cysteinyl-succinyl crosslinked hemoglobin samples were allowed to react with PEG-5K-HS under different reaction equivalents (3, 9, 13, 17 and 25). The pegylation efficiency was examined using reverse-phase UPLC-ELSD method and the COP value was measured via a colloid osmometer (OSMOMAT 050).

As shown in Table 4, an increase in reaction equivalents from 3 to 25 was directly reflected by a 9-fold increase of their corresponding product PEG:Hb ratios from 2.2 to 18.5. Notably, the pegylation efficiency across all conditions examined was found to be around 75%, suggesting that the reaction equivalent is not a determining factor toward the conjugation yield in the concentration range of PEG examined. With increasing the molar equivalents of PEG, it is expected that the conjugation number can be further increased.

Figure 12:
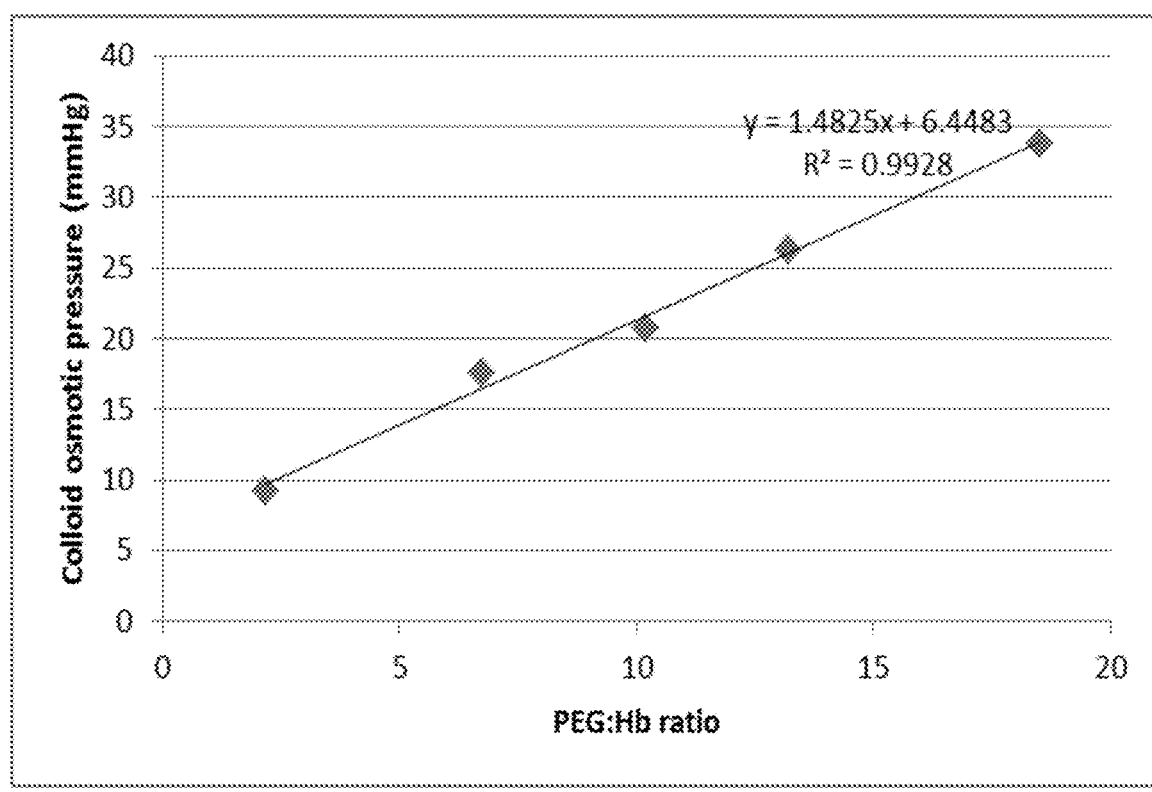
FIG. 12 shows a plot of conjugation number of pegylated hemoglobin against their corresponding COP values.

The COP of the resulting pegylated crosslinked hemoglobin are shown in Table 4. Generally, all samples with concentration of 4.5 g/dL displayed high COP values which exceeded the measurement limit of OSMOMAT 050 (i.e. 73.5 mmHg). Therefore, the samples were one-fold diluted with 0.9% NaCl and the measurement was repeated. The result revealed that the COP values of the diluted hemoglobin samples at 2.25 g/dL increased in a linear fashion when the PEG:Hb ratio is increased, as shown in Table 4 and FIG. 12. This result suggests that the COP values of pegylated crosslinked hemoglobin are mainly dependent on the number of PEG chains attached.

TABLE 4

A Summary of COP Values of Pegylated Cysteinyl-succinyl Crosslinked
Hemoglobin with Different Reaction Molar Equivalent of PEG-5K-HS.

| PEG Equivalent | PEG:Hb | Pegylation Yield [%] | COP [mmHg] @ 4.5 g/dL | COP [mmHg] @ 2.25 g/dL |
|---|---|---|---|---|
| XLHb[a] | NA | NA | 17.7 | 7.9 |
| 3 | 2.2 | 73 | 25.3 | 9.2 |
| 9 | 6.7 | 74 | 73.5[b] | 17.6 |
| 13 | 10.2 | 78 | 73.5[b] | 20.7 |
| 17 | 13.4 | 78 | 73.5[b] | 26.3 |
| 25 | 18.5 | 74 | 73.5[b] | 33.8 |

[a]cysteinyl-succinyl crosslinked hemoglobin; [b]exceed the detection limit of the osmometer.

Apart from controlling the COP value by adjusting the number of PEG chains, the COP value of the pegylated crosslinked hemoglobin was found to be regulated by varying the PEG chain length. As shown in Table 5, the attachment of short PEG chains (1 and 2 kDa) did not give rise to a significant increase to the COP values of the resulting pegylated hemoglobin. A substantial increase of the COP value of the pegylated hemoglobin has only been found upon attachment of longer PEG chains (5 and 10 kDa). In general, the COP value of pegylated hemoglobin is positively correlated to the chain length of PEG chain attached. For example, increasing the PEG chain length from 2K to 10K brought a 8-fold enhancement of the COP value from 5.5 to 43.8 mmHg (tHb=1.5 g/dL). All these results suggest that with a tight control of reaction equivalent and PEG chain length

TABLE 5

A Summary of COP Values of Cysteinyl-succinyl Crosslinked
Hemoglobin Pegylated with PEG-NHS with Different Chain
Lengths (1K, 2K, 5K and 10K, 17 molar equivalents) with
Different Chain Lengths.

| | PEG:Hb | Pegylation Yield [%] | COP [mmHg] @ 4.5 g/dL | COP [mmHg] @ 2.25 g/dL | COP [mmHg] @ 1.5 g/dL |
|---|---|---|---|---|---|
| XLHb[a] | NA | NA | 17.7 | 7.9 | 5.2 |
| PEG-1K-HS | 12.7 | 75 | 21.8 | 8.4 | 5.1 |
| PEG-2K-HS | 13.6 | 80 | 26.5 | 9.5 | 5.5 |
| PEG-5K-HS | 13.4 | 79 | 73.5[b] | 29.4 | 8.3 |
| PEG-10K-HS | 13.3 | 78 | 73.5[b] | 73.5[b] | 43.8 |

[a]cysteinyl-succinyl crosslinked hemoglobin; [b]exceeded the detection limit of the osmometer.

Example 7C: Varying Reaction Atmosphere to Control the p50 Value

Hemoglobin generally occurs in two different states, the relaxed state (R-state, oxygenated conditions), when bound to oxygen, and the tense state (T-state, deoxygenated conditions), in the absence of oxygen. As NHS ester mainly reacts with primary amines on the protein surface, different degree and sites of pegylation may be expected from the reactions carrying out under the R- and T-states of hemoglobin. In order to examine the effect of hemoglobin state on the pegylation efficiency and the properties of the resultant pegylated crosslinked hemoglobin, reactions using 17 equivalents of PEG-5K-HS were performed under oxygenated conditions using cysteinyl-succinyl crosslinked hemoglobin with two different starting p50 levels (high and low p50 values; 56 and 20 mmHg, respectively), and the results were compared with those carried out under deoxygenated conditions.

In general, the pegylation efficiency and the resultant hydrodynamic diameters for the reactions performed under oxygenated conditions were comparable to those performed under deoxygenated conditions (approximately 11-12 PEG/Hb and a hydrodynamic diameter of approximately 13-14 nm, Table 6). In contrast, the reaction atmosphere imposed a notable difference toward the oxygen binding affinity of the pegylated crosslinked hemoglobin. The results revealed that the p50 value of the pegylated cysteinyl-succinyl crosslinked hemoglobin when pegylation performed under oxygenated conditions was found to be approximately 15% lower than the corresponding unpegylated crosslinked hemoglobin (decreased from 55.9 mmHg to 42.2 mmHg for the hemoglobin with high p50 value; and from 19.5 mmHg to 15.2 mmHg for the hemoglobin with low p50 value), whereas the p50 value of the pegylated crosslinked hemoglobin when pegylation performed under deoxygenated conditions remained unchanged, as shown in Table 6. Given that the crosslink reaction is carried out in deoxygenated conditions, pegylation under deoxygenated conditions is a critical factor to maintain an unchanged oxygen affinity, regardless of the starting oxygen affinity of the unpegylated hemoglobin. In contrast, pegylation under oxygenated condition provides a mean to alter the oxygen affinity of the hemoglobin.

TABLE 6

Properties of Cysteinyl-succinyl Crosslinked Hemoglobin under Pegylation at Different Reaction Atmosphere.

| Pegylation Condition | Starting Adair p50 [mmHg] | $O_2$Hb at Pegylation [%] | PEG/Hb | MW [kDa] | Hydrodynamic Diameter [nm] | Adair p50 [mmHg] |
|---|---|---|---|---|---|---|
| Deoxygenated | 55.9 ± 0.2 | −0.4 | 11.6 | 123 | 14.4 ± 0.1 | 54.4 ± 0.1 |
| Oxygenated |  | 87.5 | 12.3 | 116 | 13.7 ± 0.1 | 42.2 ± 1.2 |
| Deoxygenated | 19.5 ± 0.3 | 6.1 | 11.7 | 123 | 14.1 ± 0.2 | 19.7 ± 1.1 |
| Oxygenated |  | 82.4 | 12.0 | 124 | 12.8 ± 0.1 | 15.2 ± 0.2 | conjugation ability toward the primary amine of lysine residues. Regardless of the PEG reagents with different spacer-arm length used, there was no obvious difference for the p50 values of all pegylated hemoglobin, suggesting that the conjugation of PEG chains with different spacer-arm length would also not affect the oxygen binding of the heme group and thus not result in a change of p50 value. In contrast, the spacer-arm length had prominent effects on the stability and reactivity of the reagents and affected the conjugation efficiency of the pegylation reaction. Studies concerning the hydrolysis rate of different PEG reagents and the reaction optimization for PEG-5K-AS have been conducted and the results were shown in Example 8A and 8C, respectively.

TABLE 7

Properties of Cysteinyl-succinyl Crosslinked Hemoglobin Pegylated with PEG with Different Spacer-arm Lengths.

|  | PEG/Hb | Pegylation Yield [%] | MW [kDa] | Hydrodynamic Diameter [nm] | Adair p50 [mmHg] |
|---|---|---|---|---|---|
| XLHb[a] | NA | NA | 64 | 6.52 ± 0.18 | 55.9 |
| PEG-5K-AS | 2.5 | 15 | 77 | 7.77 ± 0.07 | 50.4 |
| PEG-5K-PS | 12.6 | 74 | 128 | 13.16 ± 0.02 | 55.5 |
| PEG-5K-HS | 13.5 | 79 | 132 | 12.64 ± 0.08 | 52.6 |
| PEG-5K-DCS | 12.9 | 76 | 129 | 13.10 ± 0.02 | 50.5 |

[a]cysteinyl-succinyl crosslinked hemoglobin; NA—Not Applicable

Example 7D: The Reaction Studies of PEG Reagents with Variation in their Spacer-Arm Length The pegylation efficiency on using PEG with different spacer-arm lengths, including PEG-5K-AS (acetate NHS ester), PEG-5K-PS (propionate NHS ester) PEG-5K-HS (hexanoate NHS ester) and PEG-5K-DCS (decanoate NHS ester), in the reaction with 17 equivalents, were examined. As shown in Table 7, using reaction conditions as shown for PEG-5K-HS, similar pegylation efficiency and resultant hydrodynamic diameter were observed when cysteinyl-succinyl crosslinked hemoglobin was conjugated by PEG-5K-PS and PEG-5K-DCS (12.6 and 13.5 PEG/Hb with the yield >70%; hydrodynamic diameter=13.2 and 13.1 nm, respectively), whereas limited pegylation was observed for the reaction using PEG-5K-AS (2.5 PEG/Hb with 15% yield; hydrodynamic diameter=7.8 nm). Without wishing to be bound by theory, it is believed that this difference can be ascribed to the increased hydrolysis rate of the NHS ester with a shorter spacer-arm unit, leading to the deactivation of NHS under aqueous conditions and hence the loss of its Example 8: Further Optimization of Pegylation Reaction with Different PEG-NHS Esters In the above examples, the pegylation reactions with PEG-5K-HS were performed in a relatively small reaction scale (<4 L). However, depending on the chemical properties of PEG-NHS ester, the reaction conditions could be optimized to achieve maximum pegylation yield for cost reduction. In the following examples, the reactivity and stability of various PEG reagents in pegylation reaction were examined. With an understanding of the chemical properties of the PEG reagents, different optimization processes were developed as shown below.

Example 8A: Studying the Hydrolysis Rate of PEG-NHS Ester with Different Spacer-Arm Lengths This study aims to study the hydrolysis rate of PEG-NHS ester with varying spacer-arm lengths via UPLC-ELSD analysis. PEG-NHS ester losses its conjugation ability upon hydrolysis in aqueous solution to give non-reactive carboxyl-PEG (Lim, C. Y, 2014, Langmuir, 30:12868-78). Given that the retention time of active PEGs is different compared with their hydrolyzed counterparts in UPLC-ELSD analysis, monitoring the relative proportion of the active PEG-NHS ester over time gives a depiction of PEG degradation progression, thus allowing the measurement of the hydrolysis half-life of PEG-NHS ester under various reaction conditions.

Figure 13:
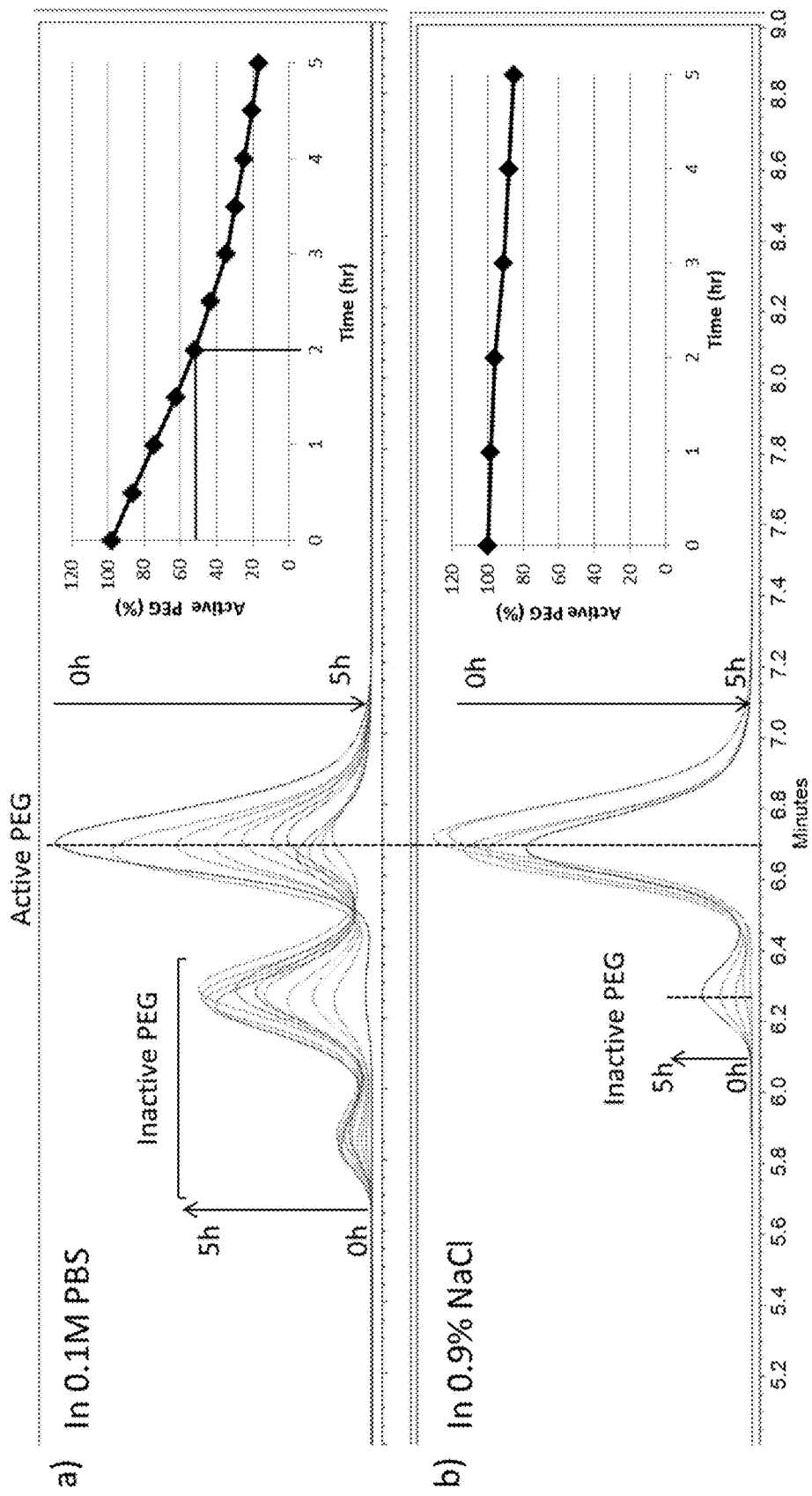
FIG. 13 shows the half-life of active PEG-5K-HS half-life (118.9 mg/mL) in (a) 0.1 M PBS, pH 7.7 and (b) 0.9% NaCl, respectively. Peak areas of active PEG shrunk over the course of 5 hours, as peaks of inactive/hydrolyzed PEG gradually increased at the same rate.

In this study, four species with fixed PEG chain length (5 kDa), but with acetyl-, pentyl-, hexyl- and decanoyl-carbon chains as their respective spacer-arms, were investigated. Each type of PEG-NHS ester was dissolved in 0.1 M PBS and in 0.9% NaCl in separate trials. Samples were collected every 30 minutes for a total of 5 hours, and the amount of active and inactive form of PEG was determined by the peak area of each corresponding species in the chromatograms. FIG. 13 shows a representative elution profile of PEG-5K-HS as an example. Peak area of active PEG (retention time=6.7 min) shrunk over the course of 5 hours, as peaks of hydrolyzed PEGs (retention time=5.7-6.5 min) gradually increased at the same rate. The half-life of active PEG-5K-HS was estimated from the plot of time versus the quantified amount of inactive PEG in the reaction mixture, the half-lives regarding the hydrolysis rate of the 4 types of PEG-NHS ester in PBS and in 0.9% NaCl, respectively, are summarized in Table 8. The results showed that the half-life of PEG-5K-PS (spacer-arm 3 carbons) in PBS was determined to be 1 hour while lengthening the spacer-arm to 10 carbons (PEG-5K-DCS) significantly increased the half-life to 3.7 hours. This suggests that the spacer-arm length is negatively correlated with the rate of PEG hydrolysis, where the half-life of active PEG increases with the length of the spacer-arm. Notably, the results also revealed that PEG displayed enhanced stability from the dissolution in 0.9% NaCl compared with that in PBS. For instance, the stability of PEG-5K-PS was increased by 7-fold from the dissolution in 0.9% NaCl ($t_{1/2}$ in PBS=1 hr vs. $t_{1/2}$ in 0.9% NaCl=7.2 hr). Similar finding was also observed for PEG-5K-HS ($t_{1/2}$ in PBS=2 hr vs. $t_{1/2}$ in 0.9% NaCl>8.0 hr).

TABLE 8

Hydrolysis Rate and Half-life for PEG-5K-AS, PEG-5K-PS, PEG-5K-HS and PEG-5K-DCS in 0.9% NaCl and 0.1M PBS, respectively, at room temperature.

| PEG-NHS Ester Species | Dissolution Conditions | Active PEG after 5 hr [%] | Half-life ($t_{1/2}$) |
| --- | --- | --- | --- |
| PEG-5K-AS | 0.9% NaCl | 0 | ≤5 min |
| PEG-5K-PS | | 64.8 | 7.2 hr |
| PEG-5K-HS | | 84.8 | >8 hr |
| PEG-5K-DCS | | 94.6 | >8 hr |
| PEG-5K-AS | PBS | 0 | Spontaneous |
| PEG-5K-PS | | 0 | 1 hr |
| PEG-5K-HS | | 11.0 | 2 hr |
| PEG-5K-DCS | | 33.1 | 3.7 hr |

Example 8B: Reaction Optimization Upon Changing the PEG Stock Solution Medium

In light of the increased stability of PEG-NHS ester in 0.9% NaCl solution compared with that in 0.1 M PBS, a reaction trial was carried out by preparing the PEG solution in 0.9% NaCl and the stock solution was kept at room temperature for 0, 1 and 2 hours before the conjugation reaction so as to study the effect of extended processing time on the pegylation yield, which may also provide insight on the flexibility of the pegylation process. The pegylation reaction was conducted in a similar manner as shown in the previous examples with 4.5 g/dL Hb containing 59.3 mg/mL PEG-5K-HS for the conjugation, and a control study was also carried out by the dissolution of PEG-5K-HS in PBS. As shown in Table 9, no significant difference was found in the PEG conjugation number when the reactions were carried out immediately after dissolution in either 0.9% NaCl or in PBS (t=0 h; 14.0 and 13.9 PEG/Hb, respectively; pegylation yield=82%). In contrast, when the reaction was delayed by 2 hours, there was a slight decrease in conjugation number from 14.0 to 12.4 PEG/Hb in 0.9% NaCl (pegylation yield=82% and 73%, respectively). However, a massive reduction of conjugation efficiency was found for that in PBS (decreased from 13.9 to 5.1 PEG/Hb; pegylation yield=82% and 30%, respectively) when the reaction was delayed for 2 hours. The reduction of conjugation number and pegylation efficiency under PBS solution suggests that a higher reaction equivalent, and thus higher production cost, will be required in order to compensate for the loss of PEG reagent through hydrolysis. Therefore, the preparation of PEG stock solution in 0.9% NaCl would minimize the hydrolysis of the PEG reagents and hence improve the pegylation yield of the reaction, thus reducing the cost of the production process.

TABLE 9

Effects of Dissolution Medium and Dissolution Time on the Pegylation Efficiency.

| Dissolution Buffer | Reaction Delay after Dissolution of PEG [hr] | Determined PEG/Hb Ratio | Pegylation Yield [%] | Hydrodynamic Diameter [nm] |
| --- | --- | --- | --- | --- |
| PEG in 0.9% NaCl | 0 | 14.0 | 82 | 14.17 ± 0.07 |
| | 1 | 12.9 | 76 | 14.09 ± 0.07 |
| | 2 | 12.4 | 73 | 13.69 ± 0.08 |
| PEG in 0.1M PBS | 0 | 13.9 | 82 | 13.92 ± 0.02 |
| | 1 | 7.5 | 44 | 12.34 ± 0.12 |
| | 2 | 5.1 | 30 | 11.38 ± 0.04 |

Example 8C: Pegylation Reaction Through Addition of PEG in Powder Form

As shown in the above examples, the conjugation yield of PEG-5K-AS was found to be inefficient (PEG/Hb=2.5, pegylation yield=14%, Table 7) owing to its high hydrolysis rate. The pegylation efficiency of PEG-5K-AS is enhanced by direct addition of PEG reagent in its powder form so as to minimize the loss of active PEG in the solution preparation step. Notably, upon changing the reagent addition method, there is significant improvement in the pegylation efficiency for the reaction using PEG in powdered form compared to that in aqueous form (Powdered: ~7.7 PEG/Hb; PBS: ~2.5 PEG/Hb; Table 10), although the conjugation number is still lower than those observed in other PEG-NHS esters examined. In order to further increase the conjugation number, a two-step pegylation reaction, each step with 17 equivalents of PEG, was performed using PEG-5K-AS.

As shown in Table 10, the pegylation efficiency was found to be similar among the first and second pegylation reactions (7.7 and 7.4 PEG/Hb, respectively), indicating that the amount of active PEG is the limiting factor governing the pegylation efficiency of the reaction. Additionally, this result suggests that the efficiency can be increased by removing the initial PEG dissolution step; thus, the impact of PEG hydrolysis toward the conjugation yield can be minimized, leading to an effective conjugation of hemoglobin with the use of PEG reagent having high hydrolysis rate.

TABLE 10

Properties of Pegylated Cysteinyl-succinyl crosslinked Hemoglobin with PEG Reagents with Different Spacer-arm Chain Lengths under Different Conditions. PEG equipped with different spacer-arm lengths (17 molar equivalents, dissolved in 0.1M of PBS or remained in solid form) were reacted with hemoglobin (p50 = 55.9 ± 0.2 mmHg) under deoxygenated conditions for 2 hours.

| PEG-NHS Ester Species | Pegylation Conditions | PEG/Hb | MW [kDa] | Hydrodynamic Diameter [nm] |
|---|---|---|---|---|
| PEG-5K-AS | 17 Equivalent PEG in PBS | 2.5 | 77 | 7.8 ± 0.1 |
| PEG-5K-PS | | 12.6 | 128 | 13.2 ± 0.1 |
| PEG-5K-HS | | 13.5 | 132 | 12.6 ± 0.1 |
| PEG-5K-DCS | | 12.9 | 129 | 13.1 ± 0.1 |
| PEG-5K-AS | 17 Equivalent PEG in Powder | 7.7 | 103 | 11.4 ± 0.1 |
| PEG-5K-PS | | 14.2 | 135 | 15.1 ± 0.6 |
| PEG-5K-HS | | 14.9 | 139 | 14.3 ± 0.2 |
| PEG-5K-DCS | | 14.2 | 135 | 14.4 ± 0.1 |
| PEG-5K-AS | Powder PEG (×2)[a] | 15.1 (7.7 + 7.4) | 140 | 13.9 ± 0.1 |

[a]two successive cycles of pegylation reactions with 17 molar equivalents of PEG reagent used in each reaction.

Similar pegylation reaction was conducted with other PEG-NHS esters with longer spacer-arm chain length. However, the improvement of conjugation efficiency was less prominent for the PEG examined, as shown in Table 10. Additionally, regardless of the different spacer-arm lengths used, given that a similar number of PEG was attached, the hydrodynamic diameters of the resulting pegylated hemoglobin were found to be similar (13.9-15.1 nm).

Nonetheless, all the results as shown in EXAMPLE 8B and 8C indicated that the efficiency of pegylation reaction can be enhanced by (1) preparation of PEG stock solution in 0.9% NaCl solution and (2) addition of PEG reagent in powdered form.

With the selection of suitable method for the pegylation process, PEG chains with various properties can be effectively attached to cysteinyl-succinyl crosslinked hemoglobin to obtain pegylated crosslinked hemoglobin with desired properties.

Example 9: Determination of Maximum Pegylation Number on Cysteinyl-Succinyl Crosslinked Hemoglobin In the pegylation process of cysteinyl-succinyl crosslinked hemoglobin, PEG-NHS ester reacts with the surface-exposed amines to give a stable amide bond between PEG and hemoglobin. Since the lysine side chain contributes the majority of the primary amines in a protein, the maximum conjugation number of PEG chain on the hemoglobin roughly equals the number of lysine residues in the protein's amino acid sequence (i.e., 48 lysine residues for bovine hemoglobin and 4 amino groups from the N-terminus of the hemoglobin subunits), although the actual empirical numbers would be lower due to the steric hindrance originated from PEG chains and amino acid side-chains.

With an aim to determine the maximum conjugation number between the reactions of PEG-NHS ester and cysteinyl-succinyl crosslinked hemoglobin, a pegylation reaction of cysteinyl-succinyl crosslinked hemoglobin was carried out using PEG-1K-HS dissolved in 0.1 M PHS, under deoxygenated conditions for 2 hours. As shown in Table 11, upon varying the reaction equivalents of the PEG-1K-HS from 17 to 85, the number of PEG conjugated significantly increased from 12.7 to 48.2. Notably, this value showed a negligible increase upon further increasing the reaction equivalent of PEG to 143, probably suggesting 48 PEG chains are the maximum number of conjugation to cysteinyl-succinyl crosslinked hemoglobin under the reaction conditions examined. In the reaction with PEG-5K-HS, a total of 43 PEG/Hb was achieved with increased molecular weight (280 kDa), but only with a slightly increased hydrodynamic diameter (from 14.1 to 15.9 nm).

TABLE 11

Examination of Maximum Conjugation Number of PEG Chains towards Cysteinyl-succinyl Crosslinked Hemoglobin using PEG-1K-HS.

| Reaction Amount of PEG-1K-HS [mg/mL of reaction] | PEG Equivalent | Determined PEG/Hb Ratio |
|---|---|---|
| 11.9 | 17 | 12.7 |
| 59.3 | 85 | 48.2 |
| 100 | 143 | 48.3 |

Example 10: Specifications of Composition of Pegylated Cysteinyl-Succinyl Crosslinked Hemoglobin The specifications of the pegylated cysteinyl-succinyl crosslinked hemoglobin used for the below safety, pharmacokinetics and tissue oxygenation studies, are shown in Table 12.

TABLE 12

Physical Properties of Cysteinyl-succinyl Crosslinked Hemoglobin Conjugate.

| | Pegylated Cysteinyl-succinyl Crosslinked Hb |
|---|---|
| tHb [g/dL] | 4.5-5.5 |
| pH | 7.4-8.4 |
| MetHb [%] | ≤8% |
| Endotoxin [EU/mL] | ≤0.25 |
| Colloid Osmotic Pressure [mmHg] | >73 |
| Estimated PEG no./Hb | 12-14 |
| Estimated MW [kDa] | 125-135 |
| Average Hydrodynamic Size [nm] | 13.5-14.5 |
| Free Dimer [%] | 0 |
| Unpegylated Hemoglobin | ≤5% |
| Residual PEG [mg/mL] | ≤0.2 |

Example 11: Safety of Pegylated Cysteinyl-Succinyl Crosslinked Hemoglobin

Example 11A: Reduced Immunogenic Responses in Rat with Infusion of Pegylated Cysteinyl-Succinyl Crosslinked Hemoglobin Immunogenic safety in patients is crucial for successful protein therapeutics development, especially for those used for repeated dosing and prolonged exposure. Therefore, the immunogenicity of the pegylated cysteinyl-succinyl crosslinked hemoglobin was evaluated using a rat immunization model established by Chang TMS and Varma R (Chang, T. M. S & Varma, R., 1998, Artif Cells Blood Substitut Biotechnol, 16(1-3): 205-215). This screening platform can differentiate the host immune response and possible adverse effects of hemoglobin products used for repeated dosing.

Figure 14:
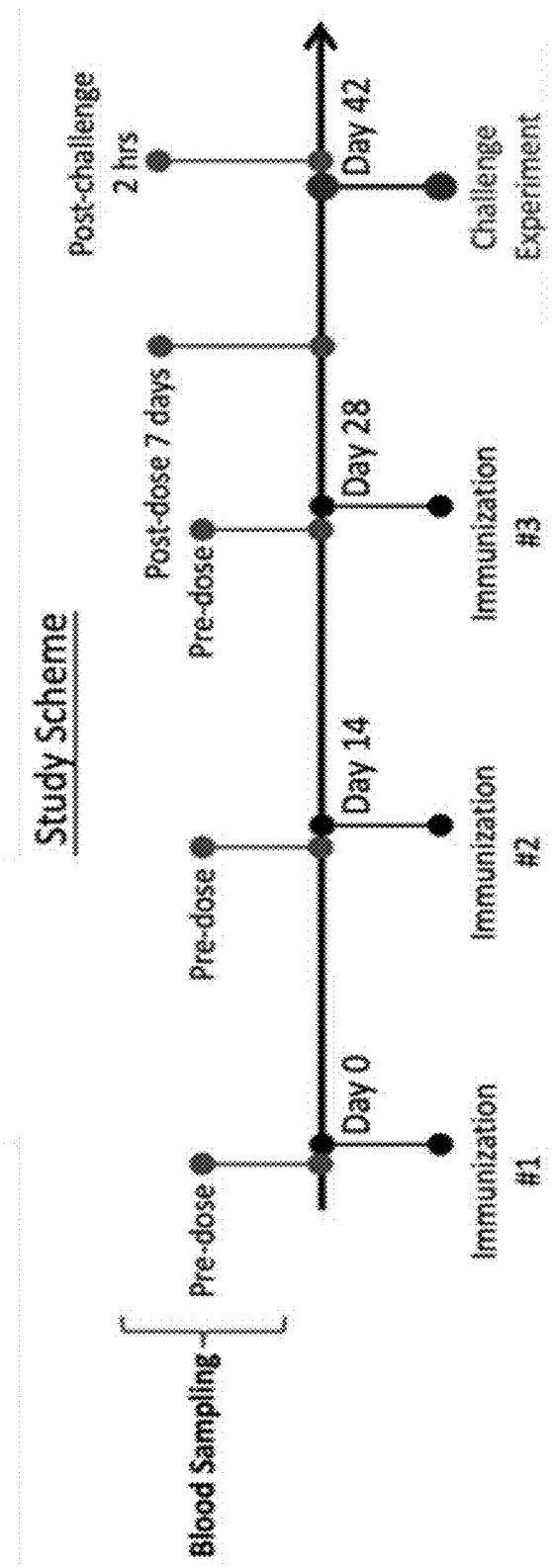
FIG. 14 depicts the study scheme for the immunization and challenge experiment in rats.

Male Sprague-Dawley (SD) rats aged 6-8 weeks (250 g±25 g) were used for this study. The immunization schedule followed Chang TMS and Varma R (Chang, T. M. S & Varma, R., 1998, Artif Cells Blood Substitut Biotechnol, 16(1-3): 205-215) with minimum modification, as shown in FIG. 14. Each rat received three immunization doses of 1 mg/mL pegylated cysteinyl-succinyl crosslinked hemoglobin at Day 0, 14 and 28. The subcutaneous (s.c.) injection of 1 mg/mL/rat inoculum of equal volume of pegylated cysteinyl-succinyl crosslinked hemoglobin and Freund's complete (for first immunization) or incomplete (for second and third immunization) adjuvant to induce immunogenic response. Subsequently, rats were challenged by intravenous (i.v.) injection of 2 mL of 100 mg pegylated cysteinyl-succinyl crosslinked hemoglobin per rat biweekly for a total of 4 rounds of challenge. Body weights were recorded prior to each immunization and after each challenge dose. Survival and clinical signs were recorded after each challenge dose. Blood was collected via retro-orbital route before each immunization and post-2 hour and at different time points after the challenge under anesthesia for blood analysis. Organs were harvested for histopathological analyses at 24 hour post-challenge.

i) Immunoglobulin and Immune Complex Profile

Figure 15:
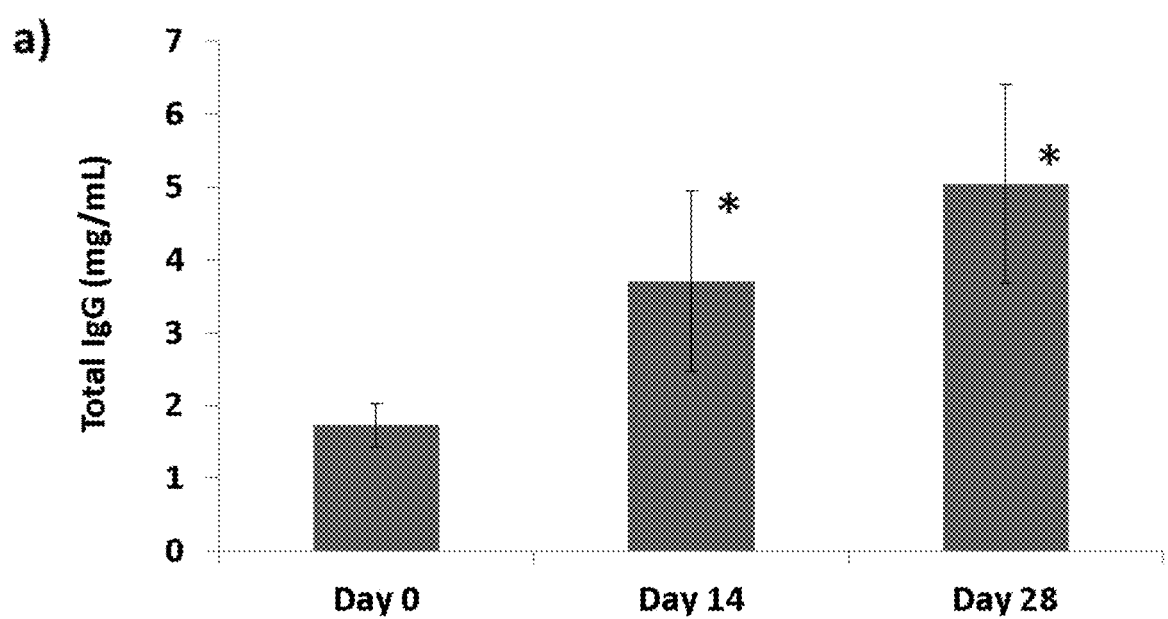
FIG. 15 shows the total plasma IgG level in rats (a) during 3 rounds of immunization with pegylated cysteinyl-succinyl crosslinked hemoglobin, respectively (n=6*p<0.5) and (b) after 4 challenge doses of pegylated cysteinyl-succinyl crosslinked hemoglobin (n=3).
Figure 15:
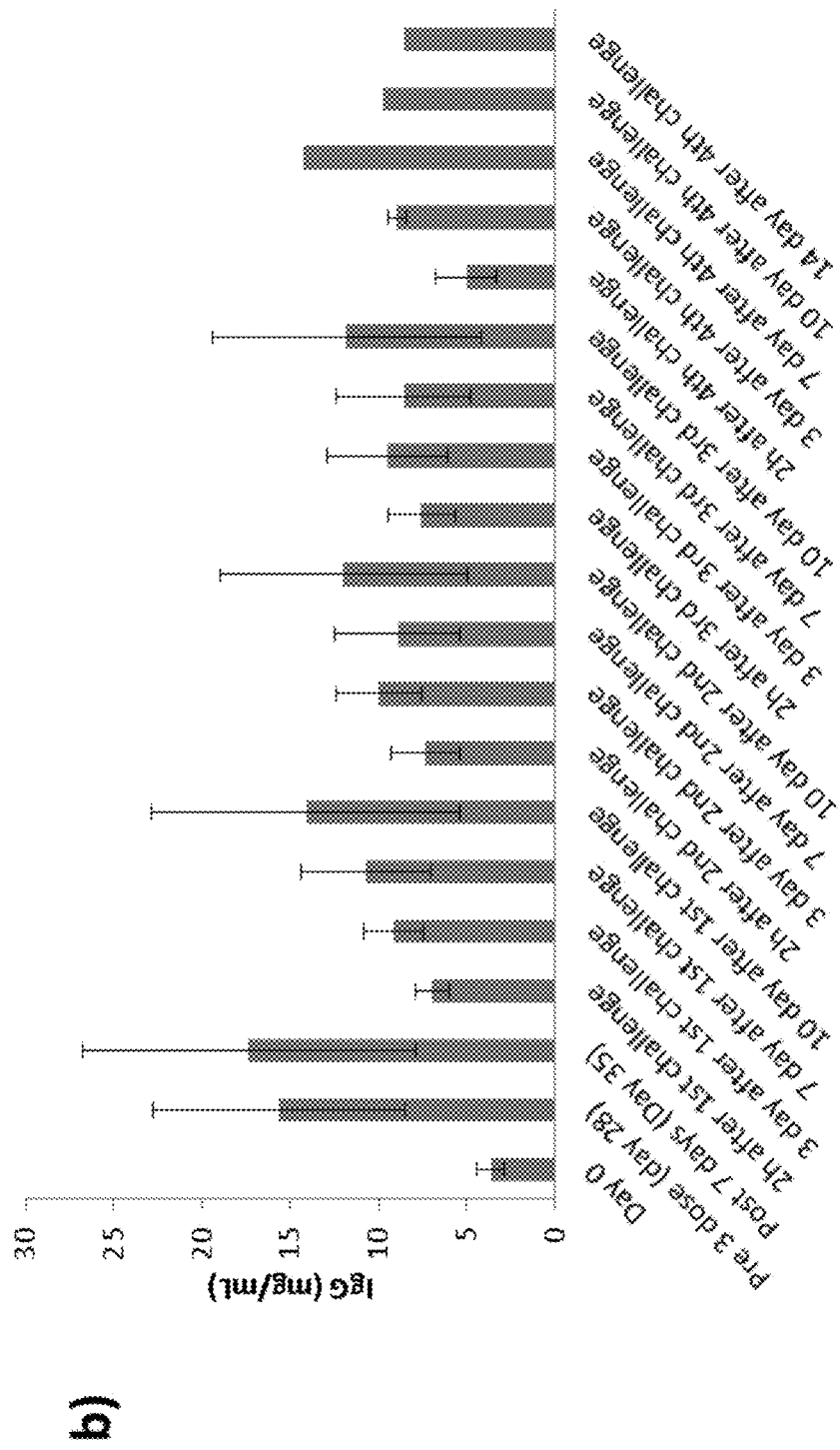

Blood samples collected in K2-EDTA tubes underwent centrifugation to separate plasma for immunoglobulin (IgG) detection. The levels of total IgG in plasma were quantified by rat IgG ELISA kits following manufacture's recommendation. Immunization of rats with pegylated cysteinyl-succinyl crosslinked hemoglobin induced an increasing level of IgG from Day 0, Day 14 to Day 28, as shown in FIG. 15a. Blood was also collected every 3 to 5 days after the challenge dose for the total level of IgG detection in plasma. FIG. 15b showed an increased total IgG level after third immunization doses and peaked at Day 10 after each challenge dose. The increased IgG level after each high dose (100 mg/2 mL) challenge was lower than that after immunization. This suggested a higher dose did not trigger greater IgG levels. In addition, the level of IgG after each challenge did not increase significantly when compared to prior challenge and the increased IgG level after the $4^{th}$ challenge was also reduced by 14 days, as shown in FIG. 15b. This implies that repeated doses of pegylated cysteinyl-succinyl crosslinked hemoglobin did not trigger a hyper immune response and that the increased level of IgG can only sustain for a period of 14-day.

To study the profile of anti-drug antibody (ADA) response against pegylated cysteinyl-succinyl crosslinked hemoglobin, sample containing 5 μg pegylated cysteinyl-succinyl crosslinked hemoglobin (antigen) was mixed with sodium dodecyl sulphate-polyacrylamide gel electrophoresis (SDS-PAGE) protein loading buffer and boiled at 95-100° C. for 10 minutes. Samples and pre-stained marker were loaded to 7.5% SDS-PAGE gel. The gel was run at 80V for 15 minutes followed by 120V for approximately 60 minutes in 1× Running Buffer (BioRad). Proteins were then transferred to polyvinylidene fluoride (PVDF) membrane in 1× Transfer Buffer (BioRad) with 20% ethanol using the Trans-Blot Turbo Transfer System (BioRad) for 10 minutes at room temperature. After protein transfer, the membrane was then blocked by 5% non-fat milk for 1 hr at room temperature with agitation, followed by 3 washes with 1×TBST (Tris-buffered saline (TBS) with 0.05% Tween-20). The membrane was incubated in rat plasma collected (primary antibody; diluted with 5% non-fat milk to 0.01 g/dL total protein concentration) with agitation overnight at 4° C. The membrane was then washed with TBST for 3 times with agitation for 10 minutes, followed by incubating it in anti-rat IgG HP (secondary antibody, diluted in 5% non-fat milk to 1:10000 dilution) for 1 hour with agitation at room temperature. After the $2^{nd}$ antibodies incubation, the membrane was washed with TBST for 3 times with agitation for 10 minutes and incubated with peroxide and luminol/enhance solution mixture and imaged the blot using ChemiDoc imaging system.

Figure 16:
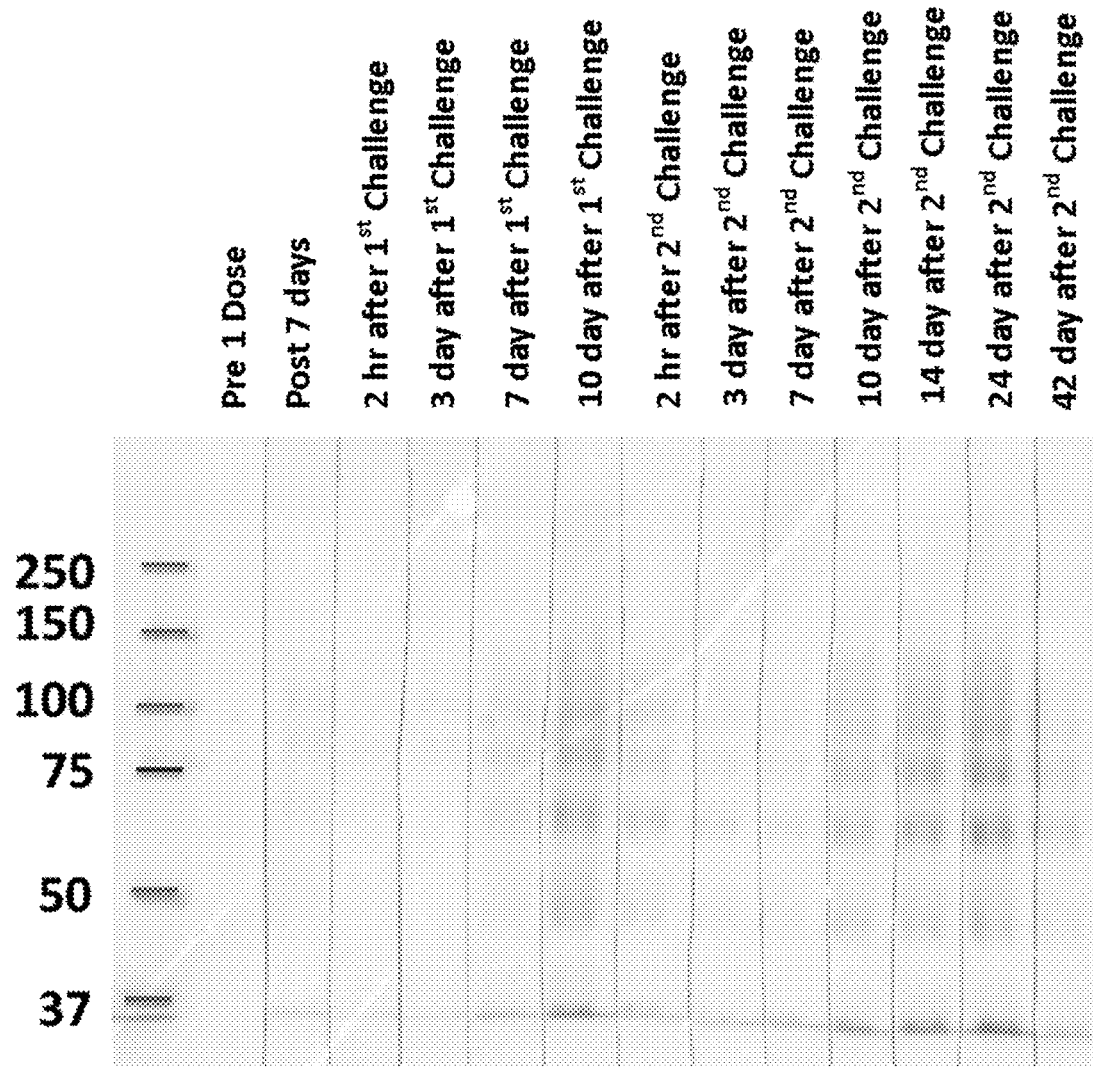
FIG. 16 shows the western blot results of ADA triggered by pegylated cysteinyl-succinyl crosslinked hemoglobin, after 2 challenge doses.

The western blot results showed that the intensity corresponding to ADA increased gradually after the $1^{st}$ challenge dose and reached peak at post 10 day after $1^{st}$ challenge, and dropped before the $2^{nd}$ challenge dose, as shown in FIG. 16. A similar trend was observed in each challenge dose, the signal was maintained for nearly 14 days and decreased over the time. Although the level of specific ADA was increased after each challenge dose, its level was relatively low, compared to that observed for unpegylated hemoglobin.

Apart from the detection of ADA in circulation, the level of specific immune complex (IC) between the ADA and pegylated hemoglobin was evaluated after each challenge dose. It is reported that most adverse effects related to immunogenicity for therapeutic proteins is a consequence of circulating and cell surface bound drug bearing IC (Krishna, M. & Nadler, S. G, 2016, Front Immunol, 7:21). Therefore, the levels of specific IC triggered by the challenge dose of pegylated cysteinyl-succinyl crosslinked hemoglobin in immunized rats were measured using an in-house developed ELISA. The Pierce™ Protein A/G coated microtiter plate (ThermoScientific) was coated with 1 μg/mL rabbit anti-cysteinyl-succinyl crosslinked hemoglobin antibody in 100 mM bicarbonate buffer (pH 9.6) overnight at 4° C. Wells were washed with 10 mM phosphate-buffered saline pH 7.4 in 0.05% (v/v) Tween® 20 (PBST) 3 times and blocked by Starting Block™ buffer (ThermoFisher) for 1 hr at 37° C. After the wells were washed with PBST for 4 times, 100 μL of 4-fold serially-diluted rat plasma in Starting Block™ solution starting at 1:25 was added to the wells and incubated for 1 hr at 37° C. Plates were washed 4 times with PBST and 100 μL of anti-rat IgG conjugated with horseradish peroxidase (HRP) diluted in 1:12000 with Starting Block™ solution were added to the wells and incubated for 1 hr at 37° C. followed by 4 PBST washes. 100 μL of 3,3',5,5' tetramethylbenzidine (TBM) was added to the wells. 100 μL of 0.1 M hydrochloric acid was added after the color was developed. The absorbance at 450 nm was measured using FLUOstar Omega microplate reader (BMG LABTECH).

Figure 17:
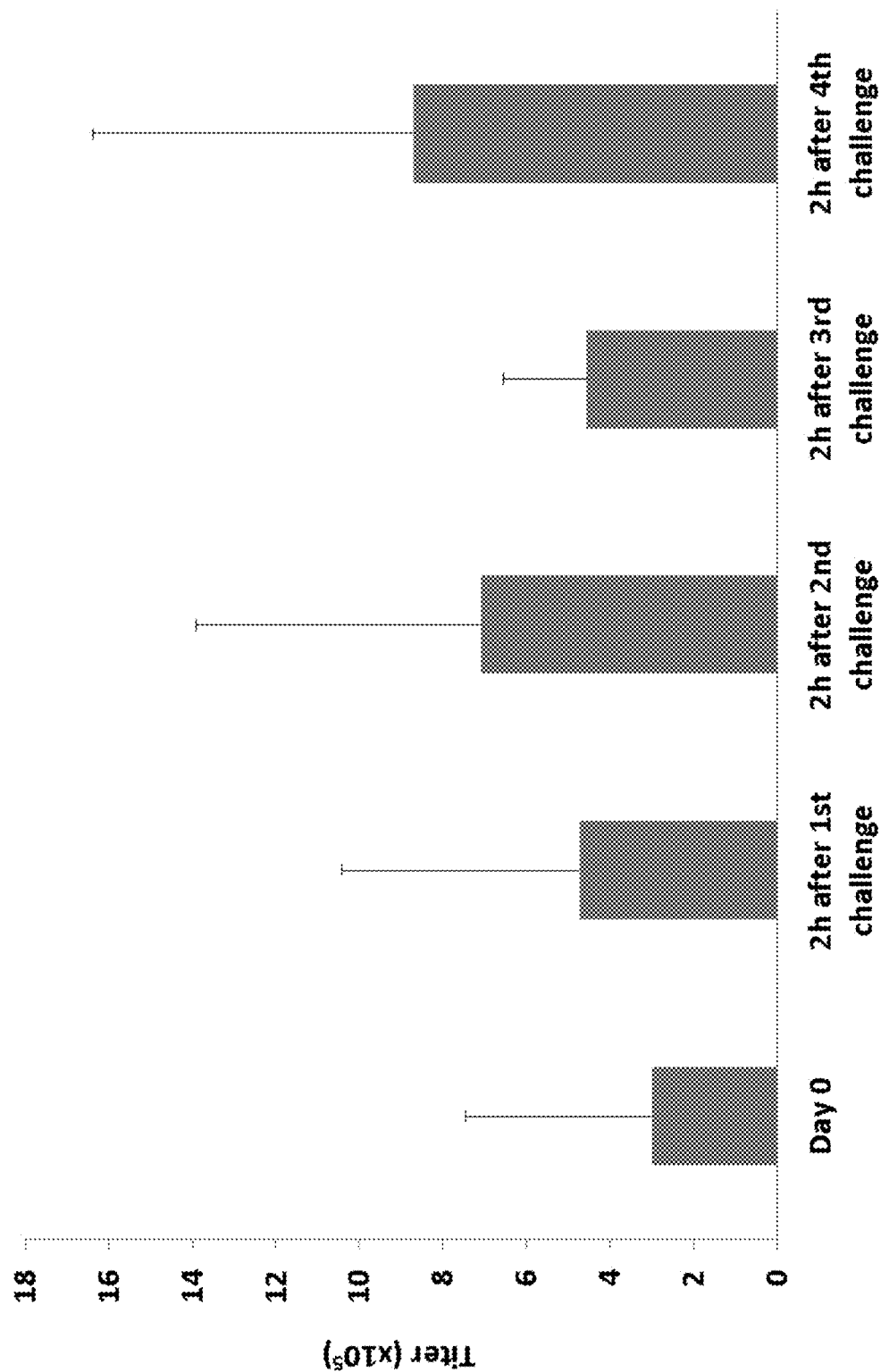
FIG. 17 shows the formation of specific immune complex in pegylated cysteinyl-succinyl crosslinked hemoglobin-immunized rats after 4 challenge doses.
Figure 18:
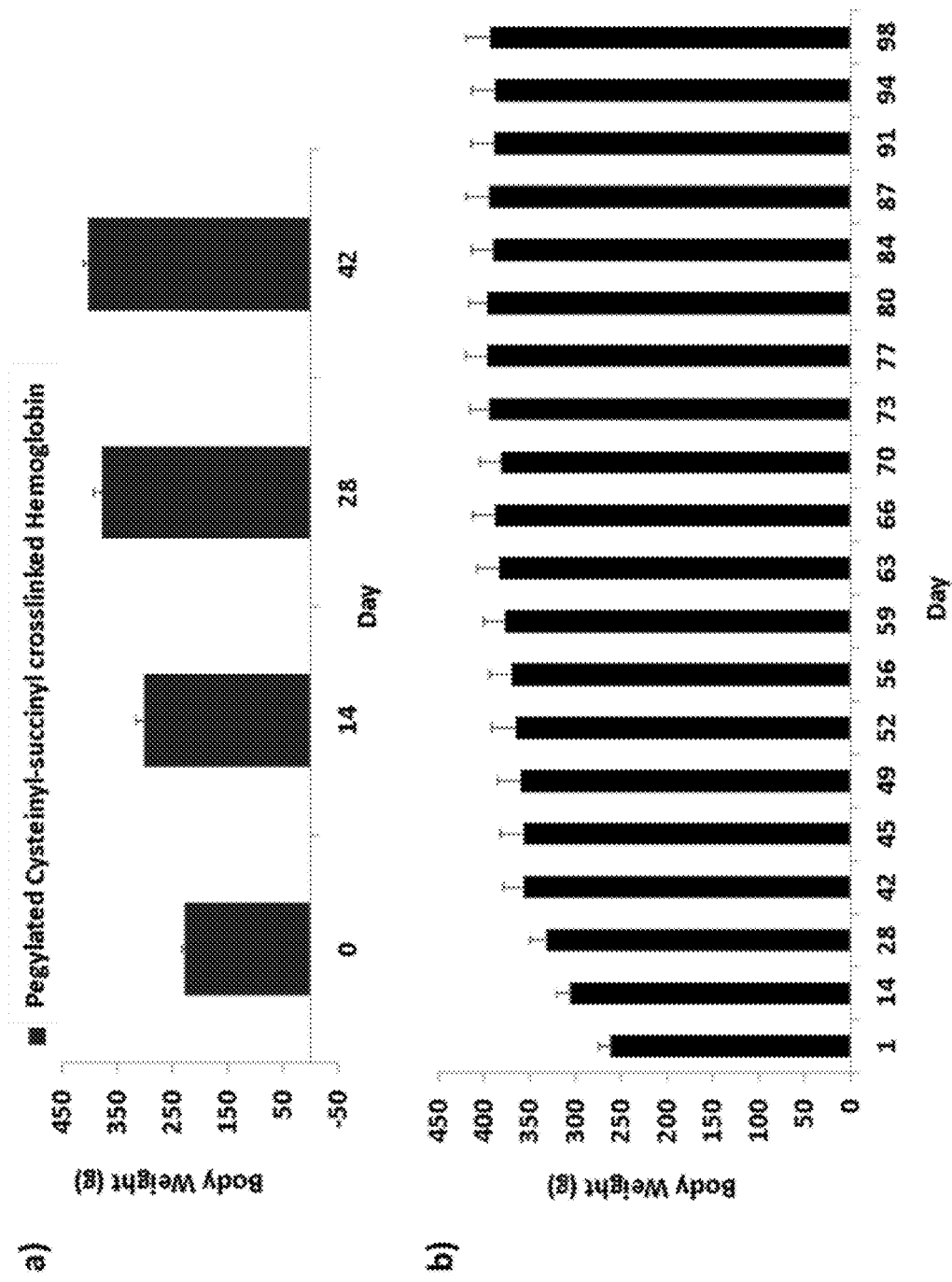
FIG. 18 shows the body weight change of rats during (a) immunization of pegylated cysteinyl-succinyl crosslinked hemoglobin-immunized and (b) 4 challenge doses from Day 0 to Day 98.

The results showed that the repeated challenge of high dose (100 mg/rat) of pegylated cysteinyl-succinyl crosslinked hemoglobin in the immunized rats, the IC titer at 2 hr after each challenge was slightly higher than previous challenge except for the $3^{rd}$ challenge, as shown in FIG. 17. However, this increase was still low relative to the one time challenge of unpegylated hemoglobin-immunized rats.

ii) Body Weight, Survival Rate, Adverse Clinical Symptoms and Histopathological Changes The body weight of rats was recorded before each immunization dose and 2 hour after the challenge dose. Clinical signs and survival rate of rats were observed after each challenge. FIG. 18a showed that the body weight of rats immunized with pegylated cysteinyl-succinyl crosslinked hemoglobin increased from Day 0 to Day 42. Multiple challenges of rats with high dose also do not affect the body weight of the rats, as shown FIG. 18b. Importantly, all rats survived with challenge of 100 mg/rat of pegylated cysteinyl-succinyl crosslinked hemoglobin for 4 bi-weekly challenge doses and only a few rats had cyanosis at ears and feet (25%, 3 out of 12 rats) and displayed hypo-activity (58%, 7 out of 12 rats) immediately after challenge, as summarized in Table 3. Moreover, the rats recovered from such mild adverse clinical symptoms within 20 minutes after the challenge and there was a progressive decrease in the percentage of hypo-activity in rats after each challenge dose, as shown in Table 13.

TABLE 13

Survival Rate and Adverse Clinical Symptoms Observed in Rat after Challenge.

|     |                    | Percentage | 1st | 2nd | 3rd | 4th |
| --- | ------------------ | ---------- | --- | --- | --- | --- |
|     | Death              | 0% (0/12)  |     |     |     |     |
| Adv | Ear & Feet Cyanosis | 25% (3/12) | 25% (3/12) |     | 20% (1/5) |     |
|     | Diarrhea           | 0% (0/12)  |     |     |     |     |
|     | Hypo-activity      | 58% (7/12) | 58% (7/12) | 50% (4/8) | 20% (1/5) | 50% (1/2) |
|     | Rapid Breathing    | 0% (0/12)  |     |     |     |     |
|     | Limbs Swelling     | 0% (0/12)  |     |     |     |     |
|     | Gait Instability   | 0% (0/12)  |     |     |     |     |

Figure 19:
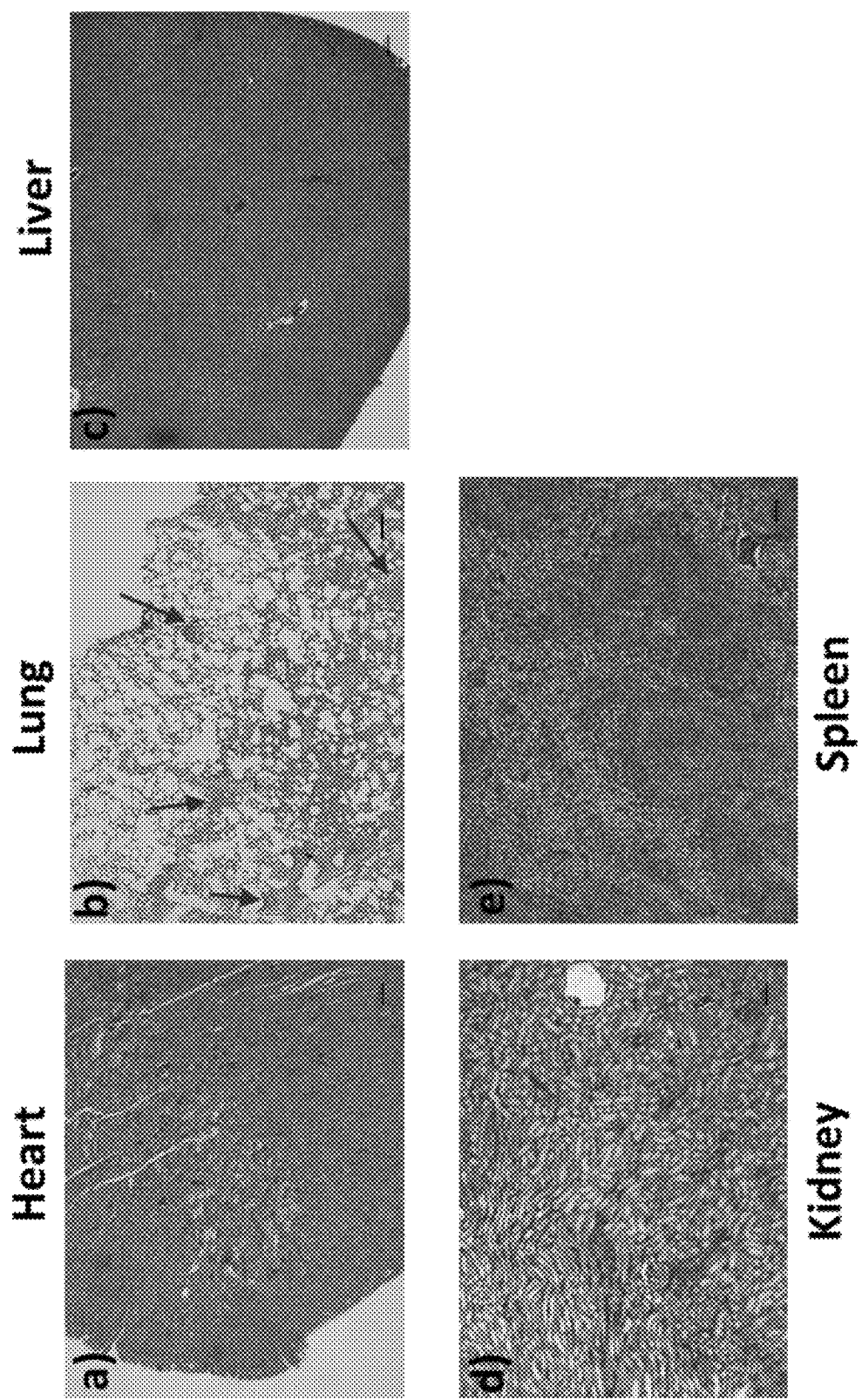
FIG. 19 depicts the histopathological sections of (a) heart, (b) lung, (c) liver, (d) kidney and (e) spleen from rats challenged with pegylated cysteinyl-succinyl crosslinked hemoglobin. Rat organs were harvested at 24 hour post-challenge. Red arrow on lung picture showed mild alveolar infiltrates. Bars: (a-e) 100 μm; Magnification 50× for a, c-e and 40× for b.

The challenged rats were further analyzed for histopathological changes. The rat organs including kidney, liver, spleen and heart were harvested at 24 hours post-challenge with pegylated cysteinyl-succinyl crosslinked hemoglobin. Only mild alveolar infiltrates was found in the lung and no significant histopathological changes was observed in other organs, as shown in FIG. 19.

In summary, the results revealed that four times repeated high dose (100 mg/rat) challenge of pegylated cysteinyl-succinyl crosslinked hemoglobin in immunized rats would not trigger an immediate increase of specific ADA, though an increase of total IgG level was observed. Importantly, a relatively low IC titer was detected post 2 hours in every challenge dose and even after 4 high dose challenges. Multiple challenge of rats with pegylated cysteinyl-succinyl crosslinked hemoglobin do not reduce the survival rate of rats, and histopathological assessment suggested no clinically significant finding in heart, liver, kidney and spleen, only a mild alveolar infiltration was found in the lung. Thus, it is believed that the pegylated cysteinyl-succinyl crosslinked hemoglobin only elicits mild host humoral response and would not trigger high immunogenic response for repeated dosing, or cause any significant adverse effects. As such, it is more antigenically safe to administer, especially for repeated dosing and prolonged exposure.

Example 11B: Elimination of Renal Toxicity by Pegylated Cysteinyl-Succinyl Crosslinked Hemoglobin The hematoxylin and eosin (H&E)-stained kidney tissues showed intact tubules and no loss of tubule cells after pegylated cysteinyl-succinyl crosslinked hemoglobin challenge (FIG. 19d). No hemorrhage and blood clot were observed in the kidney tissues. This suggested that the IV-infusion of pegylated cysteinyl-succinyl crosslinked hemoglobin would not cause any kidney structural damage or kidney injury at 24 hr-post challenge.

Example 11C: Reduced Cardiac Toxicity of Pegylated Cysteinyl-Succinyl Crosslinked Hemoglobin Cardiotoxicity, namely myocardial infarction, has been reported from a number of HBOC products (Estep, T. P., 2019, Artif Cells Nanomed Biotechnol, 47: 593-601). To assess the cardiac toxicity of pegylated cysteinyl-succinyl crosslinked hemoglobin, Sprague Dawley (SD) rats were used. Following brief anesthesia with isoflurane, antibiotics and analgesics were administrated before surgery. After the surgical site was cleaned and slaved, an incision was made to the right of the midline of the ventral surface of the neck, along the jugular groove, and the right jugular vein was isolated. Following the cannulation of the vessel, the sterile catheter primed with normal saline, was tunneled using a sterile I.V. catheter to a position on the dorsal surface of the rat, whereupon it was connected to a harness. The neck wound was closed using Michel clips. The harness was connected to a swivel tether, and the rat, removed from anesthesia, was then placed in a single housed cage. The tether was then connected to a syringe pump and saline pumped at a slow rate to ensure the potency. The rat was allowed to recover for at least 4 days before dosing.

On the dosing day, the weight of the rat was measured and the pegylated cysteinyl-succinyl crosslinked hemoglobin was given via a syringe pump at 1250 mg/kg with infusion rate at 6 mL/kg/hr, respectively. Same volume of buffer was infused in the control group in parallel. Hearts were harvested at 72 hours post administration and examined macroscopically, and then they were immersed in neutral buffered 10% formalin solution for tissue fixation, following by histopathological analysis. The histopathological results showed that rats infused with pegylated cysteinyl-succinyl crosslinked hemoglobin (n=6, per group) at 1250 mg/kg appeared to be well tolerated and no significant lesion of heart was observed, while infusion of unpegylated hemoglobin to the rat resulted in cardiomyopathy in 4 out of 6 rats, as shown in Table 14. Severity of heart lesions raging from very mild to moderate were defined in the rat infused with unpegylated crosslinked hemoglobin. This suggests that the pegylated cysteinyl-succinyl crosslinked hemoglobin is less cardiotoxic than the unpegylated ones.

TABLE 14

Incidence of Cardiomyopathy in Rats with Single Infusion of Pegylated Cysteinyl-succinyl Crosslinked Hemoglobin.

| Group | Dose Level (mg/kg) | Incidence of Cardiomyopathy |
|---|---|---|
| Control Group | 0 | 0/12 |
| Pegylated Hemoglobin | 1250 | 0/6 |
| Unpegylated Hemoglobin | 1250 | 4/6 |

Example 12: Pharmacokinetics of Pegylated Cysteinyl-Succinyl Crosslinked Hemoglobin

Example 12A: Enhanced In Vivo Circulation Stability of Pegylated Cysteinyl-Succinyl Crosslinked Hemoglobin The half-life of pegylated cysteinyl-succinyl crosslinked hemoglobin in SD rat was investigated. Male SD rats (250-280 g) were anesthetized by 1.5% isoflurane and were undergone cardiac and femoral catheterization 3 days before infusion. Rats were infused with 620 mg/kg pegylated cysteinyl-succinyl crosslinked hemoglobin with an infusion rate of 3 mL/kg/hr. Rat plasma samples were collected at pre-dose, 1, 2, 4, 15, 24, 28 and 44 hours post-infusion. Total hemoglobin of samples and standards were measured using HemoCue® Plasma/Low Hb System and the half-lives were calculated using PKSolver 2.0 (Linear Trapezoidal).

The results showed that the half-life of pegylated cysteinyl-succinyl crosslinked hemoglobin was almost triple ($t\frac{1}{2}$=19.9 hr), compared to that of unpegylated cysteinyl-succinyl crosslinked ($t\frac{1}{2}$=7.1 hr), as shown in Table 15. This implies that the pegylation of cysteinyl-succinyl crosslinked hemoglobin increases in-vivo blood circulation times by changing the pharmacokinetics properties of the crosslinked hemoglobin itself. HBOC product with enhanced in vivo circulation stability can increase its bioavailability to achieve higher therapeutic effect.

TABLE 15

In vivo Circulation Stability of Pegylated Cysteinyl-succinyl Crosslinked Hemoglobin vs. Cysteinyl-succinyl Crosslinked Hemoglobin.

| | Half-life ($t\frac{1}{2}$) |
|---|---|
| Pegylated Cysteinyl-succinyl Crosslinked Hemoglobin | 19.9 hr |
| Cysteinyl-succinyl Crosslinked Hemoglobin | 7.1 hr |

Example 12B: In Vivo Distribution of Pegylated Cysteinyl-Succinyl Crosslinked Hemoglobin The in vivo distribution of pegylated cysteinyl-succinyl crosslinked hemoglobin was studied in male Balb/c mice. All mice were supplied with low-fluorescence diet throughout the study. Male Balb/c mice (20-25 g) were individually administered with 10 mg/0.25 mL/mouse of pegylated cysteinyl-succinyl crosslinked hemoglobin or cysteinyl-succinyl crosslinked hemoglobin, respectively. For the treatment group, mice were administered with a mixture of hemoglobin conjugated to Alexa Fluor 647 fluorescent dye and unconjugated hemoglobin in a ratio of 1:80 (c-hemoglobin), while for the control group, mice were administered with unconjugated hemoglobin only. All mice were injected intravenous through tail vein with an interval of 60 minutes according to Table 16.

TABLE 16

Illustration of Injection Sequence of Pegylated Cysteinyl-succinyl Crosslinked Hemoglobin.

| Time (hour) | Treatment | n |
|---|---|---|
| 0 | c-hemoglobin (Treatment Group) | 1 |
| 1 | | 1 |
| 2 | | 1 |
| 3 | | 1 |
| 3 | Unconjugated Hemoglobin (Control Group) | 1 | c-hemoglobin: mixture of hemoglobin conjugated to Alexa Fluor 647 fluorescent dye and unconjugated hemoglobin in a ratio of 1:80.

After the injections, mice were anesthetized by 3% isoflurane inhalant within an induction chamber and subsequently transferred to the IVIS® Spectrum in vivo imaging system (PerkinElmer) with continuous supply of isoflurane/oxygen. Fluorescence signals were measured with filters at 620 nm (excitation) and 670 nm (emission) and serial images were taken at every 10 minutes for 1 hour. The imaging procedure was repeated at 4, 24 and 72 hours after the first recording.

A separate experiment was also performed to measure the fluorescence signals in vital organs (liver, kidney, spleen, lungs and heart) of the mice as well as the biochemical changes in urine. Intravenous injections were made at time 0, according to Table 16 and the mice were sacrificed at 6 hours after injection. Sampled organs from the groups were subsequently measured for their fluorescence levels using IVIS® Spectrum in vivo imaging system, while the fluorescence level from urine was measured using FLUOstar Omega microplate reader (BMG LABTECH). An illustration of the study setup was shown in Table 17.

TABLE 17

Urine Collection and Organ Imaging Study Setup.

| Group | Injection | n |
|---|---|---|
| 1 | No injection (Control group) | 2 |
| 2 | c-Hemoglobin (cysteinyl-succinyl crosslinked hemoglobin) | 2 |
| 3 | c-Hemoglobin (pegylated cysteinyl-succinyl crosslinked hemoglobin) | 2 | c-hemoglobin: mixture of hemoglobin conjugated to Alexa Fluor 647 fluorescent dye and unconjugated hemoglobin in a ratio of 1:80.

Figure 20:
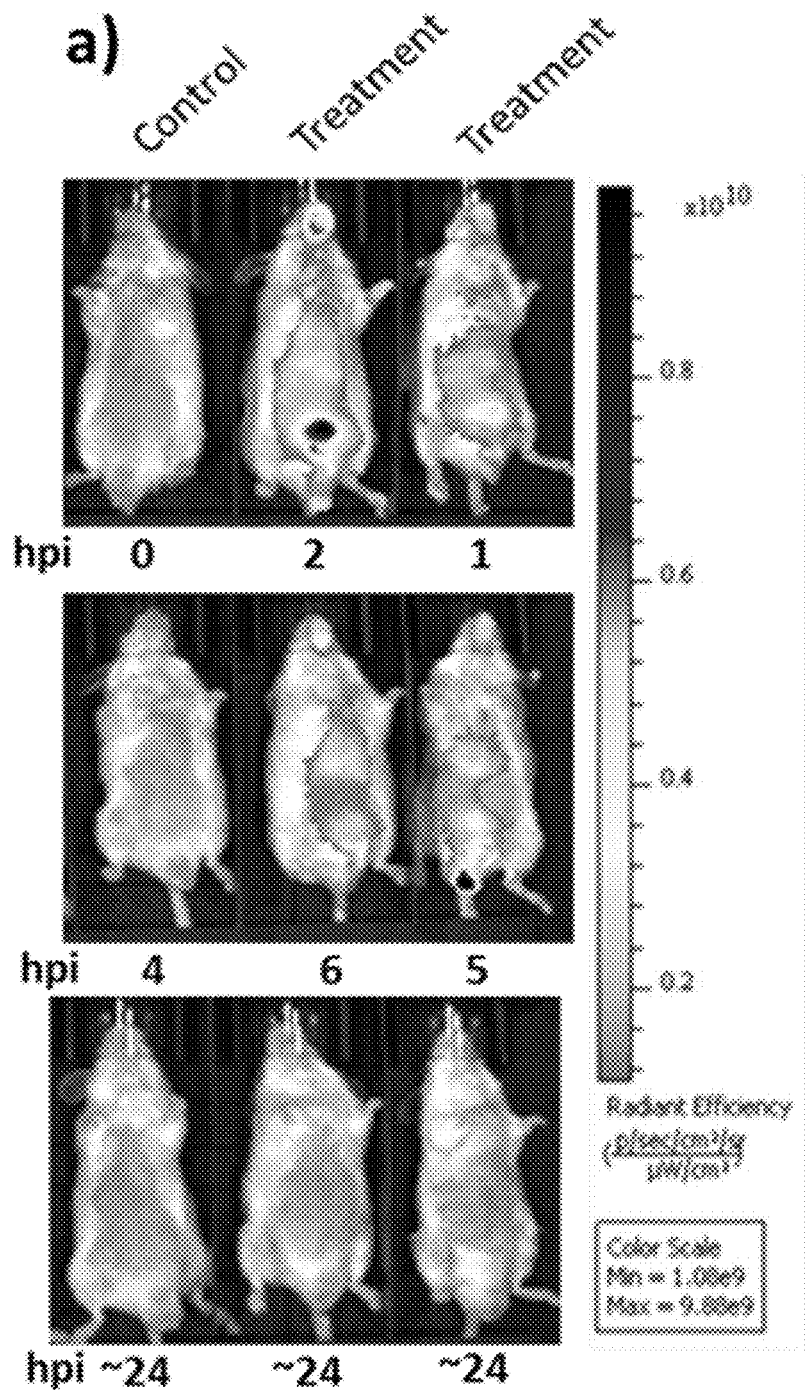
FIG. 20 shows the IVIS spectrum examination of distribution of (a) cysteinyl-succinyl crosslinked hemoglobin and (b) pegylated cysteinyl-succinyl crosslinked hemoglobin in mice. Control Group: unconjugated hemoglobin; Treatment Group: cyanine 5 sold under the trademark Alexa Fluor® 647 by Thermo Fisher Scientific conjugated to hemoglobin; hpi: hours post-injection.
Figure 20:
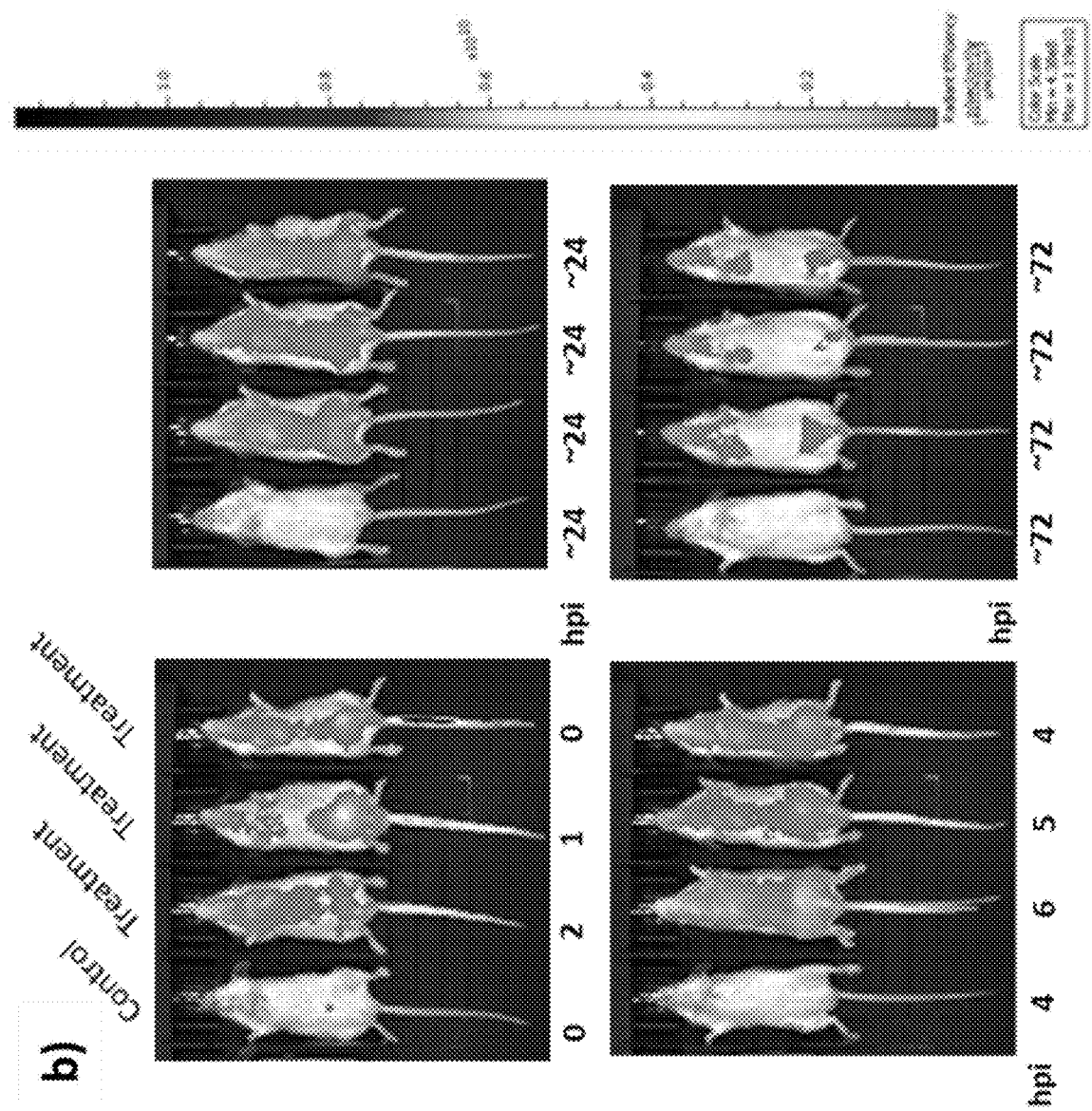

The IVIS spectra of pegylated cysteinyl-succinyl crosslinked hemoglobin and unpegylated ones are shown in FIG. 20. Both pegylated and unpegylated cysteinyl-succinyl crosslinked hemoglobin was gradually distributed to the whole body within 2 hours, but IVIS signal of unpegylated hemoglobin was undetectable after 24 hours post-injection, as shown in FIG. 20A, while IVIS signal of pegylated cysteinyl-succinyl crosslinked hemoglobin was still detectable after 72 hours post-injection, as shown in FIG. 20B. This indicates that the pegylated hemoglobin can impart longer circulating time by modification of the physicochemical properties of crosslinked hemoglobin. This can enhance localization to sites of interest for potential treatment compared with unpegylated ones.

Figure 21:
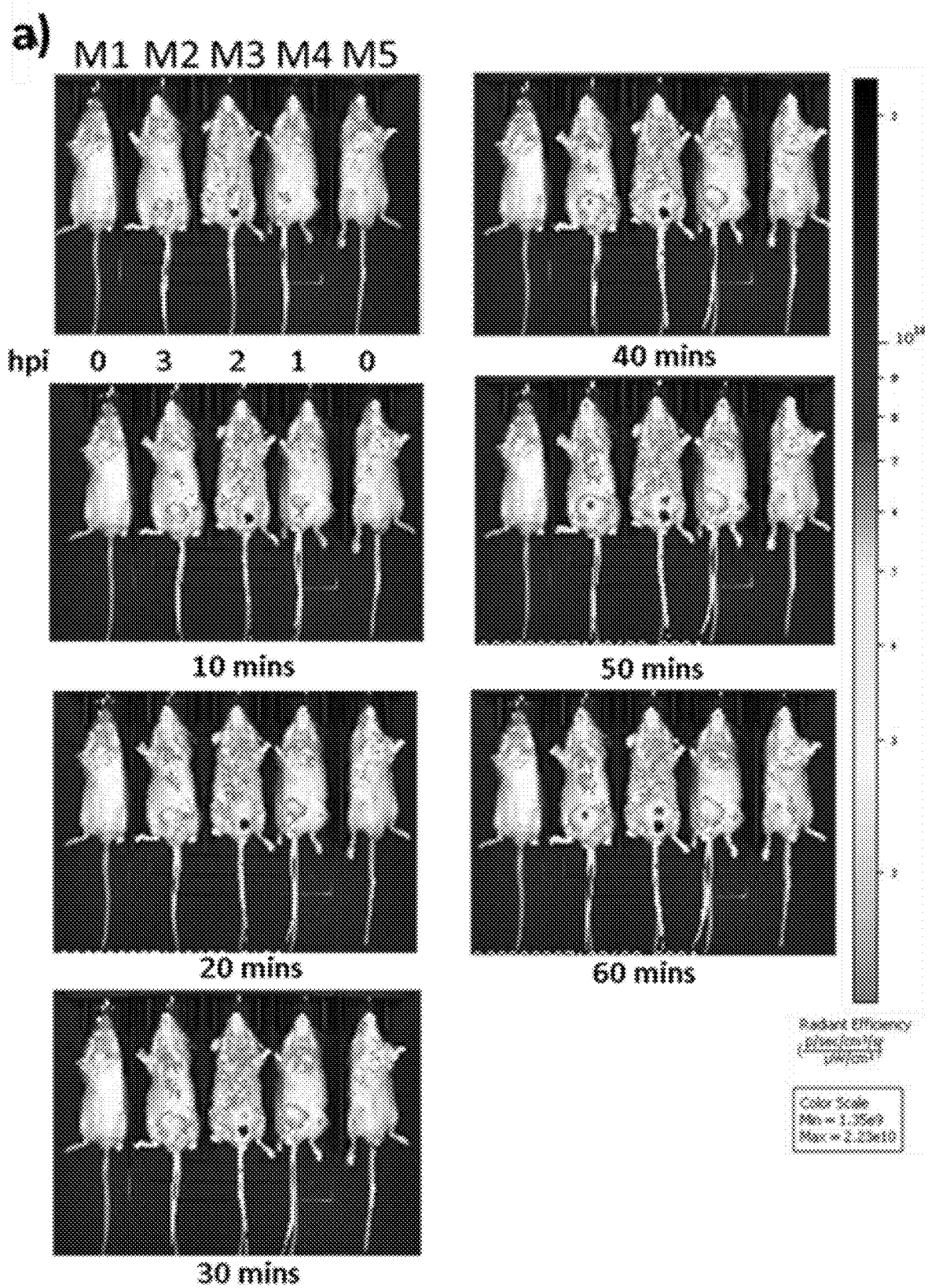
FIG. 21 shows the IVIS spectrum examination of distribution of (a) cysteinyl-succinyl crosslinked hemoglobin and (b) pegylated cysteinyl-succinyl crosslinked hemoglobin in mice with serial images taken every 10 minutes. M1: Control Group (unconjugated hemoglobin); M2 to M5: Treatment Group (AlexaFluor 647 conjugated to hemoglobin); hpi: hours post-injection.
Figure 21:
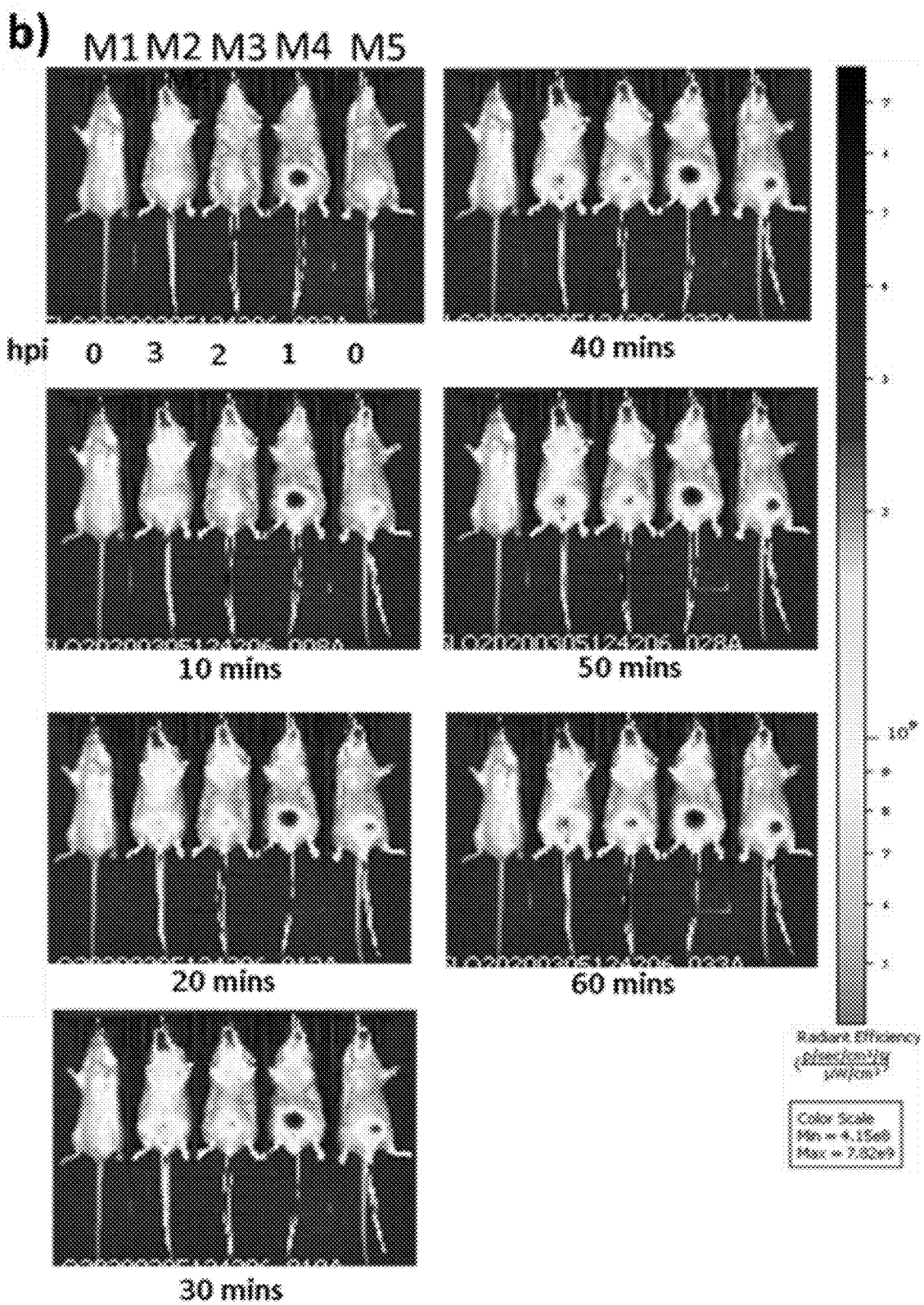

Moreover, FIG. 21 showed that the IVIS signals at bladder increased with time, indicating there is an accumulation of the succinyl crosslinked hemoglobin in the bladder. The renal clearance of drug was highly possibly through urination. The collected urine shows strong fluorescent intensity (>80 fold stronger than the control group). This result confirms the drug was cleared and broken down through kidney.

Figure 22:
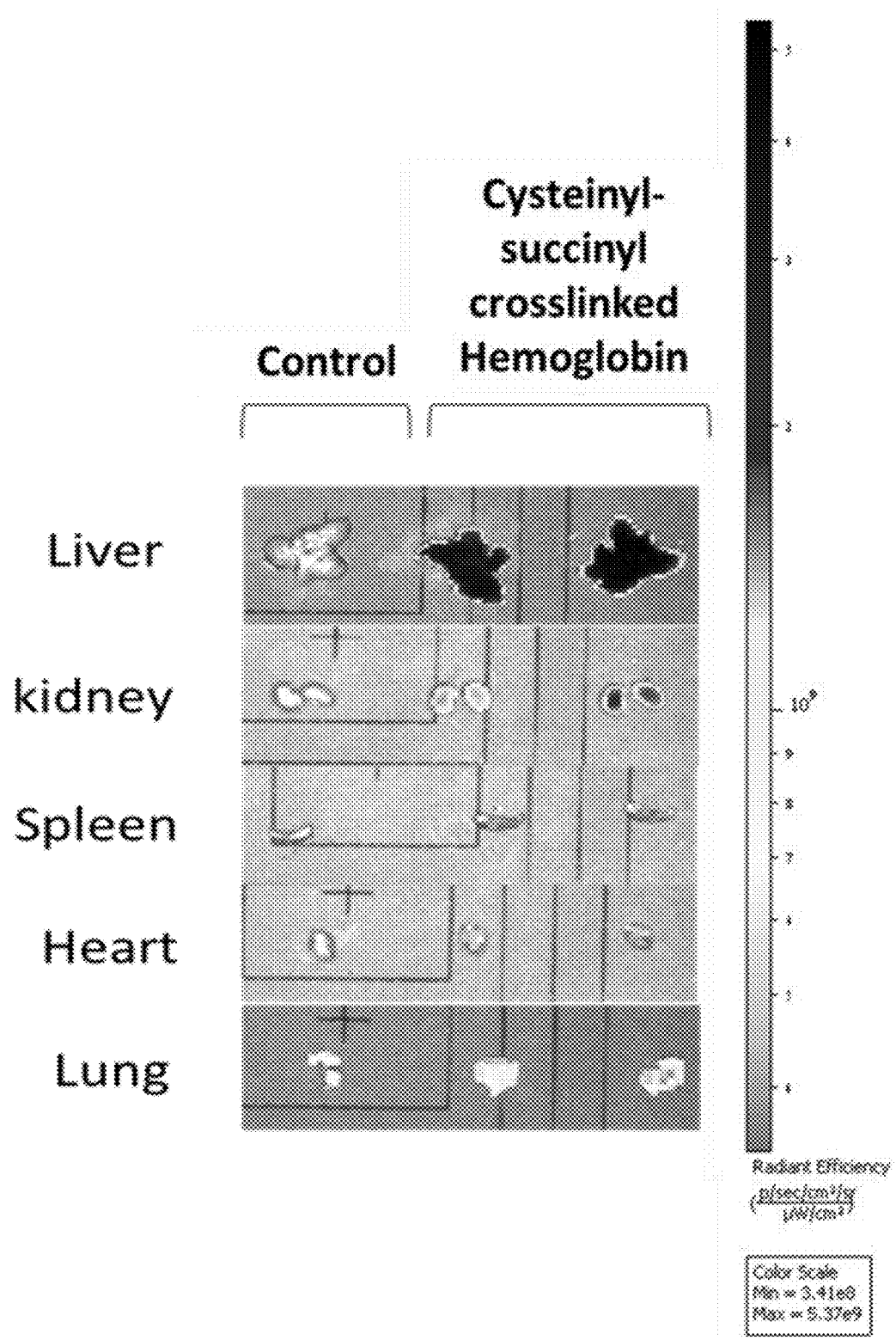
FIG. 22 shows the IVIS spectrum examination of vital organs at 3 hours and 6 hours post-injection of cysteinyl-succinyl crosslinked hemoglobin and pegylated cysteinyl-succinyl crosslinked hemoglobin, respectively.
Figure 22:
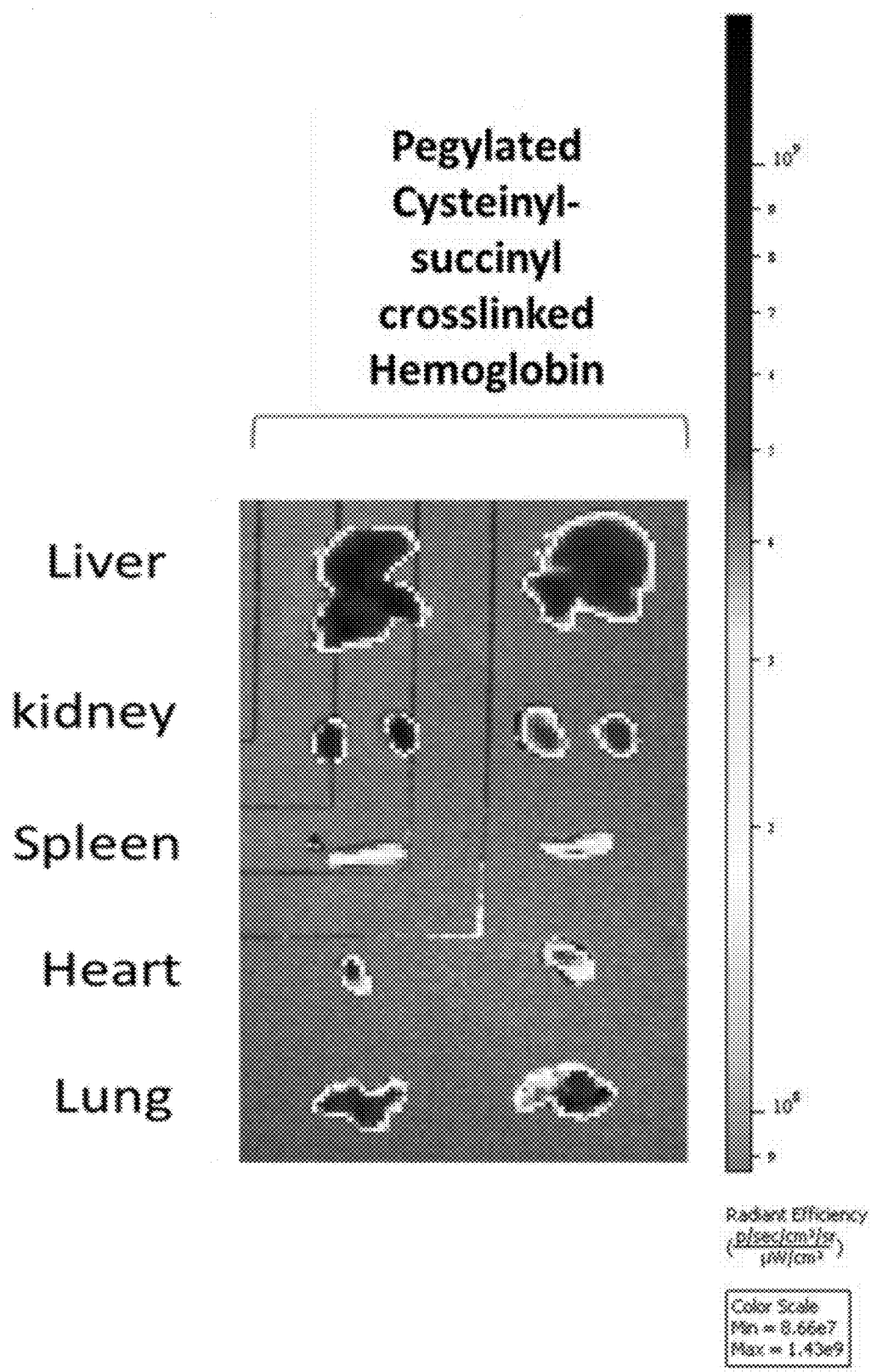

Importantly, the results also revealed that pegylated cysteinyl-succinyl crosslinked hemoglobin was well distributed in all vital organs at 6 hours post-injection, while the unpegylated cysteinyl-succinyl crosslinked hemoglobin was mainly accumulated in the liver at 3 hours post-injection, as shown in FIG. 22. This reflects that the pegylation changes the pharmacokinetics of cysteinyl-succinyl crosslinked hemoglobin, which may widen the application of pegylated cysteinyl-succinyl crosslinked hemoglobin.

In sum, the results suggest that the pegylated cysteinyl-succinyl crosslinked hemoglobin has outstanding pharmacokinetic and pharmacodynamics properties, resulting in enhanced in vivo circulation stability and specific organ/tissue bioavailability for different therapeutic indications.

Example 13: Restoration of Liver Tissue Oxygenation in Hemorrhagic Shock

A fixed-pressure of hemorrhagic shock model was used for evaluating the efficacy of in vivo liver tissue oxygenation ($TO_2$) of pegylated cysteinyl-succinyl crosslinked hemoglobin and the unpegylated ones. Sprague-Dawley male rats ranging from 300-320 g were put under anesthesia. Sterile catheters primed with saline were tunneled into left femoral vein, left femoral artery and right femoral vein, and a sensor with pressure measurement function was tunneled into the right femoral artery. A fiber optic probe was placed between right and triangular lobes and the real-time tissue oxygen ($TO_2$) was measured. In this model, the drop of mean arterial pressure (MAP) was induced by removing 0.1 mL blood for every 10 seconds from the femoral artery catheter and maintained at the margin of 60 mmHg or below during hemorrhagic shock. Subsequently, the resuscitation process was preceded only when the arterial lactate concentration reached 8.00-11.00 mmol/L. Blood was collected at baseline, during hemorrhagic shock, 60 and 120 min after resuscitation for measuring the lactate concentration.

Figure 23:
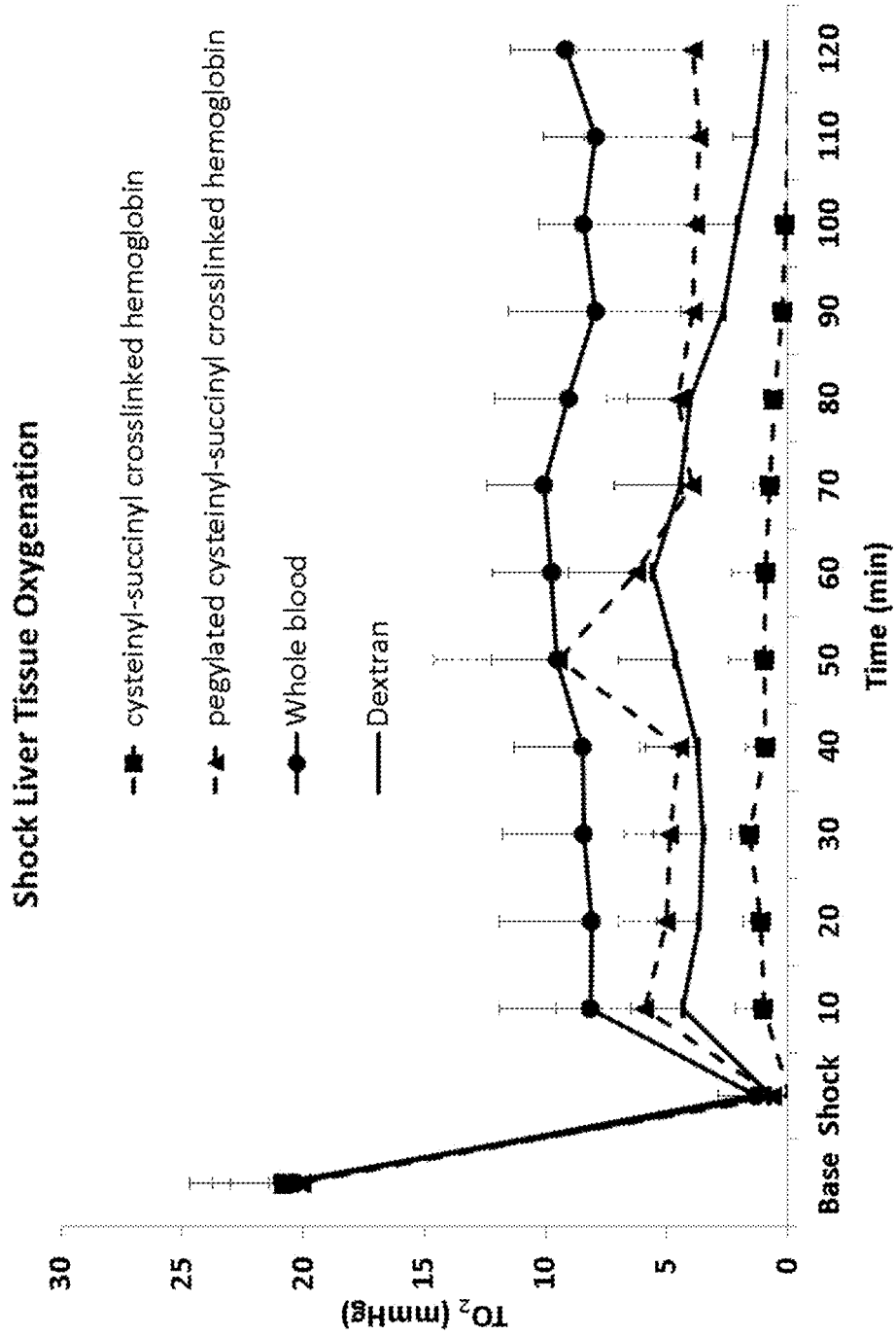
FIG. 23 shows the real-time measurement of the rat liver $TO_2$ level in hemorrhagic shock. $TO_2$ level of cysteinyl-succinyl crosslinked hemoglobin, pegylated cysteinyl-succinyl crosslinked hemoglobin, dextran (negative control) and whole blood (positive control) was shown from baseline to 120 minutes.
Figure 24:
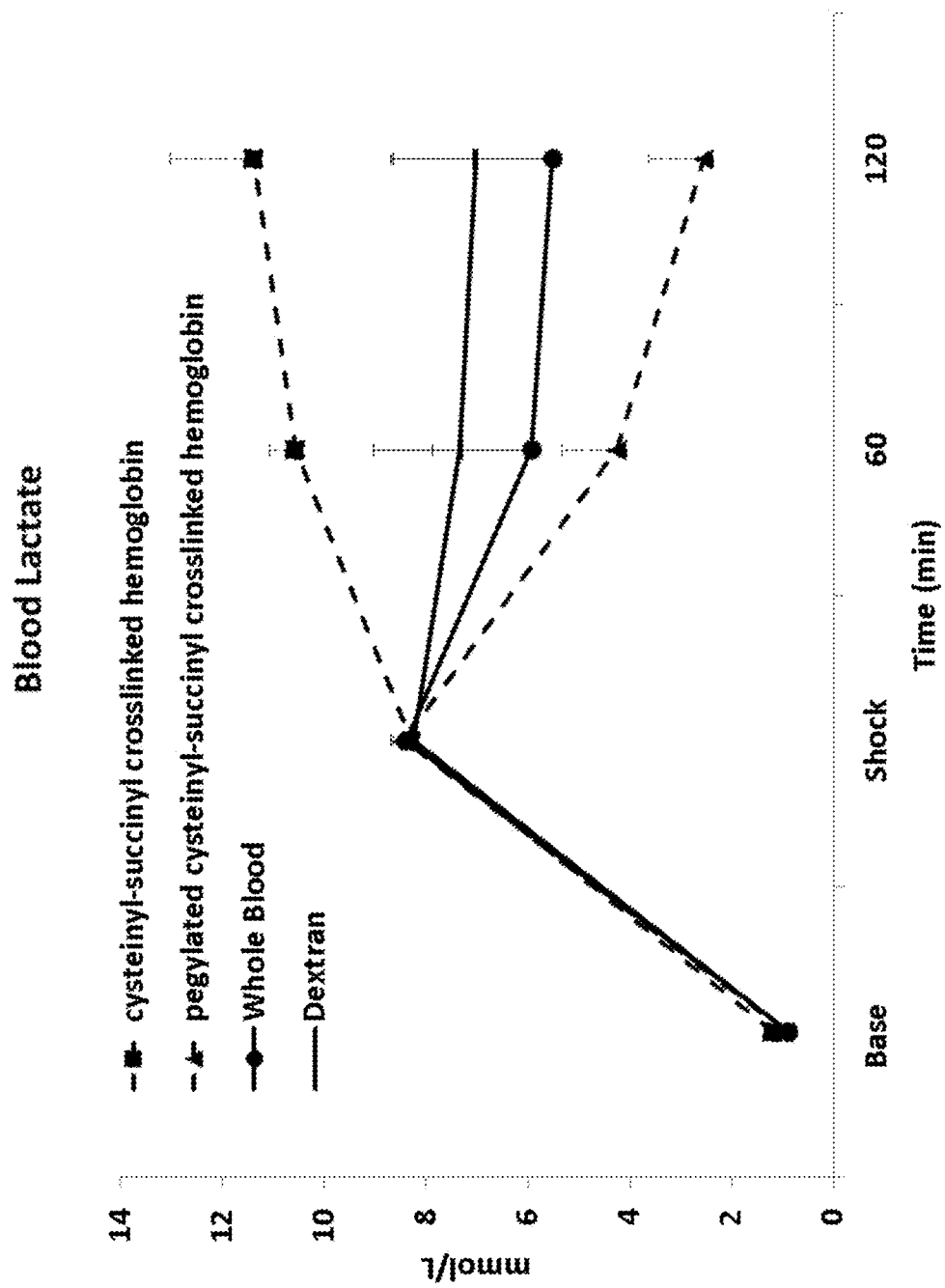
FIG. 24 shows the lactate measurement of rat blood at baseline, during resuscitation, 60 and 120 minutes after resuscitation.

The results showed an increased tissue oxygen ($TO_2$) was observed after resuscitation of either pegylated or unpegylated crosslinked hemoglobin in this rat hemorrhagic shock model, as shown in FIG. 23. While the increased $TO_2$ level for pegylated cysteinyl-succinyl crosslinked hemoglobin was higher than dextran (negative control) but below that of the whole blood (positive control), the $TO_2$ level for the unpegylated ones was below both controls. The $TO_2$ level remained stable for at least 60 minutes after completing the resuscitation for the pegylated cysteinyl-succinyl crosslinked hemoglobin, but gradually dropped for the unpegylated ones. This suggested that pegylated hemoglobin might have better tissue oxygenation in rat liver than unpegylated hemoglobin. Importantly, the results also revealed that the lactate concentration was back to almost baseline level at 120 min after resuscitation for pegylated crosslinked hemoglobin compared to unpegylated ones, as shown in FIG. 24. These findings suggested that the resuscitation with the pegylated cysteinyl-succinyl crosslinked hemoglobin would improve the $TO_2$ restoring ability and also the metabolic function in rats with hemorrhagic shock condition.

What is claimed:
1. A thiosuccinyl-crosslinked hemoglobin conjugate comprising a tetrameric hemoglobin; at least one water-soluble polymer covalently attached to the tetrameric hemoglobin via an optional linker; and at least one thiosuccinyl crosslinking moiety of Formula 1:

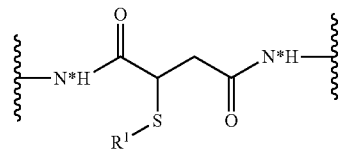

or a pharmaceutically acceptable salt or zwitterion thereof, wherein each N* independently represents a nitrogen selected from the group consisting of a nitrogen in a lysine residue side chain in the tetrameric hemoglobin and a nitrogen at a N-terminus in the tetrameric hemoglobin;

$R^1$ is alkyl, alkenyl, cycloalkyl, heterocycloalkyl, aryl, aralkyl, heteroaryl, or —$(CR_2)_n Y$, wherein n is an integer number selected from 0-10;

R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S;

Y is selected from the group consisting of $OR^4$, $SR^4$, $N(R^4)_2$, —$(C=O)R^4$, —$(C=O)OR^4$, —$O(C=O)R^4$, —$O(C=O)OR^4$, —$(C=O)N(R^4)_2$, —$(NR_4)(C=O)R^4$, —$(NR^4)(C=O)OR^4$, —$O(C=O)N(R^4)_2$, —$O(C=NR^4)N(R^4)_2$, —$(NR_4)(C=O)N(R^4)_2$, —$(C=NR^4)N(R^4)_2$, —$(NR^4)(C=NR^4)N(R^4)_2$, —$(S=O)R^4$, —$S(O)_2R^4$, —$S(O)_2OR^4$, —$S(O)_2N(R^4)_2$, —$OS(O)_2R^4$, —$(NR^4)S(O)_2R^4$, —$OS(O)_2OR^4$, —$OS(O)N(R^4)_2$, —$(NR^4)S(O)_2N(R)_2$, —$(NR_4)S(O)_2OR^4$, and —$(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, —$(C=O)R^4$, —$(C=O)OR^4$, —$(C=O)R^4$, —$O(C=O)OR^4$, —$(C=O)N(R^4)_2$, —$(NR^4)(C=O)R^4$, —$(NR^4)(C=O)OR^4$, —$O(C=O)N(R^4)_2$, —$(C=NR^4)N(R^4)_2$, —$(NR^4)(C=O)N(R^4)_2$, —$(C=NR^4)N(R^4)_2$, —$(NR^4)(C=NR^4)N(R^4)_2$, —$(S=O)R^4$, —$S(O)_2R^4$, —$S(O)_2OR^4$, —$S(O)_2N(R^4)_2$, —$OS(O)_2R^4$, —$(NR^4)S(O)_2R^4$, —$OS(O)_2OR^4$, —$OS(O)_2N(R^4)$, —$(NR^4)S(O)_2N(R^4)_2$, or —$(NR_4)S(O)_2OR^4$;

$R^3$ is hydrogen, alkyl, aralkyl, cycloalkyl, heterocycloalkyl, aryl, heteroaryl, $OR^4$, $SR^4$, $N(R^4)_2$, —$(C=O)R^4$, —$(C=O)OR^4$, —$O(C=O)R^4$, —$O(C=O)OR^4$, —$(C=O)N(R^4)_2$, —$(NR^4)(C=O)R^4$, —$(NR^4)(C=O)OR^4$, —$O(C=O)N(R^4)_2$, —$O(C=NR_4)N(R^4)_2$, —$(NR^4)(C=O)N(R^4)_2$, —$(C=NR^4)N(R^4)_2$, —$(NR^4)(C=NR^4)N(R^4)_2$, —$(S=O)R^4$, —$S(O)_2R^4$, —$S(O)_2OR^4$, —$S(O)_2N(R^4)_2$, —$OS(O)_2R^4$, —$(NR^4)S(O)_2R^4$, —$OS(O)_2OR^4$, —$OS(O)_2N(R^4)_2$, —$(NR^4)S(O)_2N(R^4)_2$, or —$(NR^4)S(O)_2OR^4$; and $R^4$ for each instance is independently selected from the group consisting of hydrogen, alkyl, aralkyl, cycloalkyl, heterocycloalkyl, aryl, and heteroaryl; or $R^1$ is a moiety selected from the group consisting of:

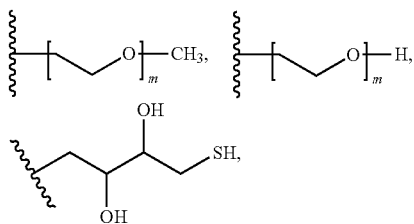

N⁵-(1-((carboxymethyl)amino)-1-oxo-3λ³-propan-2-yl) glutamine or a pharmaceutically acceptable salt thereof, wherein m is a whole number selected from 1-1,000.

2. The thiosuccinyl-crosslinked hemoglobin conjugate of claim 1, wherein the at least one water-soluble polymer comprises a polyalkylene glycol.

3. The thiosuccinyl-crosslinked hemoglobin conjugate of claim 1, wherein the at least one water-soluble polymer and the linker have a formula selected from the group consisting of:

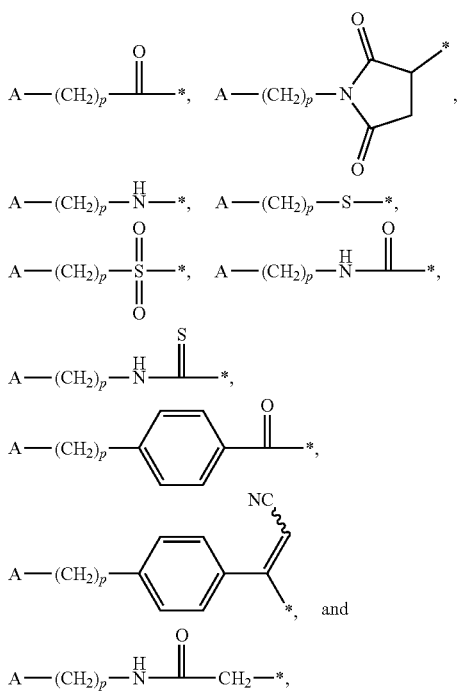

wherein A represents the water-soluble polymer, p is a whole number selected from 1-20; and * represents the tetrameric hemoglobin.

4. The thiosuccinyl-crosslinked hemoglobin conjugate of claim 1, wherein the at least one water-soluble polymer and the linker have the formula:

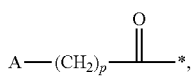

wherein A is a polyethylene glycol; p is a whole number selected from 1-20; and * represents the tetrameric hemoglobin.

5. The thiosuccinyl-crosslinked hemoglobin conjugate of claim 4, wherein the polyethylene glycol has an average molecular weight between 1,000 to 50,000 Daltons.

6. The thiosuccinyl-crosslinked hemoglobin conjugate of claim 1, wherein the thiosuccinyl-crosslinked hemoglobin conjugate comprises between 1-50 water-soluble polymers, wherein each water-soluble polymer is covalently attached to the tetrameric hemoglobin via a linker.

7. The thiosuccinyl-crosslinked hemoglobin conjugate of claim 1, wherein the thiosuccinyl-crosslinked hemoglobin conjugate comprises between 10-15 water-soluble polymers, wherein each water-soluble polymer is covalently attached to the tetrameric hemoglobin via a linker.

8. The thiosuccinyl-crosslinked hemoglobin conjugate of claim 1, wherein R¹ is a moiety of Formula 2:

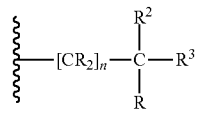

wherein n is a whole number selected from the group consisting of 0, 1, 2, 3, and 4;

R for each instance is independently selected from the group consisting of hydrogen, alkyl, aralkyl, cycloalkyl, heterocycloalkyl, aryl, and heteroaryl;

R² is hydrogen, alkyl, aralkyl, cycloalkyl, heterocycloalkyl, aryl, heteroaryl, —N(R⁴)₂, —NH(C=O)R⁴, or —NH(C=O)N(R⁴)₂;

R³ is hydrogen, alkyl, aralkyl, cycloalkyl, heterocycloalkyl, aryl, heteroaryl, —CO₂R⁴, —(C=O)NHR⁴, —OR⁴, or —N(R⁴)₂; and R⁴ for each instance is independently selected from the group consisting of hydrogen, alkyl, aralkyl, cycloalkyl, heterocycloalkyl, aryl, and heteroaryl;

or R¹ is a moiety selected from the group consisting of:

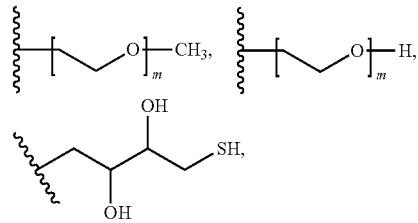

N⁵-(1-((carboxymethyl)amino)-1-oxo-3λ³-propan-2-yl) glutamine or a pharmaceutically acceptable salt thereof, wherein m is a whole number selected from 1-1,000.

9. The thiosuccinyl-crosslinked hemoglobin conjugate of claim 8, wherein n is 1 or 2; R is hydrogen; R² is —NHR⁴, —NH(C=O)R⁴, or —NH(C=O)R⁴N(R⁴)₂; and R³ is hydrogen, —OR⁴, —CO₂R⁴, or —(C=O)NHR⁴, wherein R for each instance is independently selected from the group consisting of hydrogen and alkyl.

10. The thiosuccinyl-crosslinked hemoglobin conjugate of claim 1, wherein R¹ is selected from the group consisting of:

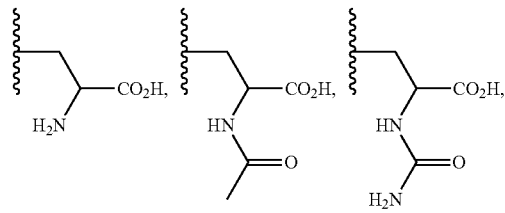

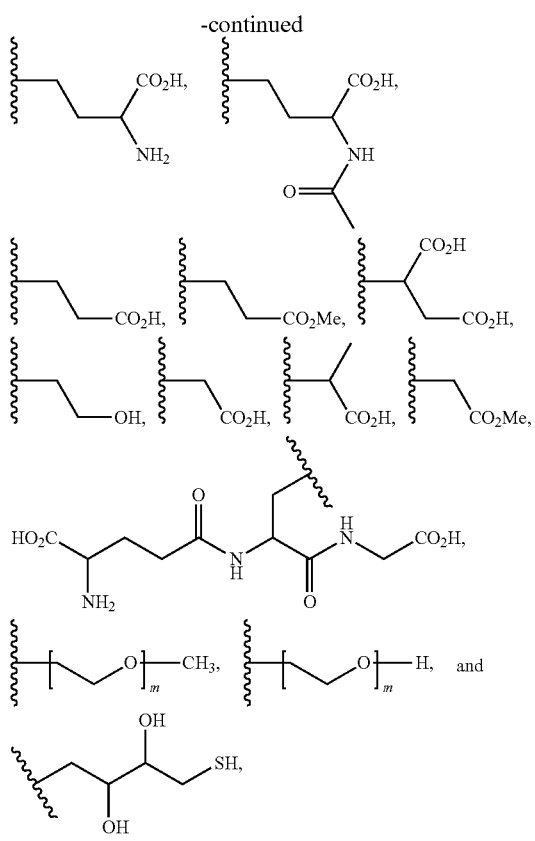

or a pharmaceutically acceptable salt or zwitterion thereof, wherein m is a whole number selected from 1-1,0).

11. The thiosuccinyl-crosslinked hemoglobin conjugate of claim 1, wherein the thiosuccinyl-crosslinked hemoglobin conjugate comprises 10-15 water-soluble polymers and linker having the formula:

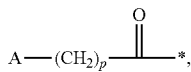

wherein A is a polyethylene glycol having an average molecular weight of 3,000-7,000 Daltons; p is a whole number selected from 1-20; and * represents the tetrameric hemoglobin.

12. The thiosuccinyl-crosslinked hemoglobin conjugate of claim 1, wherein each N* independently represents a nitrogen selected from the group consisting of a nitrogen in a lysine residue side chain in a beta globin chain of the tetrameric hemoglobin and a nitrogen at a N-terminus in a beta globin chain of the tetrameric hemoglobin.

13. The thiosuccinyl-crosslinked hemoglobin conjugate of claim 1, wherein the thiosuccinyl-crosslinked hemoglobin conjugate is substantially pure.

14. The thiosuccinyl-crosslinked hemoglobin conjugate of claim 1, wherein the thiosuccinyl-crosslinked hemoglobin conjugate comprises 1, 2, or 3 thiosuccinyl crosslinking moieties of Formula 1.

15. The thiosuccinyl-crosslinked hemoglobin conjugate of claim 1, wherein the at least one thiosuccinyl crosslinking moiety crosslinks two beta globin chains of the tetrameric hemoglobin.

16. The thiosuccinyl-crosslinked hemoglobin conjugate of claim 1, wherein the tetrameric hemoglobin is human hemoglobin, bovine hemoglobin, or porcine hemoglobin.

17. The thiosuccinyl-crosslinked hemoglobin of claim 1, wherein the thiosuccinyl-crosslinked hemoglobin conjugate is substantially stroma-free.

18. A pharmaceutical composition comprising at least one of the thiosuccinyl-crosslinked hemoglobin conjugate of claim 1 and at least one pharmaceutically acceptable excipient.

19. The pharmaceutical composition of claim 18, wherein the thiosuccinyl-crosslinked hemoglobin conjugate is present in the pharmaceutical composition at a weight percentage between 10-90%.

20. The pharmaceutical composition of claim 18, wherein the pharmaceutical composition comprises thiosuccinyl-crosslinked hemoglobin conjugate comprising 1, 2, or 3 thiosuccinyl crosslinking moieties of Formula 1; or a combination thereof.

21. A method for preparing the thiosuccinyl-crosslinked hemoglobin conjugate of claim 1, the method comprising:
contacting a tetrameric hemoglobin with a fumaryl crosslinking agent thereby forming a fumaryl-crosslinked hemoglobin: contacting the fumaryl-crosslinked hemoglobin with a thiol or a pharmaceutically acceptable salt or zwitterion thereof thereby forming a thiosuccinyl-crosslinked hemoglobin; and contacting the thiosuccinyl-crosslinked hemoglobin with a reactive water-soluble polymer reagent comprising a water-soluble polymer, a reactive functional group and optionally a linker, wherein the linker is covalently attached to the water-soluble polymer and the reactive functional group, thereby forming the thiosuccinyl-crosslinked hemoglobin conjugate.

22. The method of claim 21, wherein the fumaryl crosslinking agent is selected from the group consisting of bis-3,5-dibromosalicyl fumarate (DBSF), fumaryl chloride and bis(salicyl) fumarate.

23. The method of claim 21, wherein the thiol has the formula: $R^1SH$ or a pharmaceutically acceptable salt or zwitterion thereof, wherein $R^1$ is alkyl, alkenyl, cycloalkyl, heterocycloalkyl, aryl, aralkyl, heteroaryl, or —$(CR_2)_{,1}Y$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S; and Y is selected from the group consisting of $R^1$ is alkyl, alkenyl, cycloalkyl, heterocycloalkyl, aryl, aralkyl, heteroaryl, or —$(CR_2)_nY$, wherein n is an integer selected from 0-10; R for each instance is independently hydrogen, alkyl, aralkyl, alkenyl, cycloalkyl, heterocycloalkyl, aryl, or heteroaryl; or two instances of R taken together form a 3-6 membered cycloalkyl or heterocycloalkyl containing 1, 2, or 3 heteroatoms selected from N, O, and S: and Y is selected from the group consisting of $OR^4$, $SR^4$, $N(R^4)_2$, —$(C=O)R^4$, —$(C=O)OR^4$, —$O(C=O)R^4$, —$O(C=O)OR^4$, —$(C=O)N(R^4)_2$, —$(NR^4)(C=O)R^4$, —$(NR^4)(C=O)OR^4$, —$O(C=O)N(R^4)_2$, —$O(C=N\ R^4)N(R^4)_2$, —$(NR^4)(C=O)N(R^4)_2$, —$(C=NR^4)N(R^4)_2$, —$(NR^4)(C=NR^4)N(R^4)_2$, —$(S=O)R^4$, —$S(O)_2R^4$, —$S(O)_2OR^4$, —$S(O)_2N(R^4)_2$, —$OS(O)_2R^4$, —$(NR^4)S(O)_2R^4$, —$OS(O)_2OR$, —$OS(O)_2N(R^4)_2$, —$(NR^4)S(O)_2N(R^4)_2$, —$(NR^4)S(O)_{20}R^4$, and —$(CRR^2R^3)$, wherein $R^2$ is hydrogen, alkyl, aralkyl, cycloalkyl, heterocycloalkyl, aryl, heteroaryl, $OR^4$, $SR^4$, $N(R^4)_2$, —$(C=O)R^4$, —$(C=O)OR^4$, —$O(C=O)R^4$, —$O(C=O)OR^4$, —$(C=O)N(R^4)_2$, —(NR⁴)(C═O)R⁴, —(NR⁴)(C═O)R⁴, —O(C═O)N(R⁴), —O(C═NR⁴)N(R⁴)₂, —(NR⁴)(C═O)N(R⁴)₂, —(C═NR⁴)N(R⁴)₂, —(NR₄)(C═NR⁴)N(R⁴)₂, —(S═O)R⁴, —S(O)₂R⁴, —S(O)₂OR⁴, —S(O)₂N(R)₂—, —OS(O)₂R⁴, —(NR⁴)S(O)₂R, —OS(O)₂₀R⁴, —OS(O)₂N(R⁴)₂, —(NR⁴)S(O)₂N(R⁴)₂, or —(NR⁴)S(O)₂OR⁴; R³ is hydrogen, alkyl, aralkyl, cycloalkyl, heterocycloalkyl, aryl, heteroaryl, OR⁴, SR⁴, N(R⁴)₂, —(C═O)R⁴, —(C═O)OR⁴, —O(C═O)R⁴, —O(C═O)OR⁴, —(C═O)N(R')₂, —(NR⁴)C═O)R⁴, —(NR⁴)(C═O)OR⁴, —O(C═O)N(R⁴)₂, —O(C═NR⁴)N(R⁴)₂, —(NR⁴)(C═O)N(R⁴)₂, —(C═NR⁴)N(R⁴)₂, —(NR⁴)(C═NR⁴)N(R⁴)₂, —(S═O)R⁴, —S(O)₂R⁴, —S(O)₂OR⁴, —S(O)₂N(R⁴)₂, —OS(O)₂R⁴, —(NR⁴)S(O)₂R⁴, —OS(O)₂OR⁴, —OS(O)₂N(R⁴)₂, —(NR⁴)S(O)₂N(R⁴)₂, or —(NR⁴)S(O)₂₀R⁴; and R⁴ for each instance is independently selected from the group consisting of hydrogen, alkyl, aralkyl, cycloalkyl, heterocycloalkyl, aryl, and heteroaryl; or R¹ is a moiety selected from the group consisting of:

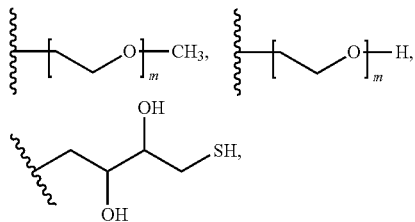

N⁵-(1-((carboxymethyl)amino)-1-oxo-3K'-propan-2-yl) glutamine or a pharmaceutically acceptable salt thereof, wherein m is a whole number selected from 1-1000.

24. The method of claim 21, wherein the thiol has the Formula 3:

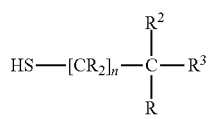

or a pharmaceutically acceptable salt or zwitterion thereof, wherein n is an integer selected from the group consisting of 0, 1, 2, 3, and 4;

R for each instance is independently selected from the group consisting of hydrogen, alkyl, aralkyl, cycloalkyl, heterocycloalkyl, aryl, and heteroaryl;

R² is hydrogen, alkyl, aralkyl, cycloalkyl, heterocycloalkyl, aryl, heteroaryl, —N(R⁴)₂, or —NH(C═O)Ra;

R³ is hydrogen, alkyl, aralkyl, cycloalkyl, heterocycloalkyl, aryl, heteroaryl, —CO₂R⁴, —(C═O)NHR⁴, —OR⁴, or —N(R⁴)₂; and R⁴ for each instance is independently selected from the group consisting of hydrogen, alkyl, aralkyl, cycloalkyl, heterocycloalkyl, aryl, and heteroaryl: or the thiol is selected from the group consisting of dithiothreitol, HS(CH₂CH₂O)ₘCH₃, HS(CH₂CH₂O)ₘH, glutathione or a pharmaceutically acceptable salt thereof, wherein m is a whole number selected between 1-1000.

25. The method of claim 24, wherein n is 1 or 2; R is hydrogen; R² is —NHR⁴, —NH(C═O)R⁴, or —NH(C═O) (NR⁴)₂; and R³ is hydrogen, —OR⁴, —CO₂R⁴, or —(C═O)NHR⁴, wherein R⁴ for each instance is independently selected from the group consisting of hydrogen and alkyl.

26. The method of claim 21, wherein the thiol is selected from the group consisting of

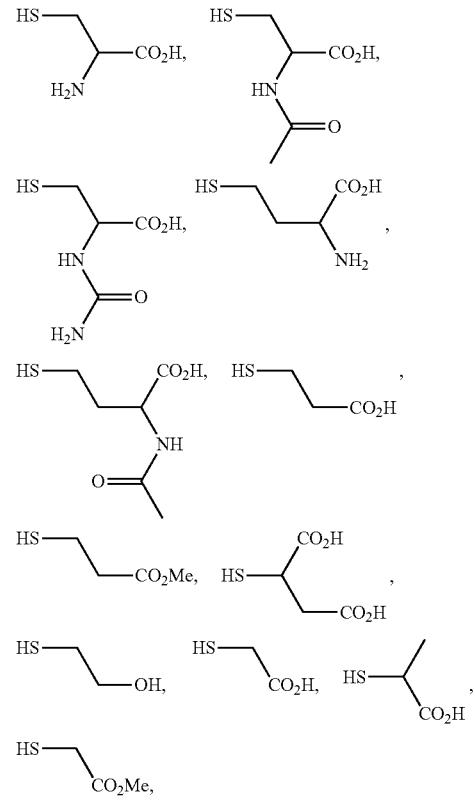

dithiothreitol, HS(CH₂CH₂O)ₘCH₃, and HS(CH₂CH₂O)ₘH or a pharmaceutically acceptable salt or zwitterion thereof, wherein m is a whole number selected between 1-1000.

27. The method of claim 21, wherein the reactive water-soluble polymer reagent is selected from the group consisting of:

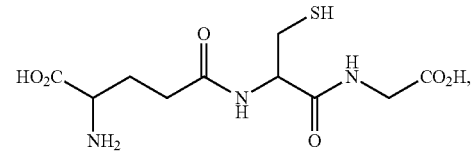

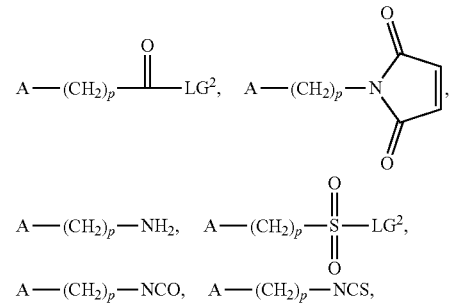

-continued

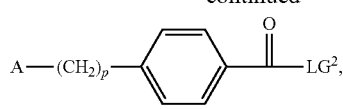

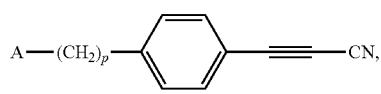

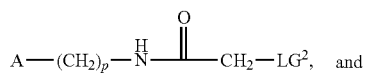

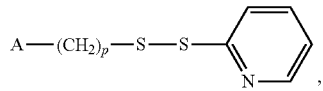

wherein A represents the water-soluble polymer; LG² is a leaving group; and p is a whole number between 1-20.

28. The method of claim 21, wherein the reactive water-soluble polymer reagent is

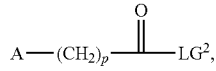

wherein A is PEG; LG² is

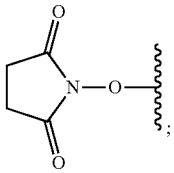 [SMILES: *ON1C(=O)CCC1=O]

and p is 1-20.

29. The method of claim 21, wherein the step of contacting the thiosuccinyl-crosslinked hemoglobin with the reactive water-soluble polymer reagent, the reactive water-soluble polymer reagent and the thiosuccinyl-crosslinked hemoglobin are contacted in a molar ratio between 1:1-150:1, respectively.

30. The method of claim 21, wherein the step of contacting the fumaryl-crosslinked hemoglobin with a thiol or a pharmaceutically acceptable salt or zwitterion thereof, the fumaryl-crosslinked hemoglobin and the thiol are present in a molar ratio of at least 1:1; 1:2; or 1:3.

31. The method of claim 26, wherein the fumaryl-crosslinked hemoglobin and the thiol are present in a molar ratio of greater than 1:3.

32. The method of claim 21, wherein the thiosuccinyl-crosslinked hemoglobin conjugate is prepared in substantially pure form.

33. A method for increasing the volume of the blood circulatory system in a subject in need thereof, wherein the method comprises transfusing into the system of the subject a therapeutically effective amount of the thiosuccinyl-crosslinked hemoglobin conjugate of claim 1.

34. The method of claim 33, wherein the thiosuccinyl-crosslinked hemoglobin conjugate is substantially pure.

* * * * *